United States Patent [19]

Kaddurah-Daouk et al.

[11] Patent Number: 5,321,030
[45] Date of Patent: Jun. 14, 1994

[54] CREATINE ANALOGS HAVING ANTIVIRAL ACTIVITY

[75] Inventors: Rima Kaddurah-Daouk, Watertown; James W. Lillie, Cambridge, both of Mass.; Theodore S. Widlanski, Bloomington, Ind.; Jonathan J. Burbaum, Westfield, N.J.; Craig J. Forsyth, Arlington, Mass.

[73] Assignee: Amira, Inc., Cambridge, Mass.

[21] Appl. No.: 812,561

[22] Filed: Dec. 20, 1991

Related U.S. Application Data

[63] Continuation-in-part of Ser. No. 610,418, Nov. 7, 1990, which is a continuation-in-part of Ser. No. 467,147, Jan. 18, 1990, abandoned, which is a continuation-in-part of Ser. No. 344,963, Apr. 28, 1989, abandoned, which is a continuation-in-part of Ser. No. 310,773, Feb. 14, 1989, abandoned.

[51] Int. Cl.$^5$ .................... A01N 43/54; A01N 43/50; A61K 31/415; A61K 31/505
[52] U.S. Cl. .................................. 514/275; 514/385; 514/386; 514/396; 514/553; 514/501; 514/563; 514/564; 514/579; 514/631; 514/636; 514/646
[58] Field of Search ............... 514/564, 275, 385, 386, 514/396, 533, 561, 563, 564, 579, 631, 638, 646

[56] References Cited

U.S. PATENT DOCUMENTS 4,128,655 12/1978 Hunsucker et al. ............. 424/273 R

FOREIGN PATENT DOCUMENTS

90/00848 7/1990 PCT Int'l Appl. .

OTHER PUBLICATIONS van der Krol et al. Biotechniques 6(10):958–976, 1988.
R. F. Dietrich and G. L. Kenyon, "Synthesis and Investigation with Creatine Kinases of trans-2-Imino-1,-3-diazabicyclo[3.3.0]octane-8-carboxylic Acid, a Bicyclic Analog of Creatine".
*Bioorganic Chemistry*, vol. 12, No. 3, Sep. 1984, pp. 221–228.
R. F. Dietrich et al., "Carbon-13 Nuclear Magnetic Resonance Studies of Creatine, Creatinine and Some Their Analogs", *Organic Magnetic Resonance*, vol. 13, No. 2, Feb. 1980, pp. 79–88.
Yoshio Sakagami and Senzo Kagi, "Studies on the *In Vitro* Synergistic Action of Surface Active Imidazoline Deriatives with Tetracycline Group", *The Journal of Antibiotics*, Ser. A, vol. 19, No. 4, pp. 161–165.
J. J. Roberts and J. B. Walker, "Synthesis and Accumulation of an Extremely Stable High-Energy Phosphate Compound by Muscle, Heart, and Brain of Animals Fed the Creatine Analog, 1-Carboxyethyl-2-Iminoimidazolidine (Homocyclocreatine)", *Archives of Biochemistry and Biophysics*, vol. 220, No. 2, Feb. 1, 1983, pp. 563–571.
T. Wang, "Synthesis and Properties of N-Acetimidoyl Derivative of Glycine and Sarcosine", *J. Org. Chem.*, vol. 39, No. 24, 1974, pp. 3591–3594.
El Hiyani, L. et al., *Biological Abstracts*, 84(9): AB–729, No. 89661 (1987) and *Chem. -Biol. Interactions*, 62:167–178 (1987).

(List continued on next page.)

Primary Examiner—Nathan M. Nutter
Attorney, Agent, or Firm—Lahive & Cockfield

[57] ABSTRACT

The present invention relates to the use of analogs of creatine, such as cyclocreatine, as antiviral agents. Analogs of creatine can be used as antiviral agents against a variety of viruses, particularly DNA viruses, such as Herpes viruses (e.g., HSV-1, HSV-2, cytomegaloviruses, Varicella-Zoster virus) and adenovirus. The invention further relates to creatine analogs including four classes of creatine analogs selected as candidate antiviral compounds: (1) creatine analogs that can be phosphorylated by creatine kinase but differ in their phosphoryl group transfer potential, (2) bisubstrate inhibitors of creatine kinase comprising covalently linked structural analogs of adenosine triphosphate (ATP) and creatine, (3) creatine analogs which can act as irreversible inhibitors of creatine kinase, and (4) N-phosphorocreatine analogs bearing non-transferable moieties which mimic the N-phosphoryl group.

83 Claims, 38 Drawing Sheets

OTHER PUBLICATIONS

Toliekis, A. T. et al., *Biological Abstracts*, 86(11):AB-170, No. 110912 (1988) and *Biokhimiya*, 53(4): 649-654 (1988).

Moss, R. J. et al., *J. Med. Chem.* 31: 786-790 (1988).

Kappler, F. et al., *J. Med. Chem.*, 25: 1179-1184 (1982).

Miranda, A. F. et al., *Proc. Natl. Acad. Sci. USA*, 80:6581-6585 (1983).

Rubery, E. D. et al., *Biological Abstracts*, 76(5): 3844, No. 35410 (1983) and *Eur. J. Cancer Clin. Oncol.*, 18(10): 951-956 (1982).

Gazdar, A. F. et al., *Biological Abstracts*, 805:AB-578, No. 41779 (1985) and *Cancer Res.*, 45(6):2924-2930 (1985).

Maker, H. S. et al., *Biological Abstracts*, 78(2): 1470, No. 12908 (1984) and *Res. Comm. Chem. Pathol. Pharmacol.*, 40(3):355-366 (1983).

Daouk, G. H. et al., *J. Biol. Chem.*, 263(5): 2442-2446 (Feb. 15, 1988).

Lillie, J. W. et al., *Cell*, 50:1091-1100 (1987).

Inhorn, L. et al., *Biological Abstracts*, 82(2): AB-700, No. 17059 (1988) and *Blood*, 71(4):1003-1011 (1988).

Rivedal, E. and T. Sanner, *Chemical Abstracts*, 103(9): 50, No. 153568m (1985) and *Cancer Lett.*, 28(1): 9-17 (1985).

Folbergrova, J. et al., *Biological Abstracts*, 84(2): AB-684, No. 17158 (1987) and *Neoplasma*, 34(1): 3-14 (1987).

Mariman, E. C. M. et al., *Genomics*, 1: 126-137 (1987).

Mariman, E. C. M. et al., *Nucl. Acids Res.*, 17:6385 (1989).

Zerler, B. et al., *Mol. Cell. Biol.*, 7:821-829 (1987).

Shields, R. P. et al., *Lab. Inest.*, 33:151-158 (1975).

McLaughlin, A. C. et al., *J. Biol. Chem.*, 247:4382-4388 (1972).

Kaddurah-Daouk, R. et al., *Mol. Cell Biol.* 10(4): 1476-1483 (1990).

Annesley, T. M. and J. B. Walker, *J. Biol. Chem.*, 253: 8120-8125 (1978).

Whyte, P. et al., *Nature*, 334:124-129 (Jul. 1988).

Ch'ng, J. L. C. et al., *Proc. Natl. Acad. Sci. U.S.A.*, 86:10006-10010 (Dec., 1989).

Colberg-Poley, A. M. and Santomenna, L. D., *Virology*, 166(1):217-228 (1988).

Rowley, G. L. et al., *J. Am. Chem. Soc.*, 93(21):5542-5551 (1971).

Lowe, G. and B. S. Sproat, *J. Biol. Chem.*, 255(9):3944-3951 (1980).

Roberts, J. J. and J. B. Walker, *J. Biol. Chem.*, 260(25):13502-13508 (1985).

FIG. 6A

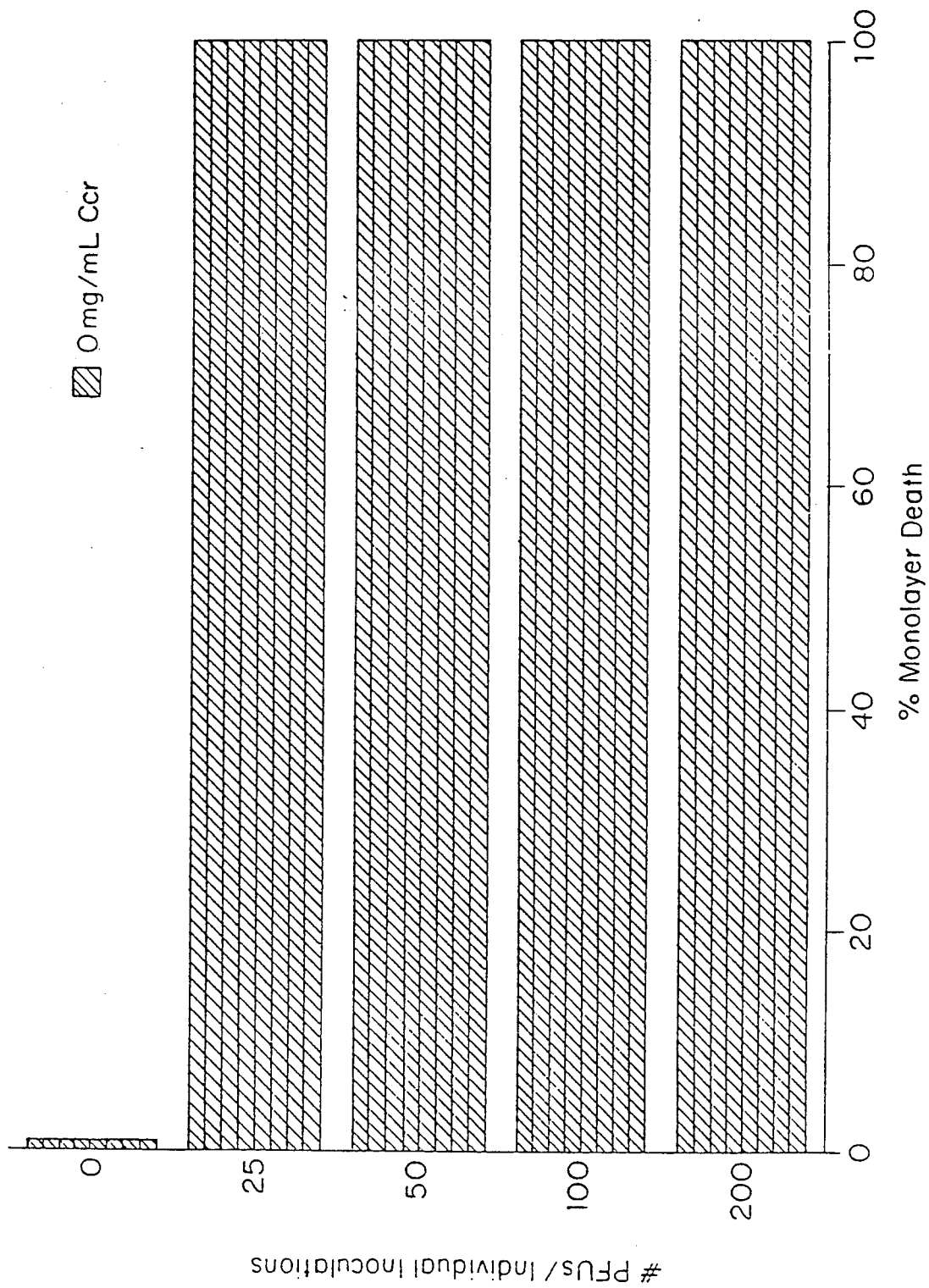

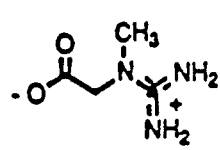
Creatine

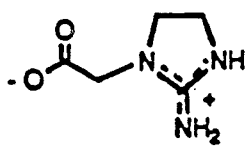
1-carboxymethyl-2-iminoimidazolidine

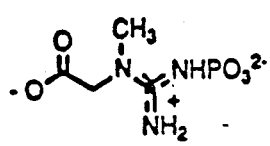
N-phosphoryl creatine

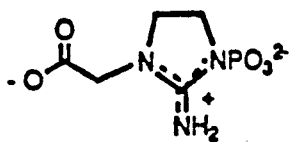
3-Phosphoryl-1-carboxymethyl-2-iminoimidazolidine

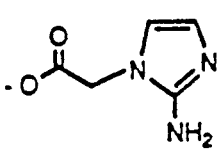
1-carboxymethyl-2-aminoimidazole (I)

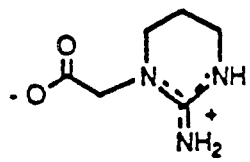
1-carboxymethyl-2-iminohexa-hydropyrimidine (II)

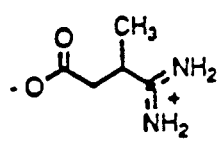
3-amidinobutyric acid (III) "Carbocreatine"

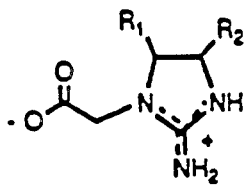
$R_1=CH_3$, $R_2=H$ and $R_2=CH_3$, $R_1=H$
1-carboxymethyl-2-imino-methyl-imidazolidine (AM 361)

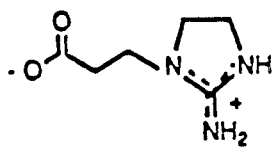
1-carboxyethyl-2-iminoimidazolidine (IV)

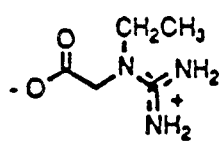
N-ethyl-N-amidino-glycine (V)

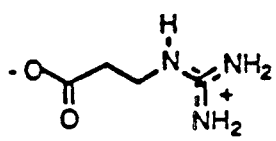
β-guanidino-propionic acid (VI)

FIG. 18

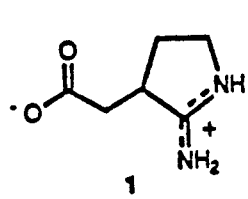
1
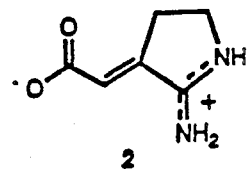
2
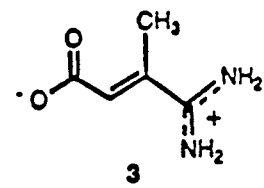
3
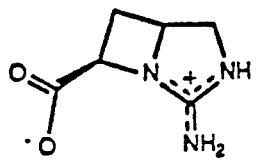
4
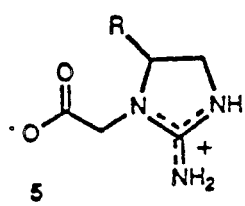
5
R = alkyl or substituted
alkyl group derived from
any amino acid side chain
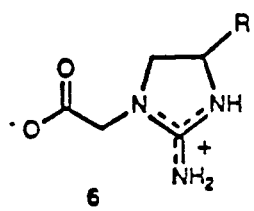
6
R = alkyl or substituted
alkyl group derived from
any amino acid side chain
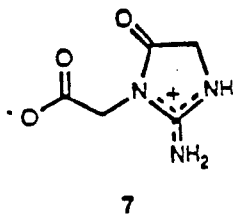
7
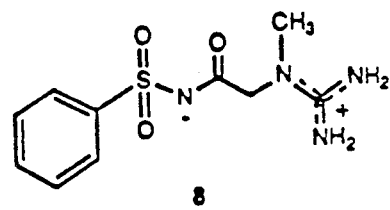
8
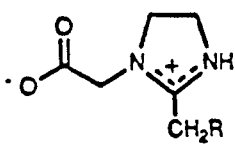
9
R = alkyl or substituted
alkyl group
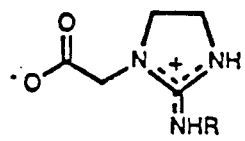
10
R = alkyl or substituted
alkyl group
FIG. 19

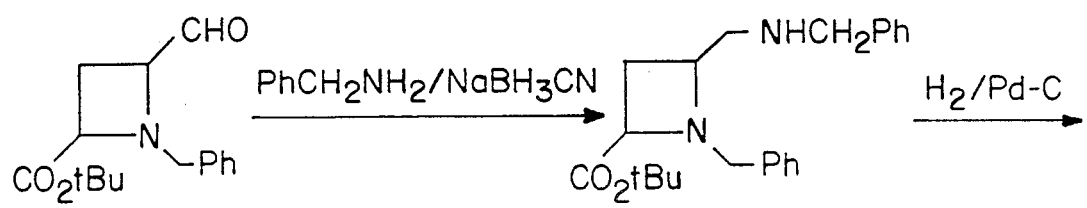
J.E. Baldwin et al., Tetrahedron, 1986, 42:4879-4888, compound 15 therein
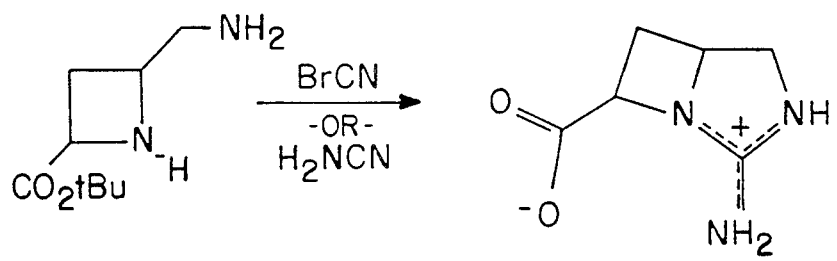
FIG. 21

CREATINE ANALOGS HAVING ANTIVIRAL ACTIVITY

This application is a continuation-in-part of U.S. Ser. No. 07/610,418, filed Nov. 7, 1990, which is a continuation-in-part of U.S. Ser. No. 07/467,147 filed Jan. 18, 1990 and now abandoned, which is a continuation-in-part of U.S. Ser. No. 07/344,963 filed Apr. 28, 1989, now abandoned, which is a continuation-in-part of U.S. Ser. No. 07/310,773 filed Feb. 14, 1989, now abandoned. The contents of U.S. Ser. No. 07/610,418, U.S. Ser. No. 07/467,147, U.S. Ser. No. 07/344,963, and U.S. Ser. No. 07/310,773 are expressly incorporated herein by reference.

BACKGROUND OF THE INVENTION

In natural infections, human viruses normally encounter noncycling, terminally differentiated epithelial cells (J. Tooze, 1981, DNA Tumor Viruses, Cold Spring Harbor Laboratory, Cold Spring Harbor, N.Y.). To maximize the number of cells able to replicate the viral genome and the time spent in viral replication, it is thought that several RNA and DNA tumor viruses alter cell cycle controls (Braithwaite, A. W. et al., *J. Virol.* 45: 192-199 (1983)). Various serotypes of human adenoviruses, for example, induce cellular DNA synthesis by overcoming restriction point controls in the G1 phase of the cell cycle (Shimojo, H. and Yamashita, T., *Virology* 36: 422-433 (1968); Strohl, W. A., *Virology* 39: 653-665 (1969); Younghusband, H. B. et al., *J. Gen Virol.* 45, 455-468 (1979)). This phenomenon has also been observed for other tumor viruses, including simian virus 40 (Gershey, E. L. *J. Virol.* 30: 76-83 (1979)) and Rous sarcoma virus (Kobayashi, N. and A. Kaji, *Proc. Natl. Acad. Sci. U.S.A.* 75: 5501-5505 (1978)).

Adenoviruses also cause alterations in cell cycle progression in growing cells. The G1 phase is shortened in some cells, and DNA replication is uncoupled from the synthesis of rRNA and polyamines. Adenovirus-infected rodent cells prematurely initiate successive rounds of cellular DNA replication and become polyploid (Braithwaite, A. W. et al., *J. Virol.* 45: 192-199 (1983)).

Infection of stationary cells by DNA tumor viruses such as simian virus 40 leads also to the several-fold activation of enzymes in the deoxyribonucleic acid synthetic pathways (Hartwell, L. H. et al., *Virology* 27: 262-272 (1965)). Activation of some of these cellular enzymes in G1-arrested cells may play an important role in viral growth in arrested cells. Such alterations of the physiology of normal cells by the transforming proteins of DNA viruses and other viral proteins might allow more efficient viral replication and production of virus particles.

SUMMARY OF THE INVENTION

The present invention relates to the use of analogs of creatine, such as cyclocreatine, as antiviral agents. Analogs of creatine can be used as antiviral agents against a variety of viruses, particularly DNA viruses. In particular, cyclocreatine displays antiviral activity against Herpes viruses such as HSV-1, HSV-2, human cytomegalovirus, guinea pig cytomegalovirus and Varicella-Zoster virus. In addition, cyclocreatine is an effective antiviral agent against adenovirus. As described herein, cyclocreatine has been shown to be effective in assays of antiviral activity in vitro and in vivo.

As antiviral agents, cyclocreatine or other analogs of creatine can reduce the cytopathic effect of a virus on a cell and inhibit the production of virus. For example, cyclocreatine or other analogs of creatine can be administered to reduce the extent of infection in a cell which would otherwise occur or to prevent infection of a cell, directly or indirectly. Furthermore, cyclocreatine has a synergistic effect when administered with the nucleoside analog acyclovir. Thus, cyclocreatine or other creatine analogs, may be particularly useful when administered in combination with other nucleoside analogs (e.g., acyclovir, ganciclovir, idoxuridine, trifluridine, vidarabine, dideoxyinosine (videx), azidothymidine (zidovudine) or nucleotide analogs, such as foscarnet (phosphonoformic acid) and fosfonet (phosphonoacetic acid).

Creatine analogs such as cyclocreatine can be administered to an individual (e.g., a mammal) alone or in combination with another drug for the treatment or prevention of a viral infection. Cyclocreatine or other creatine analogs can be used to reduce the severity of an infection or reduce symptoms of infection (e.g., a primary infection), or prevent recurrent active infection or reduce the severity of recurrent active infection which does occur, as in HSV infections.

BRIEF DESCRIPTION OF THE DRAWINGS

FIG. 6A is a bar graph depicting the effect of 8 different concentrations of cyclocreatine (bars from top to bottom for each inoculum: 4.0 mg/ml, 3.0 mg/ml, 2.25 mg/ml, 1.69 mg/ml, 1.27 mg/ml, 0.95 mg/ml, 0.71 mg/ml, 0 mg/ml) on the percent of monolayer cell death of DU145 cells inoculated with various amounts of HSV-2 virus. The bar graph illustrates the protective effect of cyclocreatine in DU145 cells against the cytopathic effect of HSV-2 infection.

FIG. 6B is a bar graph depicting the effect of various amounts of HSV-2 virus on percent monolayer death in the absence of drug or cyclocreatine (8 wells/inoculum). The length of each bar represents the percent monolayer death in a single well.

FIG. 18 is an illustration of the structures of some competitive inhibitors of creatine kinase.

FIG. 19 is an illustration of 10 structures, designed to be phosphorylatable creatine analogs.

FIG. 21 is a sample synthetic scheme for the preparation of compound 4 of FIG. 19.

FIG. 23 (top)illustrates a synthetic scheme for making compounds specified by structure 9. FIG. 23 (bottom) illustrates a synthetic scheme for making compounds specified by structure 10.

DETAILED DESCRIPTION OF THE INVENTION

Creatine Kinase

Figure 1A:
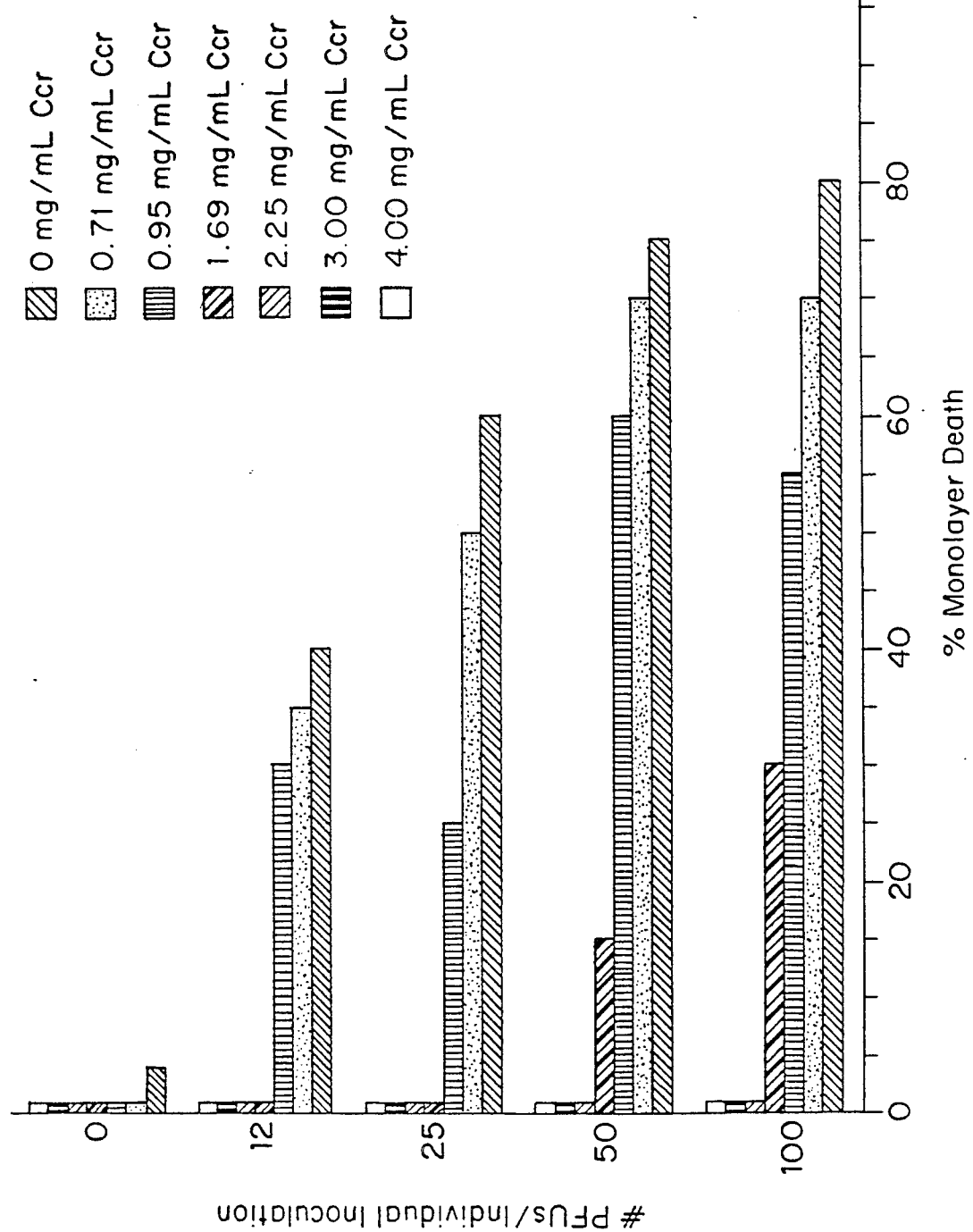
FIG. 1A is a bar graph depicting the effect of 7 different concentrations of cyclocreatine (bars from top to bottom for each inoculum: 4.0 mg/ml, 3.0 mg/ml, 2.25 mg/ml, 1.69 mg/ml, 0.95 mg/ml, 0.71 mg/ml, 0 mg/ml) on the percent of monolayer cell death of Vero cells inoculated with various amounts (plaque forming units, PFUs) of HSV-1 virus. The bar graph illustrates the protective effect of cyclocreatine in Vero cells against the cytopathic effect of HSV-1 infection.

The enzyme ATP: creatine N-phosphotransferase (EC 2.7.3.2; creatine kinase) catalyzes the reversible transfer of a phosphoryl group between ATP and creatine. The product of the forward reaction, creatine phosphate (N-phosphorocreatine), is a vehicle for the transport and storage of energy in brain, muscle, retina (Wallimann et al., *Proc. Natl. Acad. Sci. USA* 83: 3816-3819 (1986)) and spermatozoa (Tombes, R. M. and B. M. Shapiro, *Cell* 41: 325-334, (1985))—all cells with a high energy demand.

Various cytoplasmic CK isozymes participate in a creatine-phosphate shuttle with the mitochondrial creatine kinase isozyme (MiMi) located on the cytoplasmic side of the inner mitochondrial membrane (see references in Biermans et al., *Biochem. Biophys. Acta* 974: 74-80 (1989)). The CK MiMi belongs to a functional multi-enzyme complex together with the ADP/ATP translocase. ATP produced by oxidative phosphorylation is used by mitochondrial creatine kinase to generate creatine phosphate, which is shuttled to cytoplasmic sites of cellular work. ADP generated during the reaction is transported back to the mitochondrial matrix via the ATP/ADP translocase, thus stimulating respiration.

Creatine phosphate carries the phosphoryl group from the mitochondria to regenerate ATP from ADP at specific sites of cellular work. In muscle and heart, the MM isozyme of creatine kinase regenerates ATP at the actin-activated $Mg^{2+}$-ATPase of myosin, the sarcoplasmic $Ca^{2+}$-ATPase and the sarcolemmal $Na^+/K^+$-ATPase. A soluble fraction of the MM isozyme is also thought to be functionally linked to ATP-producing systems of glycolysis. Thus, the phosphocreatine shuttle appears to be a general metabolic feature of tissues with high energy demands.

Interaction of Creatine Kinase and Viruses in Transformation

Creatine kinase BB is one of the cellular enzymes induced by DNA tumor viruses, including adenovirus, human cytomegalovirus and Epstein-Barr virus (EBV). The adenoviral product required for induction of the CK-B gene is the E1a protein. The regions of this protein required for activation of CK are also required for transformation of nonpermissive cells, suggesting that activation of CK may play a role in the cell cycle alterations that lead to viral transformation. CK-B is also induced by human cytomegalovirus. Like adenovirus infection, CMV infection is associated with stimulation of cellular macromolecular synthesis and increased mitotic activity.

The discovery of the induction of expression of the CK gene by the adenovirus E1a oncogenic product stemmed from the cloning and sequencing of the gene encoding the CK-B subunit. The CK-B gene was found to contain striking DNA sequence similarity to the E2 gene of adenovirus, a gene which is activated by the adenovirus E1a protein and which encodes a 72 kD DNA binding protein involved in replication. The DNA sequence similarity between a region upstream of the start site of transcription of CK-B to sequences upstream of the start site of transcription of the E2 gene of adenovirus suggested that these similar sequences might be important transcription regulatory elements of the two genes and that they could mediate induction by the E1a protein. The potential coregulation of viral and cellular genes by a single product would be economic and suggests that CK could be important in viral transformation or replication. It was subsequently shown that the E1A gene product induces the expression of the CK-B gene, providing a link between transformation and induction of gene expression. Consistent with a possible role for CK-B in oncogenesis, a number of creatine analogs were shown to have antitumor activity.

A Role for Creatine Kinase in Viral Functions

The transforming or cell activation potential of a DNA tumor virus can be viewed as a manifestation of the ability of the virus to replicate in non-cycling normal host cells. It was postulated that the induction of CK-B by tumor viruses might enhance the efficiency of viral replication in certain non-dividing host cells. Other viruses might similarly depend on creatine kinase for viral processes. Efficient viral production is an energy-demanding process that requires redirection of cellular metabolites. Although the mechanisms by which cellular metabolites are normally directed to specific cellular tasks is poorly understood, it is thought that cells regulate the rate of energy production in response to demand, and that creatine kinase plays a key role in the allocation of high energy phosphate to many diverse processes, such as biosynthesis, cell movement and mitosis. Because the biosynthesis of progeny virions requires significant energy and because creatine kinase plays an important role in controlling the flow of energy inside the cell, the induction by viruses of creatine kinase, and of the BB isozyme in particular, might facilitate the generation and release of cellular energy reserves required for stages of virion replication and production.

If the induction of creatine kinase is important for efficient replication of virus or other vital functions, then inhibition of CK or interference with the normal activity of CK may block the production of progeny virus. Another possibility is that creatine kinase activity generates a product which affects a cellular protein required for viral function or a viral protein. For example, creatine phosphate may donate a phosphate to a protein to modify its function (e.g., activity, location). If phosphocreatine is such a phosphate donor, creatine analogs which are phosphorylatable or phosphocreatine analogs may competitively inhibit the interaction of phosphocreatine with a target protein thereby directly or indirectly interfering with viral functions. Alternatively, phosphorylatable creatine analogs with altered phosphoryl group transfer potential may tie up phosphate stores preventing efficient transfer of phosphate to targets.

Ingestion of creatine analogs has been shown to result in replacement of tissue P-creatine pools by synthetic phosphagens with different kinetic and thermodynamic properties. This results in subtle changes of intracellular energy metabolism, including the increase of total reserves of high energy phosphate (see refs. Roberts, J. J. and J. B. Walker, *Arch. Biochem. Biophys.* 220(2): 563-571 (1983)). The replacement of P-creatine pools with slower-acting synthetic phosphagens, such as creatine analogs, might inhibit the production of progeny virions. One such analog, cyclocreatine (1-carboxymethyl-2-aminoimidazolidine) perturbs the flow of energy of cells in stress and may interfere with ATP utilization at sites of cellular work. Therefore, a creatine analog, cyclocreatine, was selected as a candidate antiviral agent.

Cyclocreatine

Cyclocreatine is an essentially planar cyclic analog of creatine. Although cyclocreatine is structurally similar to creatine, the two compounds are distinguishable both kinetically and thermodynamically. Cyclocreatine is phosphorylated efficiently by creatine kinase in the forward reaction both in vitro and in vivo. In the reverse reaction, however, cyclocreatine phosphate (N-phosphorocyclocreatine, P-cyclocreatine) is dephosphorylated relatively slowly. The initial rate of phosphorylation of cyclocreatine by creating kinase in vitro is 31% of that of creatine (Rowley, G. L., *J. Am. Chem. Soc.* 93: 5542-5551 (1971)). Vmax measured at 1° C. for cyclocreatine is 90% of that of creatine, and the Km has been determined to be 25 mM, 5 fold higher than that of creatine. Therefore, under these conditions in vitro, the Vmax/Km ratio for cyclocreatine in the forward reaction is approximately one-fifth that of creatine (McLaughlin, A. C. et al., *J. Biol. Chem.* 247, 4382-4388 (1972)).

The phosphorylated compound P-cyclocreatine is structurally similar to phosphocreatine; however, the phosphorous-nitrogen (P-N) bond of cyclocreatine phosphate is more stable than that of phosphocreatine. P-cyclocreatine has a Gibbs free energy of hydrolysis approximately 2 kcal/mol lower than that of P-creatine and ~1 kcal/mol higher than that of ATP. As a result, at equilibrium the ratio of cyclocreatine phosphate to cyclocreatine is approximately 30 times the ratio of phosphocreatine to creatine (LoPresti, P. and M. Cohn, *Biochem. Biophys. Acta* 998: 317-320 (1989)). At pH 7 (37° C.), in the reverse reaction catalyzed by creatine kinase, the Vmax/Km ratio for P-cyclocreatine is approximately 160-fold lower than for P-creatine (Annesley, T. M. and J. B. Walker, *J. Biol. Chem.* 253: 8120-8125, (1978); Annesley, T. M. and J. B. Walker, *Biochem. Biophys. Res. Commun.* 74: 185-190 (1977)) .

Cyclocreatine was found to be a competitive inhibitor of P-creatine for the reverse reaction at 1° C. ($K_i=44$ mM) (A. C. McLaughlin et al., *J. Biol. Chem.* 247: 4382-4388 (1972)). In the presence of 80 mM cyclocreatine, the Km of P-creatine is increased from 1.8 mM to 5.1 mM.

Antiviral Activity of Creatine Analogs

The present invention relates to the use of creatine analogs such as cyclocreatine as antiviral agents. Creatine analogs such as cyclocreatine can be used as antiviral agents against a variety of viruses, particularly DNA viruses. In particular, cyclocreatine has been shown to be an effective antiviral agent against Herpes viruses, such as HSV-1, HSV-2, human cytomegalovirus, guinea pig cytomegalovirus and Varicella-Zoster virus. In addition, cyclocreatine is an effective antiviral agent against adenovirus.

As shown in Example 1, cyclocreatine reduces the cytopathic effects of Herpes Simplex Virus Type 1 and Type 2 in Vero cells in culture (FIGS. 1 and 2). The results shown in FIGS. 3-8 indicate that the protective effect of cyclocreatine against HSV-1 and HSV-2 is not specific to Vero cells. The results of an assay of plaquing efficiency of HSV-1 confirmed these observations in another assay format (Example 2, FIG. 9). Thus, cyclocreatine and other creatine analogs can be used to inhibit (i.e., reduce or eliminate) cytopathic effects of a virus on a cell upon contacting the cell with cyclocreatine.

The antiviral activity of cyclocreatine was also tested in vivo in the treatment of HSV-2 vaginitis (Example 3). The results of one such study are recorded in FIG. 10 and Table 1, which indicate that a cream formulation containing 10% cyclocreatine reduced the average lesion score (the severity of genital lesions) as compared to the placebo. Toxicity controls indicated that the drug was well-tolerated at this dosage and caused no adverse effects to the area of application. Additional experiments discussed in Example 3 using the mouse vaginitis model (Tables 2A and 2B, and FIG. 11), are consistent with an antiviral effect of cyclocreatine in vivo and an additive effect of cyclocreatine with acyclovir.

Cyclocreatine was also effective against strains of human and guinea pig cytomegalovirus, Varicella-Zoster virus, and adenovirus (Example 5) in vitro. The cytotoxic effects due to the drug were slight under the conditions used in these experiments. Weak antiviral activity against murine cytomegalovirus, Influenza B and Parainfluenza type 3 virus was also observed under the conditions used, suggesting the possibility of antiviral activity against other DNA and RNA viruses. Under the conditions used to assay antiviral activity, cyclocreatine did not display significant antiviral activity against Vesicular Stomatitis virus, Pseudorabies virus or Influenza A virus.

Treatment with cyclocreatine can provide a useful alternative antiviral therapy for treatment of infections which prove resistant to other antiviral agents, such as the anti-Herpes agents ganciclovir (DHPG, dihydroxypropoxymethylguanine) and acyclovir. One particular ganciclovir (DHPG) resistant human cytomegalovirus (HCMV) strain (HCMV, strain C8704) did not display a similar resistance to cyclocreatine, suggesting that cyclocreatine operates via a mechanism distinct from that of DHPG. In addition, cyclocreatine activity against an acyclovir resistant, thymidine kinase negative (TK−) HSV-1 strain was comparable to activity against TK+ strains. The viral TK converts the nucleoside analog acyclovir into acyclovir monophosphate, a nucleotide analog, potentiating the antiviral activity of acyclovir. Cyclocreatine antiviral activity apparently does not depend on this TK-mediated step.

In contrast, preliminary studies indicate that creatine kinase activity (e.g., CK-B) may potentiate the antiviral activity of a class of antiviral compounds with selected properties similar to cyclocreatine. Cyclocreatine is the dihydro analog of 1-carboxymethyl-2-aminoimidazole. Despite this structural similarity, 1-carboxymethyl-2-aminoimidazole is a poor substrate for creatine kinase. This analog has a binding constant for creatine kinase similar to that of creatine and cyclocreatine, but the initial rate of phosphorylation is 5 orders of magnitude slower. In the reverse reaction, the phosphorylated analog is also a poor substrate (Lowe, G. and B. S. Sproat, *J. Biol. Chem.* 255: 3944-3951, (1980)). As shown in Example 6, 1-carboxymethyl-2-aminoimidazole did not display a comparable antiviral effect under the conditions of the cytopathogencity effect assay (FIG. 16). Therefore, transfer of a phosphate group to cyclocreatine and/or other creatine analogs may be important for the antiviral activity of these compounds.

The invention further relates to analogs of creatine having antiviral activity. As antiviral agents, cyclocreatine or other analogs of creatine can inhibit the production of virus and reduce the cytopathic effect of a virus on a cell. The properties of useful creatine analogs are described in more detail below. As used herein and further described below, the analogs of creatine (creatine analogs) are (1) structural analogs of creatine or N-phosphorocreatine or (2) comprise structural analogs of creatine or N-phosphorocreatine (e.g., bisubstrate analogs).

Related Antiviral Agents

Four classes of creatine analogs selected as candidate antiviral compounds are described below: (1) creatine analogs that can be phosphorylated by creatine kinase but differ in their phosphoryl group transfer potential, (2) bisubstrate inhibitors of creatine kinase comprising covalently linked structural analogs of adenosine triphosphate (ATP) and creatine, (3) creatine analogs which can act as irreversible inhibitors of creatine kinase, and (4) N-phosphorocreatine analogs bearing nontransferable moieties which mimic the N-phosphoryl group. Compounds with the properties of these candidate antiviral agents can be tested for antiviral activity against viruses, such as Herpesviruses, adenoviruses or other viruses using known assay techniques, such as the cytopathic effect assay procedure or plaque reduction assay procedure described in the Examples.

(1) Creatine Analogs Phosphorylatable by Creatine Kinase

A number of competitive inhibitors of creatine kinase were analyzed for antiviral activity. FIG. 18 illustrates the structures of creatine, cyclocreatine (1-carboxymethyl-2-iminoimidazolidine), N-phosphorocreatine (N-phosphoryl creatine), cyclocreatine phosphate (3-phosphoryl-1-carboxymethyl-2-iminoimidazolidine) and of seven other compounds which were tested for antiviral activity (compounds I-VI and AM 361, FIG. 18). In particular, 1-carboxymethyl-2-aminoimidazole (I, Example 6), 1-carboxymethyl-2-iminohexahydropyrimidine (II, Example 10), 3-amidinobutyric acid (III, carbocreatine, Example 10), 1-carboxymethyl-2-iminomethylimidazolidine (AM361, Example 7), 1-carboxyethyl-2-iminoimidazolidine (IV, homocyclocreatine, Example 10), N-ethyl-N-amidinoglycine (V, EGA, Example 10), and β-guanidinopropionic acid (VI, Example 10) were tested. Although each compound displayed some antiviral activity under the conditions of the assay, none of the seven compounds displayed activity comparable to the creatine kinase inhibitor cyclocreatine. These observations suggested that the advantageous combination of kinetic viability as a substrate for creatine kinase and a phosphoryl group transfer potential between that of N-phosphorocreatine and adenosine triphosphate possessed by the phosphorylated form of cyclocreatine may explain the antiviral activity of cyclocreatine.

Therefore, cyclocreatine (AM 285, 1-carboxymethyl-2-iminoimidazolidine) was selected as the prototype of a class of competitive inhibitors of creatine kinase, which as substrate analogs, can be phosphorylated by creatine kinase (e.g., CKBB, CKMM). Creatine analogs which are predicted to be kinetically viable substrates for creatine kinase have been designed. A selection of 10 types of candidate antiviral creatine analogs is illustrated in FIG. 19. Each of these phosphorylatable substrate analogs was designed to maintain structural elements thought to be essential for efficient binding to and phosphorylation by creatine kinase.

A "kinetically viable substrate" should, at a minimum, possess a substrate activity in the forward reaction (phosphorylation reaction) catalyzed by creatine kinase which is equal to or greater than that of homocyclocreatine (1-carboxyethyl-2-iminoimidazolidine), a compound which has some antiviral activity and has similar thermodynamic properties to cyclocreatine, but is approximately $1 \times 10^{-4}$ as active a substrate as creatine in the forward reaction (Roberts, J. J. and J. B.

Walker, *Arch. Biochem. Biophys.* 220(2): 563–571 (1983)). Thus, additional phosphorylatable creatine analogs are deemed to be "kinetically viable" if they are phosphorylated in vitro by creatine kinase at a rate greater than or equal to that of homocyclocreatine under a selected set of conditions.

In addition to its properties as an efficient substrate for phosphorylation by creatine kinase, the $\Delta G^{o'}$ of hydrolysis of the N-phosphoryl group of cyclocreatine phosphate (3-phosphoryl-1-carboxymethyl-2-iminoimidazolidine) is approximately 2 kcal/mole below that of N-phosphorocreatine and about 1 kcal/mole above that of adenosine triphosphate. The additional creatine analogs shown in FIG. 19 are also selected or designed so that the in vivo phosphorylated form is predicted to have a free energy of phosphoryl group hydrolysis (a phosphoryl group transfer potential) which falls in the range from that of N-phosphorocreatine to that of ATP, inclusive.

Compounds 1 and 2

For example, cyclic compounds 1 and 2 shown in FIG. 19 are related to cyclocreatine by substitution of the tertiary $sp^2$ nitrogen with $sp^3$ or $sp^2$ hybridized carbons, respectively. In compound 1, this substitution allows the ring to adopt a less planar conformation and is expected to lower the $pK_a$ of the terminal nitrogen, lowering the phosphoryl group transfer potential of the molecule.

Substitution of the $sp^2$ nitrogen of cyclocreatine with an $sp^2$ hybridized carbon gives compound 2 (FIG. 19), resulting in a fully planar and conjugated molecule, and further lowers the $pK_a$ of the terminal nitrogen below that of compound 1. The dependence of carboxylic acid side chain orientation on substrate binding can be investigated by comparing the binding activity of compounds 1 and 2.

Figure 20:
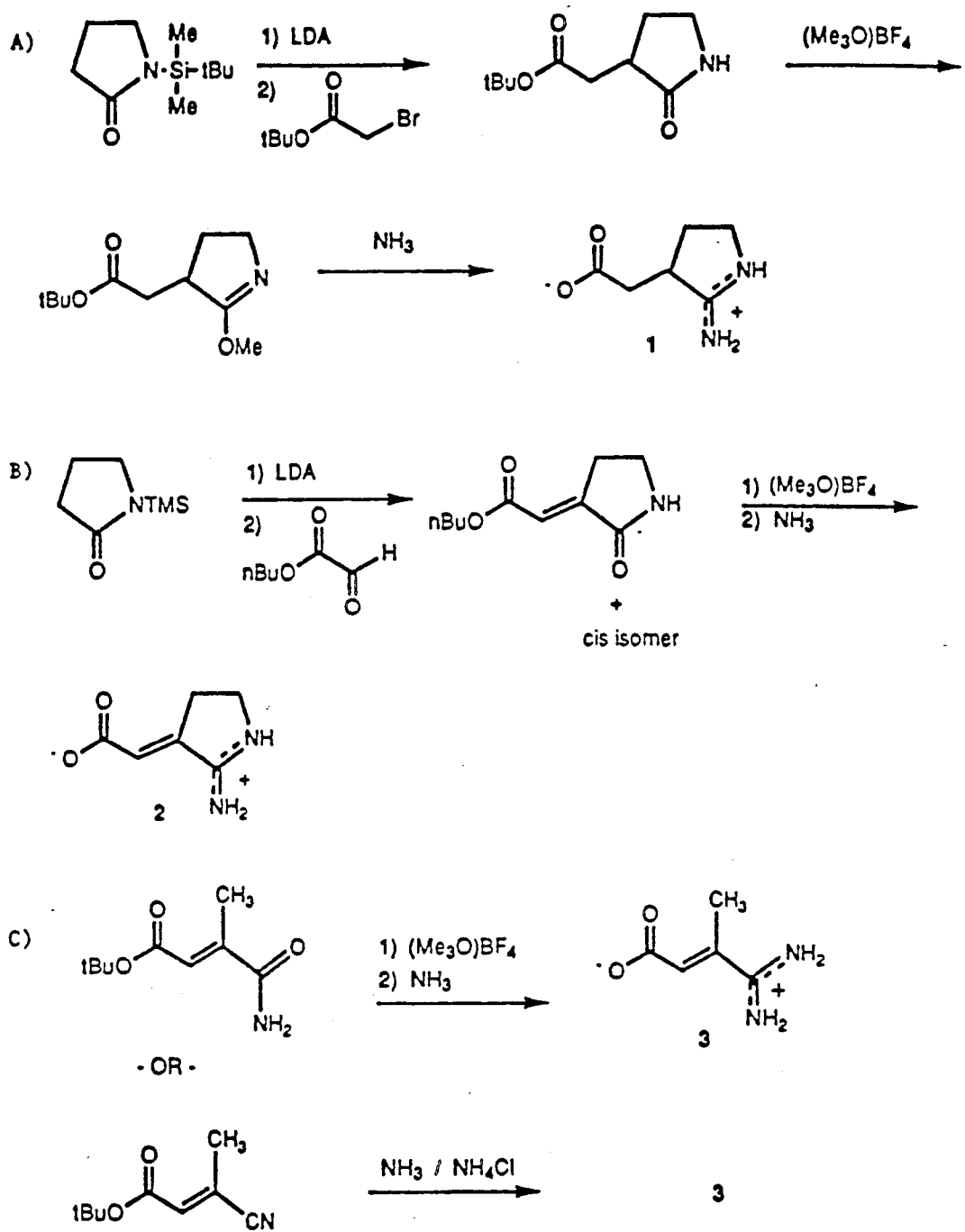
FIG. 20A is a sample synthetic scheme for the preparation of compound 1 of FIG. 19.
FIG. 20B is a sample synthetic scheme for the preparation of compound 2 of FIG. 19.
FIG. 20C is a sample synthetic scheme for the preparation of compound 3 of FIG. 19.

As illustrated in FIGS. 20A and B, compounds 1 and 2 can be synthesized in four steps from N-tertbutyldimethylsilyl-2-pyrrolidinone or N-trimethylsilyl-2-pyrrolidinone, respectively. In addition, hydrogenation of the intermediates obtained in preparing compound 2 (FIG. 20B), followed by the subsequent steps shown in FIG. 20B ((1) $(Me_3O)BF_4$; (2) $NH_3$) can yield compound 1.

Compound 3

The acyclic analog designated compound 3 (FIG. 19) is expected to have physico-chemical properties similar to those of compound 2; however, the $pK_a$ of the amidino nitrogens should be higher. As shown in FIG. 20C, compound 3 can be prepared by amidination of a known nitrile, such as one described in *Collect. Czech. Chem. Commun.* 41: 2034 (1976)) or a derived amide.

Compound 4

The conformationally restricted bicyclic analog designated as compound 4 (FIG. 19) has been previously proposed as a potential competitive inhibitor of creatine kinase (Dietrich, R. F. and G. L. Kenyon, *Bioorganic Chemistry* 12: 221–228 (1984)). This compound is expected to serve as a tight binding (i.e., having a relative $K_i$ which is less than or equal to the $K_m$ of creatine), phosphorylatable substrate analog for creatine kinase. The restriction of conformational degrees of freedom should decrease unfavorable active-site contacts and minimize the conformational changes required for substrate binding and/or reactivity.

As shown in FIG. 21, the known azetidine aldehyde, which is itself derived from $\alpha,\alpha'$-dibromoglutaric anhydride as described by Baldwin et al. (Baldwin, J. E. et al., *Tetrahedron*, 42: 4879–4888 (1986)), can serve as an intermediate in the preparation of compound 4. Reductive amination of the azetidine aldehyde (compound 15 described by Baldwin, J. E. et al., *Tetrahedron*, 42: 4879–4888 (1986)), with benzylamine can provide the protected diamine. Hydrogenolysis of the protected diamine, followed by cyclization with either cyanogen bromide or cyanamide, and concomitant ester hydrolysis can yield compound 4.

Structures 5 and 6 and Related Analogs

Structures 5 and 6 (FIG. 19) differ from cyclocreatine by the addition of a substituent (R) to the 5-membered ring. This substitution is designed to enhance the energetics of substrate binding relative to cyclocreatine by establishing and exploiting additional contact sites, while allowing phosphoryl group transfer to occur.

In compounds specified by structures 5 and 6, R can be an alkyl group or substituted alkyl group derived from the side chain of an $\alpha$-amino acid, including, but not necessarily limited to, one of the 20 standard amino acids. As used herein, the term "alkyl" refers to branched or straight chain hydrocarbon groups having one or more carbon atoms. In addition, as used herein, "substituted alkyl group" refers to "alkyl" groups as defined above, which in addition, bear one or more functionalities, including but not limited to unsaturation, heteroatom-substituents, carboxylic and inorganic acid derivatives, and electrophilic moieties.

Figure 22:
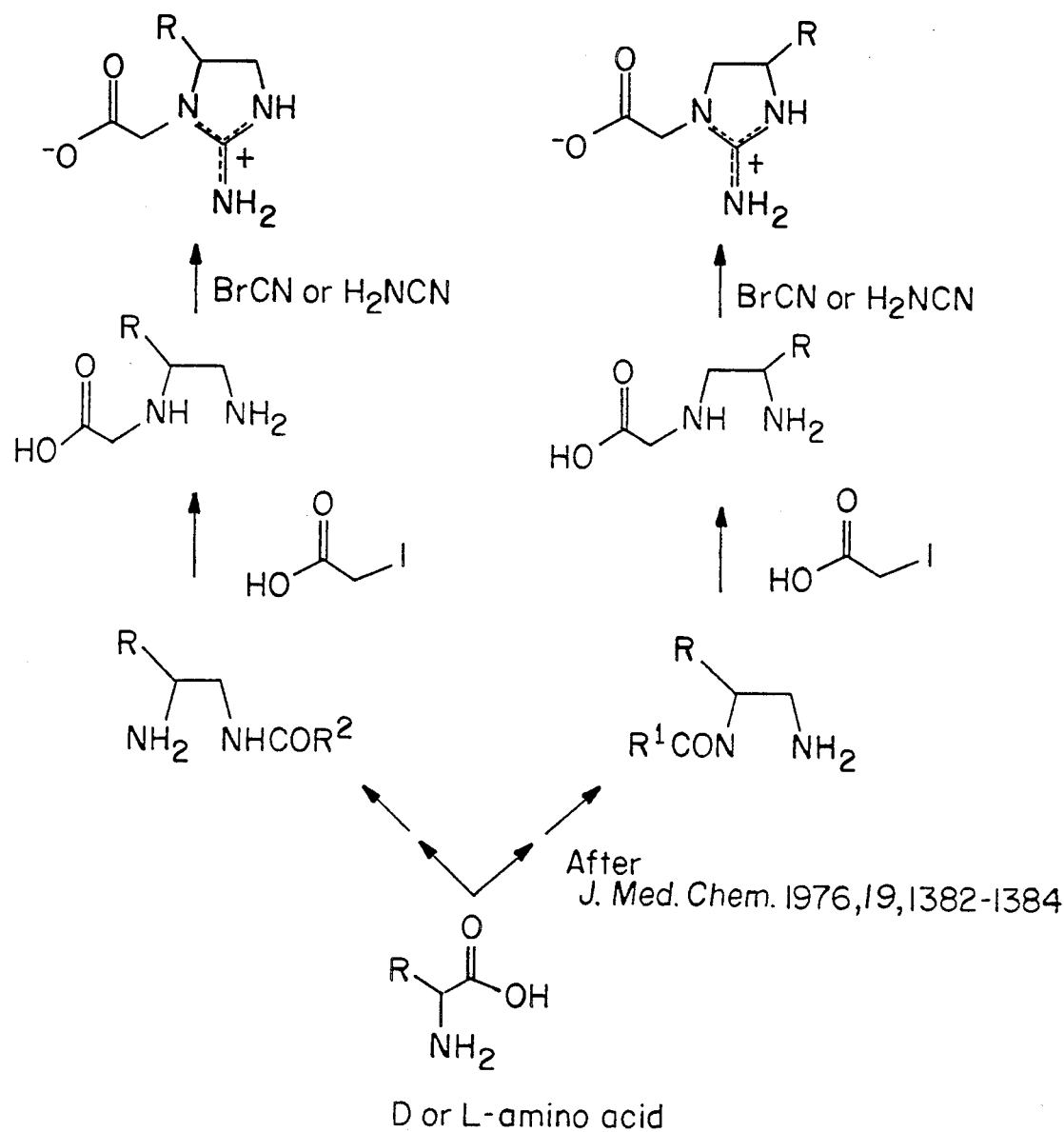
FIG. 22 is a pair of synthetic schemes illustrating general methods for the synthesis of compounds specified by structures 5 and 6 of FIG. 19.

A unified approach to the synthesis of ring-substituted derivatives of cyclcocreatine bearing a wide variety of R-groups in either absolute configuration and incorporating either hydrophobic or hydrophilic subsitutents, such as compounds specified by structures 5 and 6, relies upon the incorporation of differentially protected 1,2-diamines by methods such as those described in FIG. 22. Such 1,2-diamines can be derived from $\alpha$-amino acids, as for example by the procedure outlined for the conversion of alanine to optically active 1,2-diaminopropane (Miller, D. D. et al., *J. Med. Chem.* 19: 1382–1384 (1976)). This procedure can be adapted to different $\alpha$-amino acids. Alternatively, alkylation of glycine aldimine (*Synthesis*, pp. 313–315 (1984); *Tet. Lett.* 23(41): 4256–4258 (1982)) can provide additional 1,2-diamine intermediates bearing other alkyl or substituted alkyl side chains. It is understood that when a selected synthetic method does not rely on an $\alpha$-amino acid as an R group donor, the nature of alkyl and substituted alkyl groups is not changed; in that case, "alkyl" refers to branched or straight chain hydrocarbon groups having one or more carbon atoms, and "substituted alkyl group" refers to an alkyl group as defined bearing one or more functionalities, including but not limited to unsaturation, heteroatom-substituents, carboxylic and inorganic acid derivatives, and electrophilic moieties.

AM 361 is a preparation comprising a mixture of compounds represented by structures 5 and 6 wherein R=methyl. This preparation displayed antiviral activity against HSV-1 in the cytopathic effect assay format (FIG. 17, Example 7).

Compound 7

Compound 7 of FIG. 19 can be prepared by a one-step condensation of glycylglycine with cyanamide as described in Example 8. Compound 7 was tested in parallel to AM 361 (compound 5/6) in the cytopathic effect assay against HSV-1. At the highest concentration tested (41.7 mM), compound 7 consistently showed antiviral activity, reducing monolayer death in all 5 vital inoculla tested. Slight cytotoxicity was observed at this concentration. Further experiments are required to establish the significance of the antiviral effect.

Compound 8

Compound 8 shown in FIG. 19 is a sulfonamide derivative of creatine and is designed to enhance potential binding contacts in the vicinity of the creatine carboxylate binding region of creatine kinase. Amidination of the arylsulfonamide derivative of N-methyl glycine with methylthiouronium iodide (*J. Med. Chem.* 23: 1232-1235 (1980)) can result in the production of compound 8.

Structures 9 and 10 and Related Analogs

Two additional types of cyclic creatine analogs are the amidines and trisubstituted guanidines represented by structures 9 and 10, respectively. R in compound 9- and 10-type structures is an alkyl or substituted alkyl. "Alkyl" refers to branched or straight chain hydrocarbon groups having one or more carbon atoms, and "substituted alkyl group" refers to an alkyl group as defined bearing one or more functionalities, including but not limited to unsaturation, heteroatom-substituents, carboxylic and inorganic acid derivatives, and electrophilic moieties.

Figure 23:
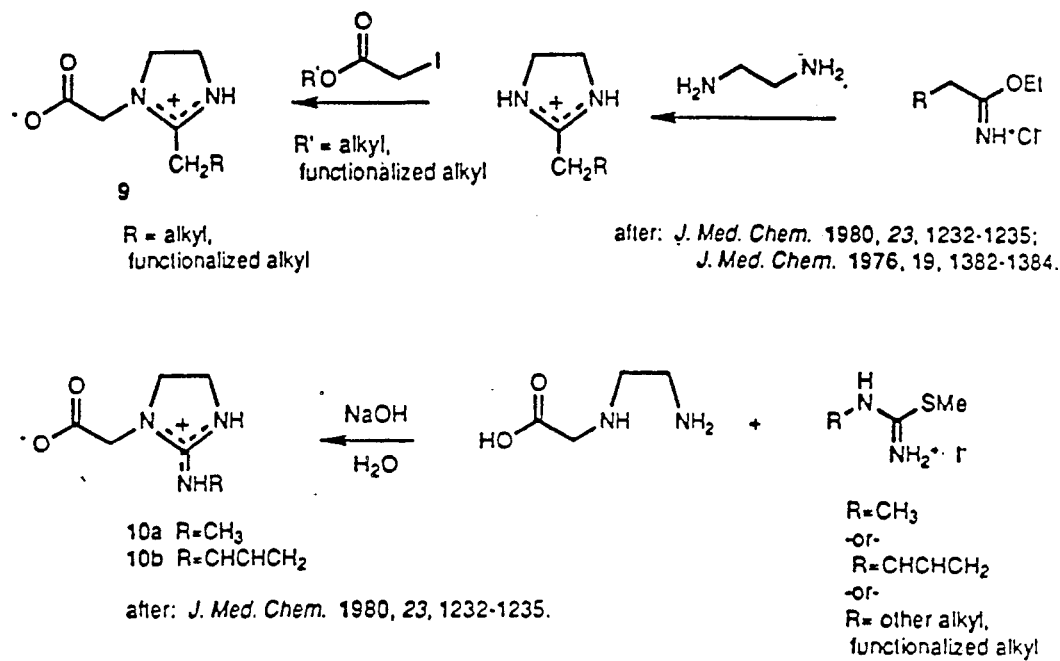
FIG. 23 is a pair of synthetic schemes illustrating methods for making compounds specified by structures 9 and 10 of FIG. 19.

As indicated in FIG. 23 (top), the preparation of variously substituted (alkyl and substituted alkyl) cyclic amidine precursors to compound 9 structures (intermediate structures in FIG. 23, top) are modeled after the preparation of acetamidine hydrochloride (*Org. Synth. Coll.* Vol. I, p. 5) and ethylenediamine as described in *J. Med. Chem.* 23: 1232-1235 (1980) and references therein. Carboxymethylation of five-membered cyclic amidine precursors with iodoacetate or R'OCOCH$_2$I, as indicated in FIG. 23, can lead to compounds specified by structure 9. This approach has precedent in the preparation of tolazoline acetic acid (structure 9, where R=phenyl) by condensation of tolazoline with iodoacetic acid (Nguyen, Ann Cae Khue, Ph.D. dissertation in Pharmaceutical Chemistry, 1983, University of California, San Francisco, pp. 37-38).

An approach to the synthesis of compounds specified by structure 10 involves the condensation of ethylene diamine acetic acid with N-substituted thiouronium salts (after *J. Med. Chem.* 23: 1232-1235 (1980)). The thiouronium salts can be prepared according to established procedures (Rowley, et al., *J. Am. Chem. Soc.* 93: 5542-5551 (1971), Curd et al., *J. Chem. Soc.* 1742 (1949). For instance, compounds 10a and 10b, described in Example 9 (structure 10, where R=methyl or R=allyl, respectively), were prepared by this method. A description of initial experiments assaying the antiviral activity of these compounds is provided in Example 9.

(2) Bi-substrate Inhibitors of Creatine Kinase

A second class of creatine kinase targeted compounds are bi-substrate analogs comprising an adenosine-like moiety linked via a modifiable bridge to a creatine-like moiety (i.e., creatine or a creatine analog). Such compounds are expected to bind with greater affinity than the sum of the binding interactions of each individual substrate (e.g., creatine and ATP). The modifiable bridge linking an adenosine-like moiety at the 5'-carbon to a creatine-like moiety can be a carbonyl group, alkyl (a branched or straight chain hydrocarbon group having one or more carbon atoms), or substituted alkyl group (an alkyl group bearing one or more functionalities, including but not limited to unsaturation, heteroatom-substituents, carboxylic and inorganic acid derivatives, and electrophilic moieties).

Figure 24:
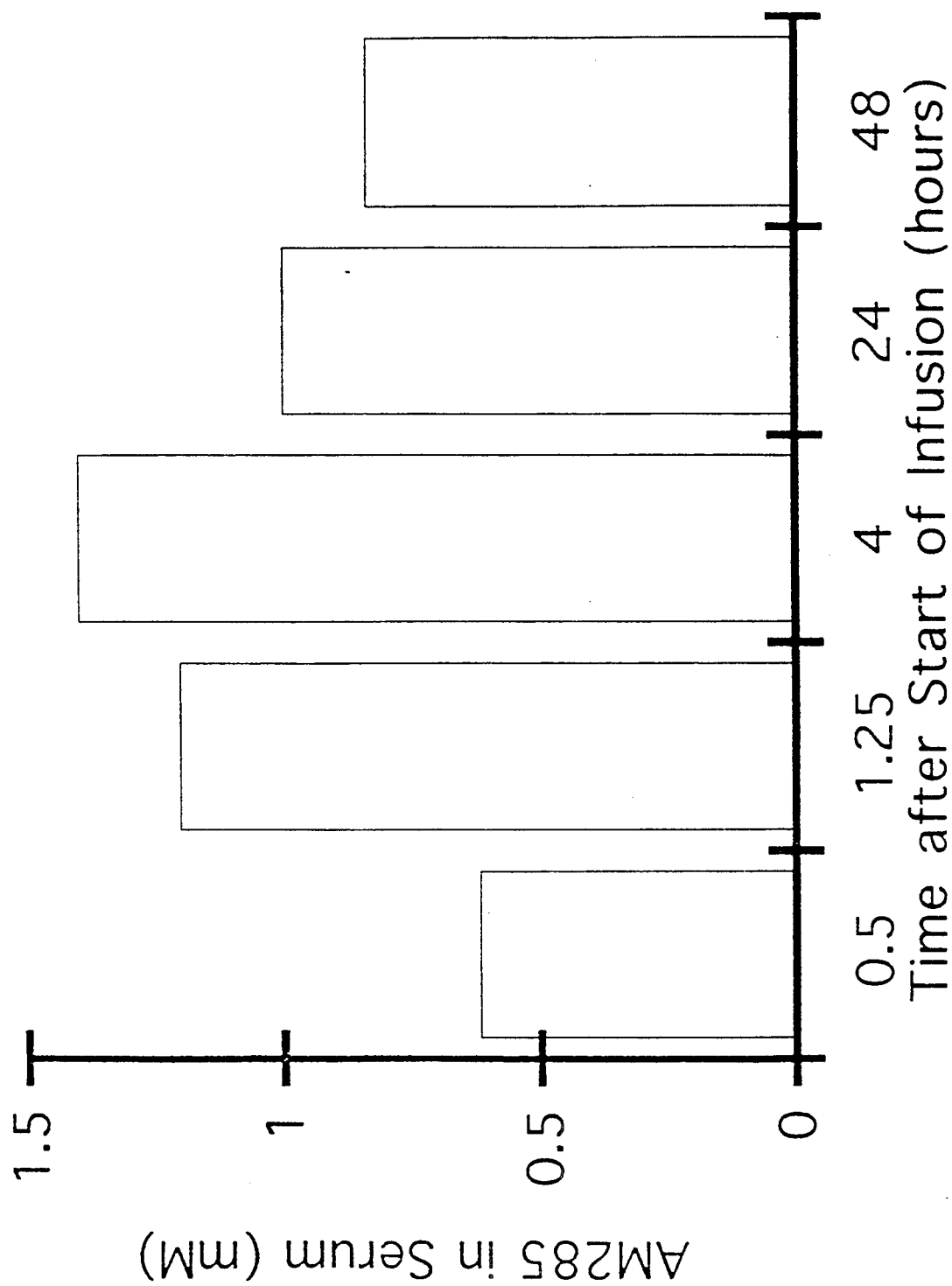
FIG. 24 illustrates the structures of potential bi-substrate analogs (structure 11), irreversible inhibitors of creatine kinase (compounds 12-15), and N-phosphorocreatine analogs having a small phosphate-like group transfer ability or no phosphate-like group transfer ability (compounds 16-20).

For instance, compound 11 represents a simple prototypic bi-substrate analog for creatine kinase (FIG. 24). In compound 11, creatine has been linked to adenosine though a methylene bridge of 4-7 carbons in length. Polar and charged groups can be incorporated into the bridge between the adenosine-like and creatine-like moieties. For example, simple dicarboxylic acids of 4-7 carbons can serve to link the creatine moiety as an amide to the adenosine as an ester. The effects of incorporating such polar and charged groups into the tether on antiviral activity can be ascertained using assays such as the cytopathogenicity effect or plaque reduction assays described in the Examples. Analogs of creatine such as the phosphorylatable creatine analogs described above can also be incorporated into the bi-substrate inhibitors as the creatine-like moiety.

(3) Creatine Analogs As Irreversible Inhibitors of Creatine Kinase

A third class of potential antiviral compounds is designed to inhibit creatine kinase. The analogs of creatine in this class can bind irreversibly to the active site of the enzyme. Two such affinity reagents that have previously been shown to completely and irreversibly inactivate creatine kinase are epoxycreatine (compound 12, FIG. 24; Marietta, M. A. and G. L. Kenyon, *J. Biol. Chem.* 254: 1879-1886 (1979)) and isoepoxycreatine (compound 13, FIG. 24; Nguyen, A.C.K., Ph.D. dissertation in Pharmaceutical Chemistry, (University of California, San Francisco, 1983), pp. 112-205). At a saturating concentration (335 mM at 0° C.), epoxycreatine undergoes approximately 15 turnovers per inactivating event. These affinity reagents indicate that substrate analogs bearing electrophilic moieties can act as active site-directed competitive and irreversible inhibitors of creatine kinase.

There are several approaches to enhancing the specificity and hence, the efficacy of active site-targeted irreversible inhibitors of creatine kinase incorporating an electrophilic moiety. First, the effective concentration of compound required for inhibition can be lowered by increasing favorable and decreasing unfavorable binding contacts in the creatine analogs as described above for compounds 1-10 (FIG. 19). Thus, the incorporation of electrophilic moieties such as an epoxide or an aziridine moiety into compounds specified by structures 1-10 (FIG. 19), which are designed to bind creatine kinase, can provide active site-targeted irreversible inhibitors of creatine kinase bearing electrophilic moieties with enhanced specificity relative to compounds 12 and 13. For example, an electrophilic moiety can be incorporated in the R groups of compounds represented by structures 5, 6, 9, and 10 (FIG. 19), or into the α-carboxylate carbon of compounds represented by structures 1, 5, 6, 7, 8, 9, and 10 (FIG. 19). These and other derivatives of compounds specified by structures 1-10 bearing electrophilic moieties (e.g., epoxide, aziridine, and Michael-type acceptors such as acrylic acid derivatives), can be obtained by simple modification of the synthetic routes described above.

Note that compounds 2 and 3 (FIG. 19) bear α,β-unsaturated carboxylates which are possibly sufficiently active Michael-type acceptors to react with creatine kinase active site nucleophilic moieties as irreversible inhibitors. Thus, these compounds may be similar to compound 12, which is a "kinetically viable" substrate and is an irreversible inhibitor after approximately 15 turnovers.

Secondly, such creatine analogs bearing electrophilic moieties can be incorporated into the bi-substrate analogs described above in place of the creatine-like moiety. The expected synergistic binding of the bi-substrate analogs as compared with either a creatine analog or ATP alone should provide additional creatine kinase active site-directed affinity reagents (e.g., substrate analogs incorporating an electrophilic moiety which are active site-directed competitive and irreversible inhibitors of creatine kinase) with the necessary specificity.

Thirdly, members of a new class of mechanism-based inactivators of creatine kinase can be used. Strained four-membered guanidinium compounds are prototypic of this subset of substrate analogs, which incorporate an electrophilic moiety (in this case, a strained, four-membered, carbon-bridged guanidinium), and which are active site-directed competitive and irreversible inhibitors of creatine kinase (e.g., compounds 14 and 15, FIG. 24). These compounds are anticipated to be sufficiently electrophilic in themselves to alkylate the sulfhydryl located at or near the active site of creatine kinase. Alternatively, or in addition, phosphorylation by the enzyme and subsequent protonation of the resultant phosphorylated nitrogen is expected to generate a doubly charged N-phosphoryl guanidinium group that should be highly reactive towards any proximal active site nucleophilic residues. Simple dibromomethane treatment of creatine or a mono-amino protected N-amidinoglycine derivative can generate compounds 14 and 15, respectively.

(4) N-Phosphorylcreatine Analogs Bearing Non-transferable Phosphoryl-like Groups Because creatine kinase catalyzes the reversible transfer of a phosphoryl group between creatine and ATP, and N-phosphorocreatine and ADP, N-phosphorocreatine is a competitive inhibitor of the enzyme with respect to creatine. Additionally, because the observed antiviral activity of cyclocreatine may be associated with the phosphoryl group transfer potential of 3-phosphoryl-l-carboxymethyl-2-iminoimidazolidine being significantly lower than that of N-phosphorocreatine, a fourth class of antiviral agents is suggested. These are N-phosphorocreatine analogs which bear non-transferable groups that mimic the N-phosphoryl moiety. In the presence of nitrate ion and MgADP$^{2+}$, creatine froms an extraordinarily tight ternary complex at the active site of creatine kinase, wherein the planar $NO_3^{2-}$ is thought to mimic the transferred phosphoryl group in the transition state (Milner-White, E. J. and D. C. Watts, *Biochem. J.* 122: 727-740 (1971)). A non-transferable phosphoryl-like group covalently bonded to a creatine analog may similarly form a very tight inhibitory complex.

Candidate antiviral agents having very low phosphoryl group transfer abilities have been identified. For instance, 1-carboxymethyl-2-methyl-3-phospho-4-imidazoline (compound 16, FIG. 24) and 1-carboxymethyl-2-imino-3-phospho-4-imidazoline (compound 17, FIG. 24) are examples of N-phosphorocreatine analogs having a phosphoryl group transfer potential below that of ATP. Further analogs of this type include compounds 18-20, having the $N^3$ of cyclocreatine replaced with a carbon that bears a phosphonic acid (compound 18, FIG. 24), a sulfonic acid (compound 19, FIG. 24) or nitro (compound 20, FIG. 24) group. Linear analogs of this type are also envisioned.

Compound 16 can be prepared by simple phosphorylation (e.g., as described by Struve, G. E. et al., *J. Org. Chem.* 42: 4035-4040 (1977)) of the known 1-carboxymethyl-2-methylimidazole (Nguyen, A. C. K., Ph.D. dissertation in Pharmaceutical Chemistry, (University of California, San Francisco, 1983)). Compound 17 can be made by phosphorylation of 1-carboxymethyl-2-iminoimidazole as described in (Lowe, G. and B. S. Sproat, *J. Biol. Chem.* 225: 3944-3951 (1980)).

Figure 25:
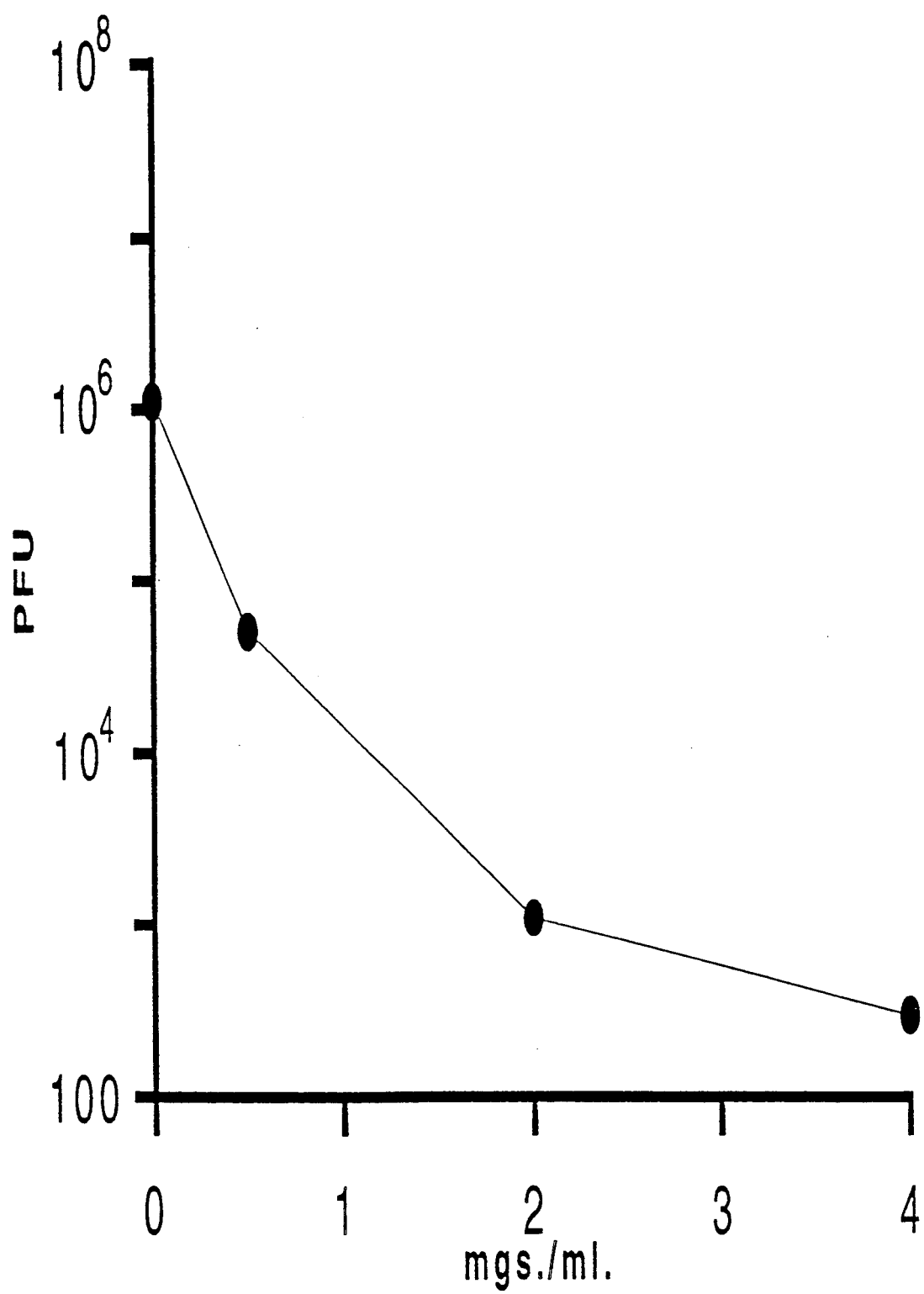
FIG. 25 illustrates sample synthetic schemes for making compounds 18-20 of FIG. 24.
Figure 26:
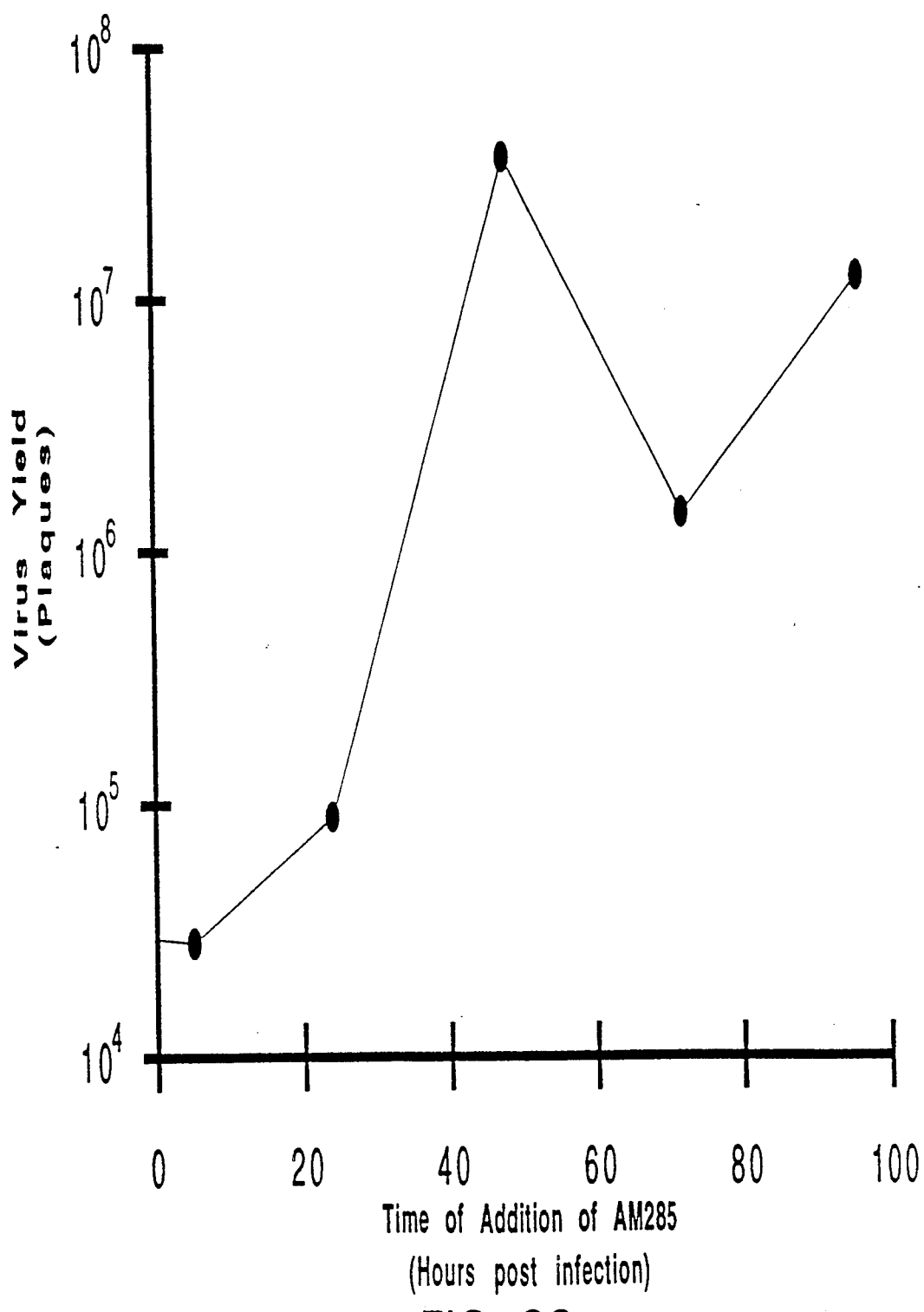
Figure 27:
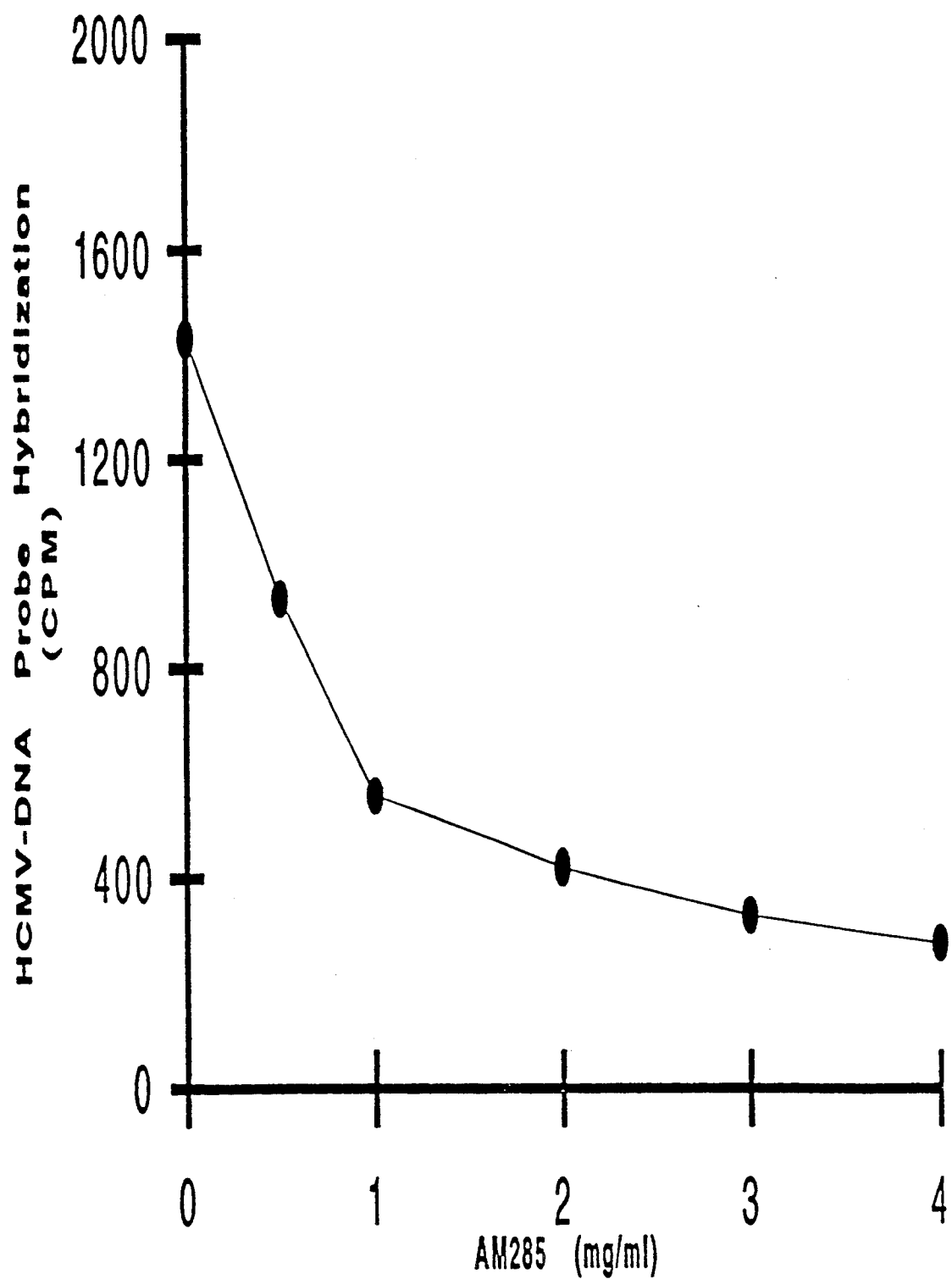

A proposed scheme for the synthesis of compounds 18-20 is shown in FIG. 25. Compounds 18-20 can be prepared from the glycine dipeptide derivative i by selective heteroatom substitution of the activated methylene carbon with either chlorodiethylphosphate, sulfur trioxide, or methyl nitrate followed by amidative cyclization of the secondary amine and nitrile as depicted (FIG. 25). The amino nitrile precursor i can be obtained by condensation of the primary amine ii with the trimethysilylethyl ester of iodoacetic acid iii. Protection of the secondary amine may be necessary for selective heteroatom functionalization and may be accomplished by trimethylsilylation. Treatment of i with mild base followed by chlorodiethylphosphate or methyl nitrate (after: Kornblum, *Org. React.* 12: 101-156, pp. 120-127 (1962)) can give intermediates iv and v, respectively. Treatment of i with sulfur trioxide in the absence of base, according to Gilbert (*Chem. Rev.* (1962) 549-589, pp. 558-559) can provide sulfonic acid vi. Intramolecular amidination of iv, vi, and v by treatment with ammonium fluoride would then yield compounds 18-20, respectively.

A variety of creatine analogs, including examples of each of the four general classes described above, are given by the following general formula:

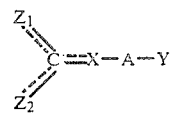

and pharmaceutically acceptable salts thereof.

a) Y is selected from the group consisting of: —CO$_2$H; —NHOH; —NO$_2$; —SO$_3$H; —C(=O)NHSO$_2$J and —P(=O)(OH)(OJ). In the latter cases, J is hydrogen, C$_1$-C$_6$ straight or branched chain alkyl, C$_2$-C$_6$ straight or branched alkenyl, or aryl group.

b) A is a C$_1$-C$_5$ alkyl, C$_1$-C$_5$ alkenyl, C$_2$-C$_5$ alkynyl, or C$_1$-C$_5$ alkoyl chain. The chain may have 0-2 bulky and/or hydrophobic substituents that are intended to enhance the effectiveness of the compound or to prevent its decomposition by pathways such as that in which creatine is cyclized to creatinine. The substituents are selected independently from the following:

(1) K, where K is a C$_1$-C$_6$ straight or branched alkyl or alkoyl, C$_2$-C$_6$ straight or branched alkenyl. K may also have 0-2 substituents, selected to be reactive with an enzymic nucleophile. A halogen, such as Br or Cl, or an epoxy or acetoxy group are examples of such reactive groups.

(2) An aryl group containing a 1-2 carbocyclic (such as phenyl or naphthyl) or heterocyclic ring (such as indolyl or adeninyl). The aryl group contains 0-2 substituents that could react with an enzymic nucleophile, such as —$CH_2L$ or —$COCH_2L$, in which L is a leaving group such as bromo, chloro, epoxy or acetoxy; and (3) —NH—M, wherein M is hydrogen, $C_1$-$C_4$ straight or branched alkyl or alkoyl, $C_2$-$C_4$ straight or branched alkenyl.

(c) X is selected from the group consisting of: $NR_1$, $CHR_1$, $C_1$ alkenyl with an $R_1$ substituent, O and S, wherein $R_1$ is selected from the group consisting of:
(1) Hydrogen;
(2) K as described in (b);
(3) An aryl group as described in (b);
(4) $C_5$-$C_9$ α-amino-ω-methyl-ω-adenosylcarboxylic acid attached via the ω-methyl carbon;
(5) $C_5$-$C_9$ α-amino-ω-aza-ω-methyl-ω-adenosylcarboxylic acid attached via the ω-methyl carbon; and
(6) $C_5$-$C_9$ α-amino-ω-thia-ω-methyl-ω-adenosylcarboxylic acid attached via the ω-methyl carbon.

(d) If A is chosen as a $C_1$ alkenyl group, then X must also be chosen as an alkenyl group, and if X is chosen as a $C_1$ alkenyl group, then A must be an alkenyl group, wherein A and X are connected by a double bond.

(e) $Z_1$ and $Z_2$ are chosen independently from the group consisting of: =O, —$NHR_2$, —$CH_2R_2$, —$NR_2OH$; wherein, $Z_1$ and $Z_2$ may not both be =O and wherein $R_2$ is selected from the group consisting of:
(1) Hydrogen;
(2) K as described in (b);
(3) An aryl group as described in (b);
(4) $C_4$-$C_8$ α-amino-carboxylic acid attached via the ω-carbon;
(5) B, wherein B is selected from the group consisting of: —$CO_2H$, —NHOH, —$SO_3H$, —$NO_2$, —OP(=O)(OH)(OJ) and —P(=O)(OH)(OJ). As above, J is either hydrogen, $C_1$-$C_6$ straight or branched alkyl, $C_2$-$C_6$ straight or branched alkenyl, or aryl. B is optionally connected via a linker, such as a $C_1$-$C_2$ alkyl, $C_2$ alkenyl, or $C_1$-$C_2$ alkoyl;
(6) -D-E, wherein D is selected from the group consisting of: $C_1$-$C_3$ straight or branched alkyl, $C_2$-$C_3$ straight or branched alkenyl, $C_1$-$C_3$ straight alkoyl, aryl, and aroyl. E is selected from the group consisting of: —$(PO_3)_n$NMP, where n is 0-2 and NMP is a ribonucleotide monophosphate connected via the 5'-phosphate, 3'-phosphate or the aromatic ring of the base; —[P(=O)(OCH_3)(O)]_m—Q, where m is 0-3 and Q is a ribonucleoside connected via the ribose or the aromatic ring of the base; —[P(=O)(OH)(CH_2)]_m—Q, where m is 0-3 and Q is a ribonucleoside connected via the ribose or the aromatic ring of the base; and an aryl group containing 0-3 substituents, such as a halogen (Cl, Br) or a group represented by the formula: —OG, —C(=O)G, or —$CO_2G$, in which G is a $C_1$-$C_6$ straight or branched alkyl, $C_2$-$C_6$ straight or branched alkenyl, or $C_1$-$C_6$ straight or branched alkoyl. E maybe attached at any point to D.

If D is an alkyl or alkenyl group, it may be connected at either or both ends by an amide linkage. An amide linkage can be in either orientation (—CONH— or —NHCO—), and if two amide linkages are present their orientations may be the same or different.

(7) -E, wherein E is as described above in (6) and if E is aryl, E may be linked by an amide linkage, which can be in either orientation.

(f) If $R_1$ and at least one $R_2$ group are present, $R_1$ may be connected by a single or double bond to an $R_2$ group to form a cycle of 5 to 7 members.

(g) If two $R_2$ groups are present, they may be connected by a single or double bond to form a cycle of 4-7 members.

(h) If $R_1$ is present and $Z_1$ or $Z_2$ is —$NHR_2$, —$CH_2R_2$ or —$NR_2OH$, then $R_1$ may be connected by a single or double bond to the carbon or nitrogen of either $Z_1$ or $Z_2$ (i.e., —$NHR_2$, —$CH_2R_2$ or —$NR_2OH$, a carbon or nitrogen which is not part of $R_2$) to form a cycle of 4 to 7 members.

Utility

Creatine analogs such as cyclocreatine can be administered to an individual (e.g., a mammal), alone or in combination with another drug, for the treatment of vital infection (i.e., as antiviral agents in therapy). As antiviral agents for the treatment of viral infection, creatine analogs can interfere with viral functions, thereby preventing, reducing, or eliminating direct and/or indirect effects of viral infection which contribute to disease and its symptoms in an individual, such as cytopathogenicity and spread of infection from cell to cell. For example, the cytopathic effect of a virus on an infected cell can be reduced by contacting a virally infected cell with a creatine analog. Results indicate that a variety of viral infections can be treated with cyclocreatine or other creatine analogs, including infections caused by DNA viruses (e.g., Adenovirus, Herpesviruses, such as Herpes simplex viruses, cytomegaloviruses, Varicella-Zoster virus, Epstein-Barr viruses, Human lymphotrophic virus type VI) as well as RNA viruses such as Influenza viruses (a double-stranded RNA virus).

Cyclocreatine or other analogs of creatine can be used to reduce the severity of an infection, reduce symptoms of primary infection, or prevent or reduce the severity of recurrent active infection, as in HSV infections. Creatine analogs such as cyclocreatine can be used to treat Herpes simplex virus infections. For example, topical application of a creatine analog in cream formulation can reduce the severity of lesions due to HSV infection of mucocutaneous surfaces of a mammal. Treatment can result in the reduction of viral shedding, of formation of new lesions, and of other clinical symptoms. Oral administration for initial treatment of genital infections or parenteral administration for severely ill individuals (e.g., neonates with HSV infection) is also possible. Because cyclocreatine accumulates in tissues in brain, cyclocreatine or other creatine analogs may have utility in treatment of infections of the central nervous system, such as HSV encephalitis or HSV aseptic meningitis. Interestingly, in the mouse vaginitis model described in Example 2, where death of the animals is due to HSV encephalitis, survival appeared to be improved and the mean day to death increased by coadministration of 1% dietary cyclocreatine and 100 mg/kg acyclovir (given by gavage).

Creatine analogs can also be used to treat Herpes Zoster (reactivated Varicella Zoster Virus infections) and cytomegalovirus infections (e.g., human cytomegalovirus (HCMV) chorioretinitis, encephalitis, enteritis, interstitial pneumonia, hepatitis). In particular, cyclocreatine has been shown to have antiviral activity against human cytomegalovirus (HCMV). Few antiviral agents are effective against HSV, Varicella Zoster Virus and HCMV infections; creatine analogs can provide optional or adjunct therapy for these infections, which can be severe in immunocompromised patients, such as AIDS patients, or immunosuppressed individuals, such as transplant recipients.

As shown herein, cyclocreatine has a synergistic effect when administered with the nucleoside analog acyclovir (Example 4). In vivo, with dietary administration of cyclocreatine (feed having 1% cyclocreatine) and acyclovir administered by gavage (100 mg/kg), results are consistent with an additive effect under the conditions used. Moreover, as noted above, a protective effect against HSV-induced mortality was observed in the same experiment, indicating utility in treatment of disseminated infection. Thus, cyclocreatine or other creatine analogs, may be particularly useful when administered in combination with other antiviral agents such as antiviral nucleoside analogs (e.g., acyclovir, ganciclovir, idoxuridine, trifluridine, vidarabine, dideoxyinosine, zidovudine (azidothymidine) or nucleotide analogs, such as foscarnet (phosphonoformic acid) and fosfonet (phosphonoacetic acid).

For example, a creatine analog such as cyclocreatine can be administered with vidarabine, which is useful in treating neonatal HSV or Varicella Zoster infections. Similarly, creatine analogs may be administered with trifluridine, idoxuridine, or vidarabine, which are useful in the treatment of HSV-1 eye infections.

As discussed above, cyclocreatine appears to operate via a mechanism distinct from that of acyclovir and ganciclovir. The use of smaller amounts of combinations of antiviral agents which act by distinct mechanisms may prevent the emergence of resistant strains. In addition, cyclocreatine and other creatine analogs can provide an alternate therapy where such resistant strains (e.g., DHPG resistant CMV strains, acyclovir resistant HSV strains, azidothymidine resistant HIV strains) already occur.

In addition, the finding that creatine analogs such as cyclocreatine have antiviral activity suggests a method for identifying additional candidate antiviral agents. For example, candidate phosphorylatable creatine analogs can be subjected to an initial screening for substrate activity in an assay using an isozyme of creatine kinase. Two sample creatine kinase enzyme assay formats are described in Examples 6 and 7. Potential bisubstrate inhibitors of creatine kinase, comprising covalently linked structural analogs of adenosine triphosphate (ATP) and creatine, or creatine analogs which are potential irreversible inhibitors of creatine kinase, can be tested for the appropriate inhibitory activity using known methods. Analogs which exhibit the desired substrate or inhibitory behavior in an assay with creatine kinase are then selected for further analysis in assays of antiviral activity. Modes of Administration For in vivo applications, cyclocreatine or another creatine analog can be administered alone or in combination with another creatine analog or other drug. For example, cyclocreatine can be administered with another antiviral agent such as a nucleoside analog as discussed above. The creatine analogs (e.g., cyclocreatine, AM 361) can be administered by a variety of routes, including, but not necessarily limited to, oral (dietary), topical, transdermal, or parenteral (e.g., subcutaneous, intramuscular, intravenous injection) routes of administration, for example. A therapeutically effective amount (i.e., one that is sufficient to produce the desired effect in an individual) of a composition comprising a creatine analog is administered to the individual. The actual amount of drug to be administered will depend on factors such as the size and age of the individual, in addition to the severity of symptoms, other medical conditions and the desired aim of treatment (desired effect).

In previous studies investigating the ability of creatine kinase inhibitors to sustain ATP levels or delay rigor during ischemic episodes in muscle, cyclocreatine was fed to mice, rats and chicks. Cyclocreatine appears to be well-tolerated in these animals. Newly hatched chicks have been fed a diet containing 1% cyclocreatine; in the presence of antibiotics, the chicks tolerated 1% cyclocreatine without significant mortality, although the chicks grew more slowly than control chicks. (Griffiths, G. R. and J. B. Walker, *J. Biol. Chem.* 251(7): 2049–2054 (1976)). Mice have been fed a diet containing 1% cyclocreatine for 10 days (Annesley, T. M. and J. B. Walker, *J. Biol. Chem.* 253(22): 8120–8125 (1978)). Cyclocreatine has been fed to mice at up to 1% of their diet for 2 weeks (see Example 3) or for over 4 weeks (data not shown), without gross adverse effects. Feeding animals cyclocreatine (e.g., 1% dietary) has been shown to lead to accumulation of cyclocreatine in different organs in mM concentrations. For example, cyclocreatine was reported to be taken up by muscle, heart and brain in rats receiving dietary 1% cyclocreatine (Griffiths, G. R. and J. B. Walker, *J. Biol. Chem.* 251(7): 2049–2054 (1976)). As shown herein, antiviral activity of cyclocreatine is observed on administering 1% dietary cyclocreatine. (In one report in which cyclocreatine was not purified, 1% cyclocreatine reportedly caused mortality and weight loss when fed to mice (21/34 mice survived 50 days of feeding with average weight of 80% of that of controls; Artru, A. A. and J. D. Michenfelder, *J. Neurochem.* 39: 1198–1200).

A selected creatine analog will be formulated according to the selected route of administration (e.g., powder, tablet, capsule, cream or ointment, solution, emulsion). An appropriate composition comprising a creatine analog can be prepared in a physiologically acceptable vehicle or carrier. For example, a composition in tablet form can include one or more additives such as a filler (e.g., lactose), a binder (e.g., gelatin, carboxymethylcellulose, gum arabic), a flavoring agent, a coloring agent, or coating material as desired. For cream or ointment preparations, crystalline powder can be mixed with an appropriate base, such as a polyethylene glycol (PEG) cream base. For solutions or emulsions in general, carriers include aqueous or alcoholic/aqueous solutions, emulsions or suspensions, including saline and buffered media. Parenteral vehicles can include sodium chloride, solution, Ringer's dextrose, dextrose and sodium chloride, lactated Ringer's or fixed oils. In addition, intravenous vehicles can include fluid and nutrient replenishers, and electrolyte replenishers, such as those based on Ringer's dextrose. Preservatives and other additives can also be present. For example, antimicrobial, antioxidant, chelating agents, and inert gases can be added. (See, generally, *Remington's Pharmaceutical Sciences*, 16th Edition, Mack, Ed., 1980).

The present invention will now be illustrated by the following Examples, which are not intended to be limiting in any way.

EXAMPLES

The materials described below were used in the Examples.

Compounds

Compounds used in these studies included cyclocreatine (1-carboxymethyl-2-iminoimidazolidine), 1-carboxymethyl-2-amino-imidazole, Ganciclovir (DHPG) and acyclovir. The synthesis of 1-carboxymethyl-2-iminoimidazolidine was carried out as described by Griffiths and Walker (Griffiths, G. R. and J. B. Walker, *J. Biol. Chem.* 251: 2049–2054 (1976)). The synthesis of 1-carboxymethyl-2-amino-imidazole was carried out as described by Lowe and Sproat (Lowe, G. and G. S. Sproat, *J. Biol. Chem.* 255(9): 3944–3951 (1980)). Acyclovir was obtained from Sigma Chemical Corp. (St. Louis, Mo.). Ganciclovir (DHPG) was obtained from Syntex Laboratories, Inc., Palo Alto, Calif.

EXAMPLE 1

In Vitro Antiviral Activity of Cyclocreatine against HSV-1 and HSV-2

Herpes Simplex Type I (HSV-1) Strain F

Frozen virus lot 14 was obtained from the American Type Culture Collection (ATCC VR-733) as a frozen 1.0 ml ampule containing infected fluid and cells. The original source was a human facial vesicle. The host range includes most mammalian cells. Ejerito et al., *J. Gen. Virol.* 2: 357–364, 1968; Roizman, B., et al., (1972), In: *Perspectives in Virology VIII*, Pollard, M., editor, (Academic Press, N.Y. ) pp. 129–169.

Herpes Simplex Type 2 (HSV-2) Strain MS

Frozen virus lot 8 of HSV-2 strain MS was obtained from the ATCC as a frozen 1.0 mL ampule containing infected fluid and cells. The ATCC number is ATCC VR-540. The original source of the virus was the brain of a 50 year old female with multiple sclerosis. The host range includes most mammalian cells. Gudnadottir, M. et al., *Exp. Neurol.* 9: 85, (1964); Pauls, F. P. et al., *J. Immunology.* 98: 941, (1967); Dowdle, W. R. , *J. Immunology* 99: 974, (1975) .

Preparation and Titer of HSV Viral Stocks

Herpes simplex virus stocks were stored at $-80°$ C. Laboratory stocks used for the in vitro experiments were prepared by the following method: 75 $cm^2$ flasks of confluent DU145 cells were inoculated with 1 ml aliquots of a previous lab stock by adding an aliquot of HSV-1 stock ($4.67 \times 10^5$ PFU/ml) or HSV-2 stock ($7.93 \times 10^4$ PFU/ml) directly to the 20 ml of media overlaying the cells. Total destruction of the cell monolayer was observed after 3–4 days of viral replication in culture. The medium, containing virus and remaining cells, was collected into conical tubes, was frozen in a dry ice bath ($-80°$ C.), and was then thawed at $37°$ C. for 30 min. Following an additional freeze-thaw cycle, the cell debris was removed by centrifugation at 2000 rpm in a Beckmann GPR centrifuge for 3 min. The virus stock (the supernatant) was divided into aliquots and stored at $-80°$ C. in 2 ml cryovials.

The titer of the HSV-1 and HSV-2 viral stocks was determined by plaque assay on Vero cells. 75–90% confluent Vero cells in 6-well plates were inoculated with serial dilutions of the stock virus to be titered. Each well represented a 10-fold dilution, ranging from $10^{-1}$ to $10^{-8}$. The virus was diluted in 2 ml of serum-free media and was incubated with the cells for 1 hour at $37°$ C. After the 1 hour incubation, the inoculum was removed by aspiration and replaced by 3 ml of agarose-medium maintained at $42°$ C. The plates were then incubated at $37°$ C. for 2–3 days to allow plaques to develop. Agarose-medium is a fresh 1:1 mixture of (1) 1% Seaplaque agarose (FMC Corp., Rockland, Me.) in tissue culture grade water (JRH Biosciences, Lenexa Kans.) melted at 100 ° C. for 30 min and (2) 2×MEM/20% FBS/4 mM L-glutamine/200 units/ml penicillin and 200 µg/ml streptomycin activity (JRH Biosciences).

To visualize plaques, 5% formaldehyde was added to agarose-medium overlays and left for 45 minutes to 2 hours in order to fix the remaining cells to the plate. The fixed monolayer was then stained for 2 hours with 0.25% crystal violet in ethanol. Plaques were counted under a microscope at 40× magnification. The titers determined were $2.5 \times 10^6$ PFU/ml for HSV-1 and $6.0 \times 10^5$ PFU/ml for HSV-2. The determined plaque number per stock may vary 2–3 fold depending on the end-point and the cell line chosen for the assay.

Cell Lines and Growth Media

All cell lines used for the HSV-1 and HSV-2 in vitro experiments, with the exception of A2058 cells, were obtained from the ATCC. Vero cells, a cell line initiated from the kidney of a normal, adult, African green monkey, were propagated in 1×EMEM, 5% Fetal Bovine Serum, 2 mM L-glutamine, 100 U/ml penicillin, 100 µg/ml streptomycin, and 0.11 mg/mL Na pyruvate. Vero cells have been used extensively in virus replication studies. Balb/3T3, clone A31 cells, a contact-inhibited, non-tumorigenic line established from mouse embryo cells, was maintained in 1×DMEM, 10% calf serum, 2 mM L-glutamine, 100 U/ml penicillin, 100 µg/ml streptomycin, and 0.11 mg/ml Na pyruvate. A549 cells, initiated through explant culture of lung carcinomatous tissue from a 58 year-old Caucasian male, were maintained in 1×Kaighn's Nutrient Mixture F12 (aka Hans F-12K), 10% FBS, 2 mM L-glutamine, 100 U/ml penicillin, and 100 µg/ml streptomycin. DU145 cells, isolated from a lesion in the brain of a patient with widespread metastatic carcinoma of the prostate, were propagated in 1×EMEM, 10% fetal bovine serum, 2 mM L-glutamine, 100 U/ml penicillin, 100 µg/ml streptomycin, and 0.11 mg/ml Na pyruvate. A2058 cells, a human melanoma line obtained from Marie E. Beckner of the National Cancer Institute, were grown in 1×DMEM, 10% FBS, 4 mM L-glutamine, 100 U/ml penicillin, 100 µg/ml streptomycin, and 0.11 mg/ml Na pyruvate.

Cytopathic Effect (CPE) Assay Procedure

Drug stocks were prepared at concentrations of 4–10 mg/ml in 1×medium appropriate for the selected cell line and were further diluted (dilution factor of 0.75) in the same medium. Serial dilutions of virus inoculum in the appropriate 1×serum-free medium were made using a motorized EDP multichannel pipet prior to addition to the cells.

Serum-starved (Vero, DU 145) or contact-inhibited (A549, Balb/3T3 clone A31) monolayers were established by the following procedure. Cells were split into 96-well tissue culture plates (Falcon, #3075) using the growth medium appropriate for each cell line. Once the cells were confluent, they were either serum-starved for 3 to 5 days or were allowed to contact arrest for 2 days.

Growth medium was aspirated from established serum-starved or contact-arrested monolayers of cells. A 100 μl volume of virus inoculum was placed in each well, except for those wells to be used as uninfected cell controls (8 wells/plate) and in which 100 μl of media was placed. Plates were incubated at 37° C. for 1-2 hours to allow viral adsorption to cells. The viral inoculum was removed by aspiration and the monolayers were washed once with fresh, serum-free medium. Agarose-medium (0.2 ml), maintained at 42° C., and containing various concentrations of drug, was added to each well. Agarose-medium is a fresh 1:1 mixture of (1) 1% Seaplaque agarose (FMC Corp., Rockland, Me.) in tissue culture grade water (JRH Biosciences, Lenexa Kans.) melted at 100° C. for 30 min and (2) 2×MEM/20% FBS/4 mM L-glutamine/200 units/ml penicillin and 200 μg/ml streptomycin activity (JRH Biosciences).

Serial dilutions of drug were then added to the wells with a motorized EDP multichannel pipet. For each viral inoculum, medium without drug was added to one well to establish no drug controls ("virus controls"). The plates were incubated at 37° C. in a moist atmosphere of 5% $CO_2$ and 95% air until a large percentage of monolayer death was observed in the virus control wells.

Cytopathic effect was determined by estimation of the percentage of monolayer death of unfixed or, in some cases, fixed cells. To fix cell monolayers, the medium was removed by aspiration from each well, and the cells were treated with 5% formaldehyde and stained by addition of 0.1 ml of 0.25% crystal violet in 95% ethanol to each well. Alternatively, cells were fixed with 50 μl of 50% TCA and stained with 0.1 mls of 0.4% sulforhodamine B (Aldrich Chemical Co., Milwaukee, Wis.). After 2 hours, the stain was removed by aspiration. The plates were rinsed in running tap water until the water was clear, and the plates were inverted and dried at room temperature. Alternatively, the percentage of monolayer death was estimated from examination of live, unfixed cells. For both fixed and live cells, the percentage of monolayer death was estimated at 100× magnification under a phase-contrast microscope.

Therapeutic Index

The therapeutic index (TI) for each drug tested was calculated by the formula: TI=CD50÷ED50. The CD50 is that concentration of antiviral substance calculated to be half-way between the concentration which produces no visible effect on the cells and the concentration which produces complete cytotoxicity. The ED50 is that concentration of antiviral substance which is calculated to reduce the CPE to half that of the virus controls.

Cytopathogenicity Studies of HSV-1 and HSV-2

To determine the antiviral effect of cyclocreatine against HSV-1 and HSV-2 in vitro, a number of cell lines were challenged with varying concentrations of virus as described above. The infected monolayers were incubated in the presence of several different concentrations of cyclocreatine until extensive cytopathogenicity was observed in the no drug control wells on the plate. For each cell line and virus, a no drug control plate was prepared and treated identically to the first plate, except that low serum medium lacking cyclocreatine was added to the infected monolayers.

FIG. 1 shows the results of such a cytopathogenicity study of HSV-1 in Vero cells. The percentage of monolayer death observed (x-axis) in each well at different concentrations of cyclocreatine (denoted by different shaded bars) is plotted for a range of viral inoculla (y-axis; plaque-forming units (PFUs) per inoculum). FIG. 1A shows that in serum-starved Vero cells, at all four viral inoculla tested, cyclocreatine inhibited the cytopathic effect of HSV-1. In the presence of cyclocreatine, there is a consistently observed dose response such that the greater the drug concentration, the greater the antiviral effect.

Figure 1B:
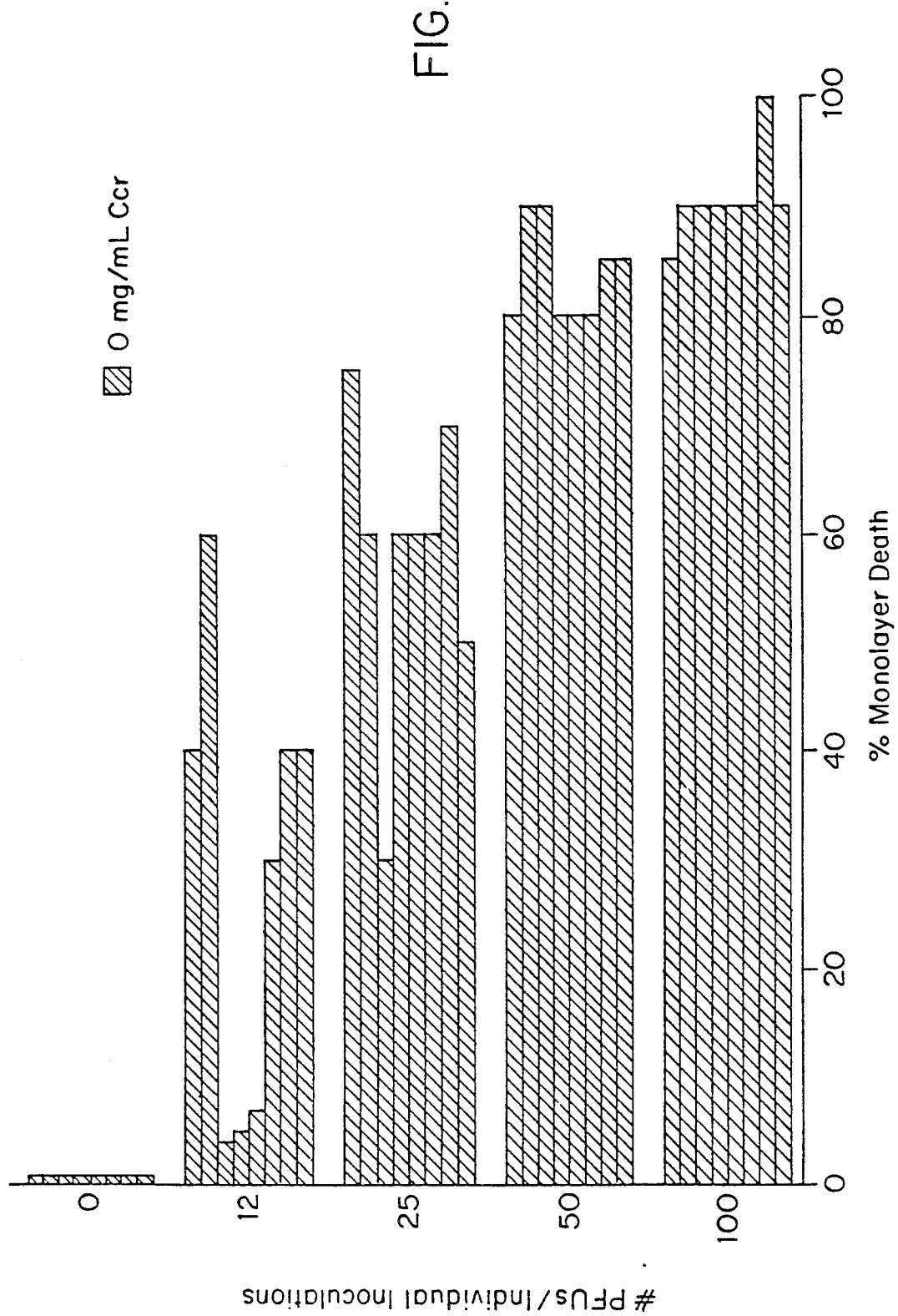
FIG. 1B is a bar graph depicting the effect of different amounts of HSV-1 virus on the percent monolayer death in the absence of drug or cyclocreatine (8-wells/inoculum). The length of each bar represents the percent monolayer death in a single well.

In FIG. 1A, the percent monolayer death in the absence of viral infection (0 PFUs) provided a control for drug cytotoxicity from the same plate as the infected cells. In addition, the results from the no drug control plate show that in the absence of cyclocreatine, most wells of Vero cells that receive a given inoculum of HSV-1 virus display comparable levels of cell death (FIG. 1B). This plate serves as a negative control for the experiment summarized in FIG. 1A and confirms that the dose response is due to the addition of cyclocreatine. Thus, cyclocreatine has a distinct anti-HSV-1 effect.

The 50% effective dose (ED50) for cyclocreatine against HSV-1 calculated from the experiment shown in FIG. 1A is 1.27 mg/ml or approximately 9 mM. There was no observed cytotoxicity, so by this experiment the CD50 is determined to be greater than 4 mg/ml or 28 mM. Other cytotoxicity experiments have shown that 70 mM cyclocreatine is well tolerated by serum-starved Vero cells. The therapeutic index is therefore calculated to be >7.6.

Figure 2A:
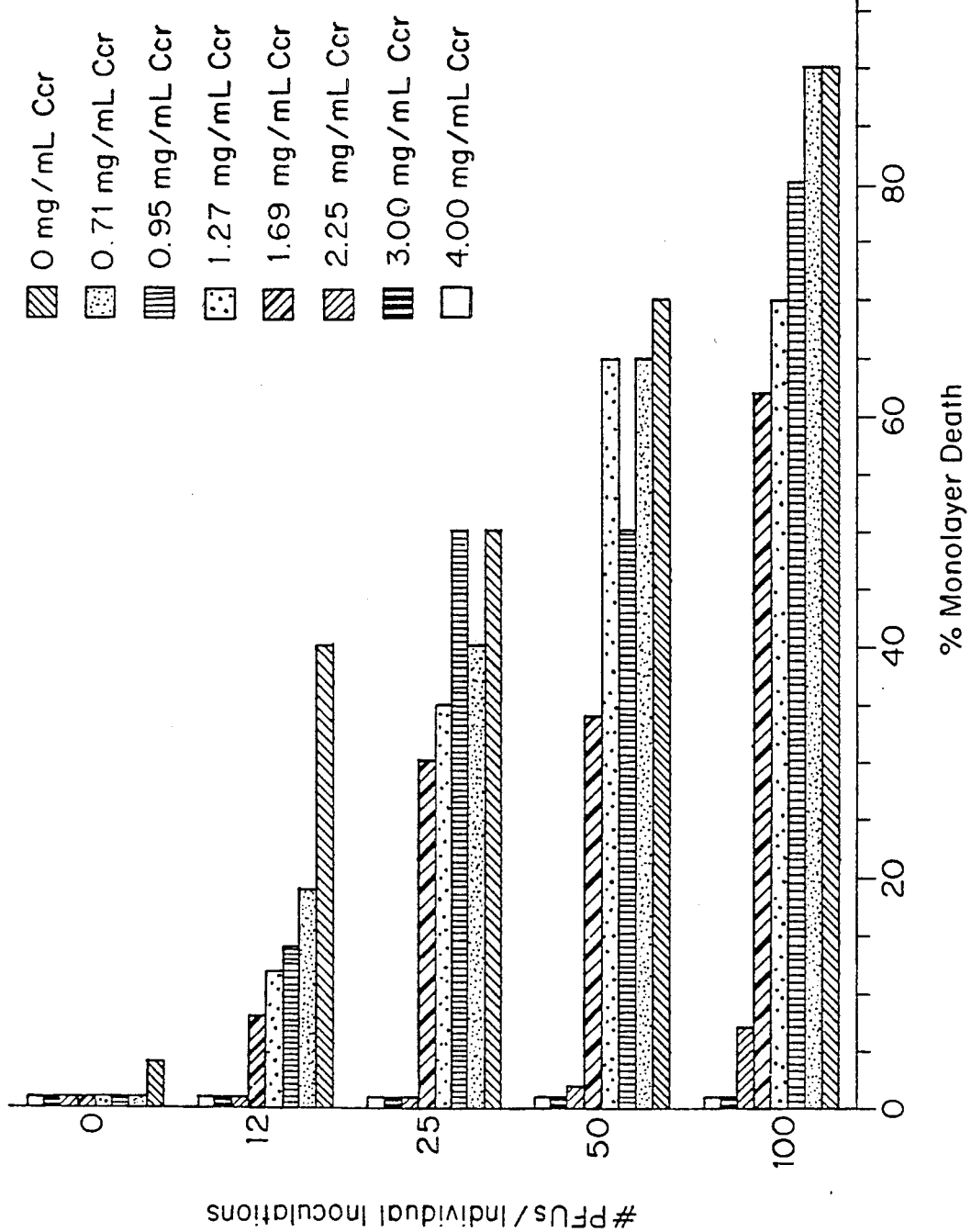
FIG. 2A is a bar graph depicting the effect of 8 different concentrations of cyclocreatine (bars from top to bottom for each inoculum: 4.0 mg/ml, 3.0 mg/ml, 2.25 mg/ml, 1.6 mg/ml, 1.27 mg/ml, 0.95 mg/ml, 0.71 mg/ml, 0 mg/ml) on the percent of monolayer cell death of Vero cells inoculated with various amounts of HSV-2 virus. The bar graph illustrates the protective effect of cyclocreatine in Vero cells against the cytopathic effect of HSV-2 infection.
Figure 2B:
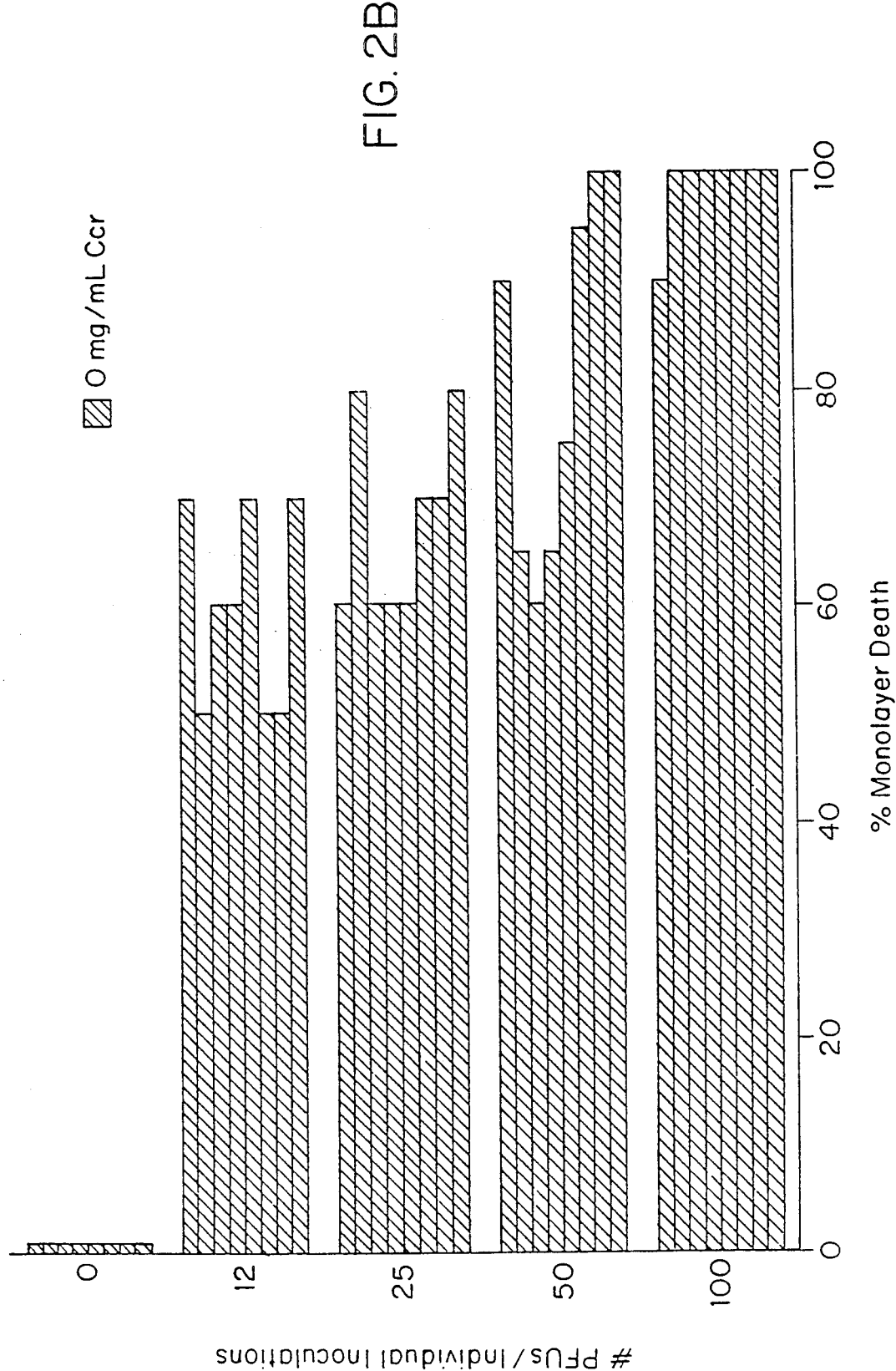
FIG. 2B is a bar graph depicting the effect of various amounts of HSV-2 virus on percent monolayer death in the absence of drug or cyclocreatine (8 wells/inoculum). The length of each bar represents the percent monolayer death in a single well.

FIGS. 2A and 2B summarize the results of a similar experiment with HSV-2. The results indicate that cyclocreatine inhibits the cytopathic effect of various amounts of HSV-2 in serum-starved Vero cells. As with HSV-1, there is a definite dose response. The ED50 is calculated to be 1.69 mg/ml or 11 mM. The CD50 is greater than 4 mg/ml or 28 mM. Other cytotoxicity experiments have shown that 70 mM cyclocreatine is well-tolerated by serum-starved Vero cells. The calculated TI is >5.5.

Figure 3A:
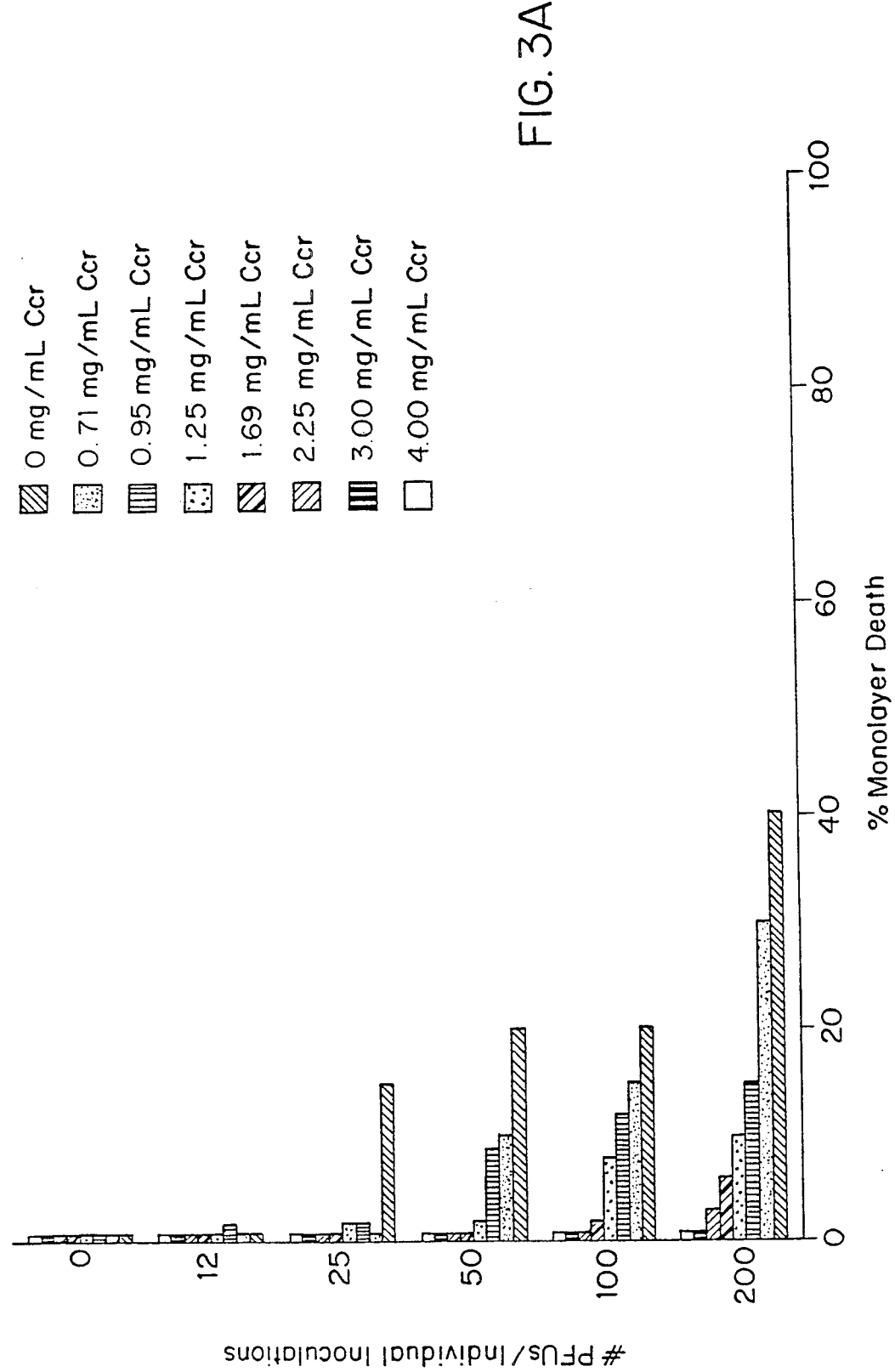
FIG. 3A is a bar graph depicting the effect of 8 different concentrations of cyclocreatine (bars from top to bottom for each inoculum: 4.0 mg/ml, 3.0 mg/ml, 2.25 mg/ml, 1.69 mg/ml, 1.25 mg/ml, 0.95 mg/ml, 0.71 mg/ml, 0 mg/ml) on the percent of monolayer cell death of Balb/3T3, clone A31 cells inoculated with various amounts of HSV-1 virus. The bar graph illustrates the protective effect of cyclocreatine in Balb/3T3, clone A31 cells against the cytopathic effect of HSV-1 infection.
Figure 3B:
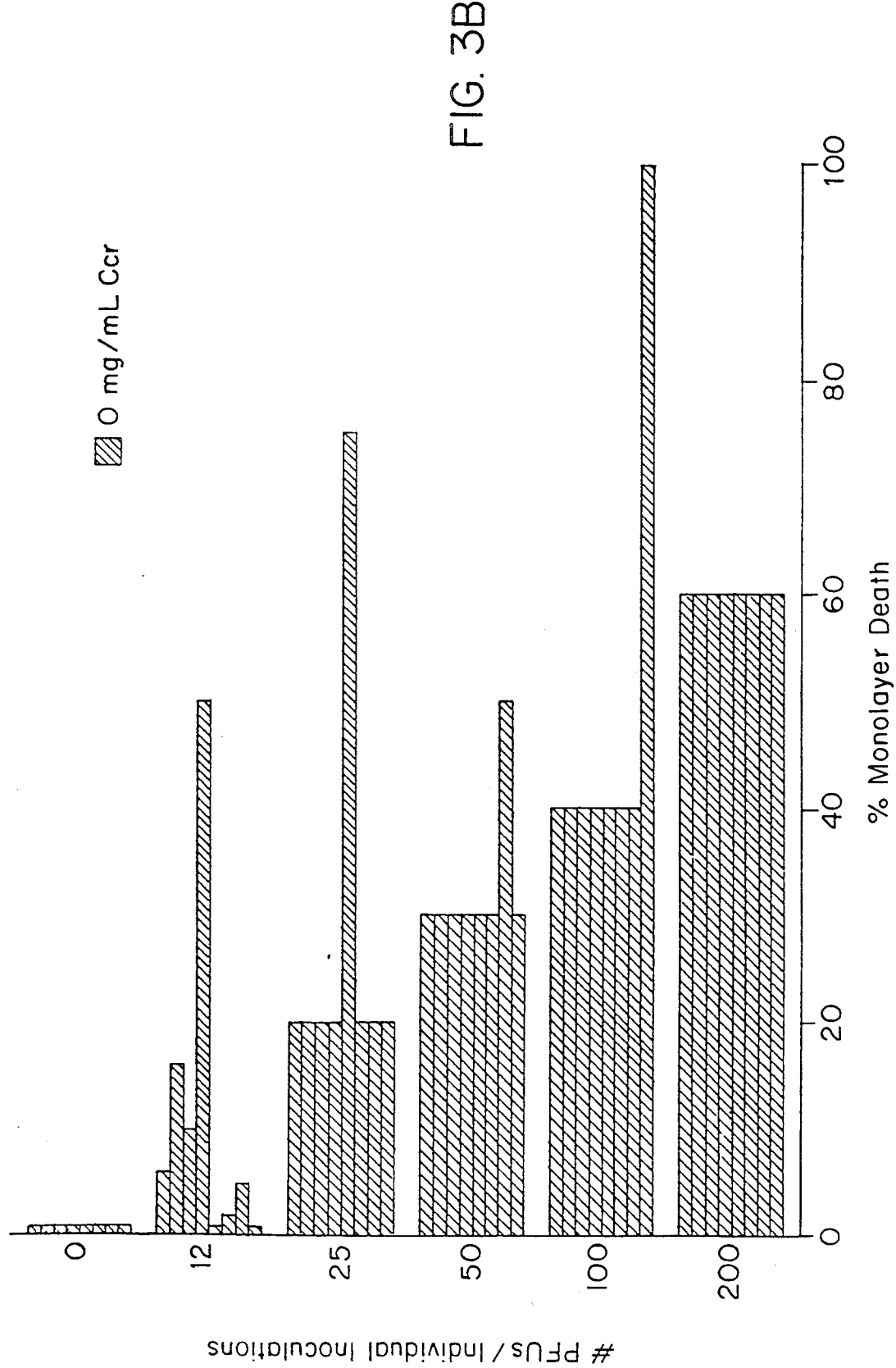
FIG. 3B is a bar graph depicting the effect of various amounts of HSV-1 virus on percent monolayer death in the absence of drug or cyclocreatine (8 wells/inoculum). The length of each bar represents the percent monolayer death in a single well.
Figure 4A:
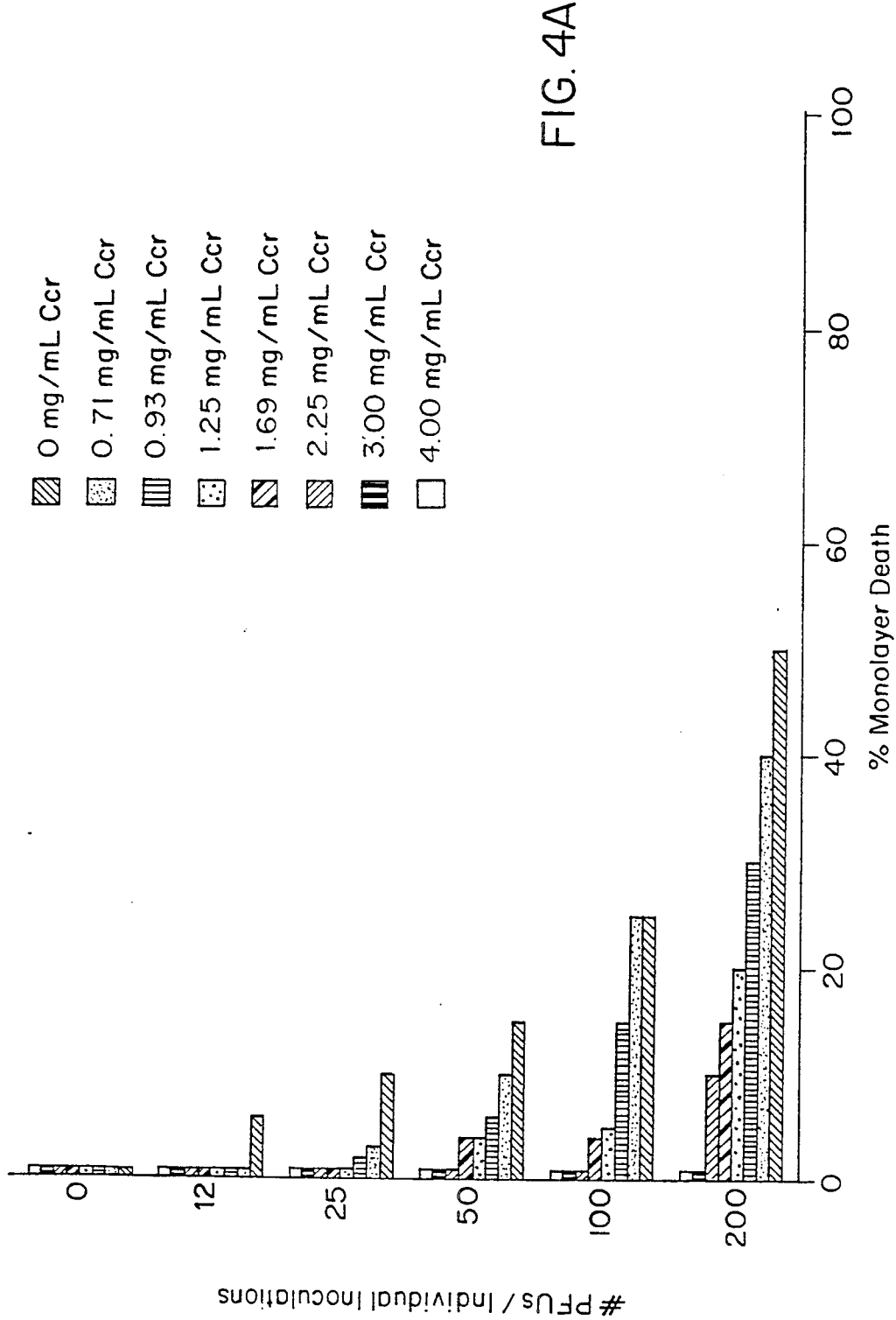
FIG. 4A is a bar graph depicting the effect of 8 different concentrations of cyclocreatine (bars from top to bottom for each inoculum: 4.0 mg/ml, 3.0 mg/ml, 2.25 mg/ml, 1.69 mg/ml, 1.25 mg/ml, 0.93 mg/ml, 0.71 mg/ml, 0 mg/ml) on the percent of monolayer cell death of Balb/3T3, clone A31 cells inoculated with various amounts of HSV-2 virus. The bar graph depicts the protective effect of cyclocreatine in Balb/3T3, clone A31 cells against the cytopathic effect of HSV-1 infection.
Figure 4B:
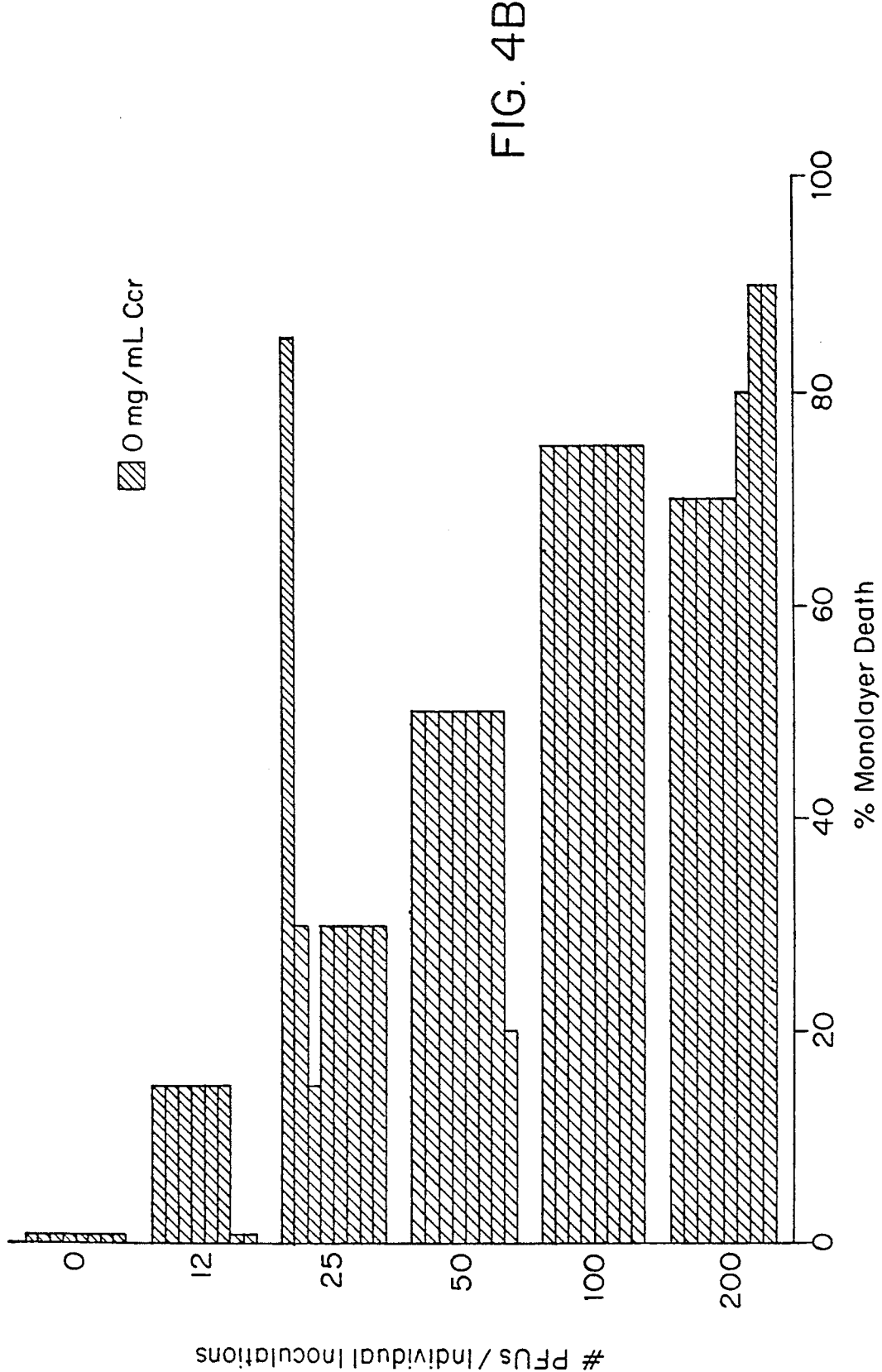
FIG. 4B is a bar graph depicting the effect of various amounts of HSV-2 virus on percent monolayer death in the absence of drug or cyclocreatine (8 wells/inoculum). The length of each bar represents the percent monolayer death in a single well.

To confirm the antiviral effects of cyclocreatine observed in Vero cells, similar experiments were performed using other cell lines. The results from experimental (FIG. 3A and 4A) and control (FIGS. 3B and 4B) plates indicate that cyclocreatine inhibited the cytopathic effect of various dilutions of HSV-1 (FIG. 3A) and HSV-2 (FIG. 4A) upon contact-inhibited BalbC/3T3 cells. FIGS. 3B and 4B show that in the absence of cyclocreatine, most wells of BalbC/3T3 cells which received a given inoculum of HSV-1 or HSV-2 virus displayed comparable levels of cell death.

Figure 5A:
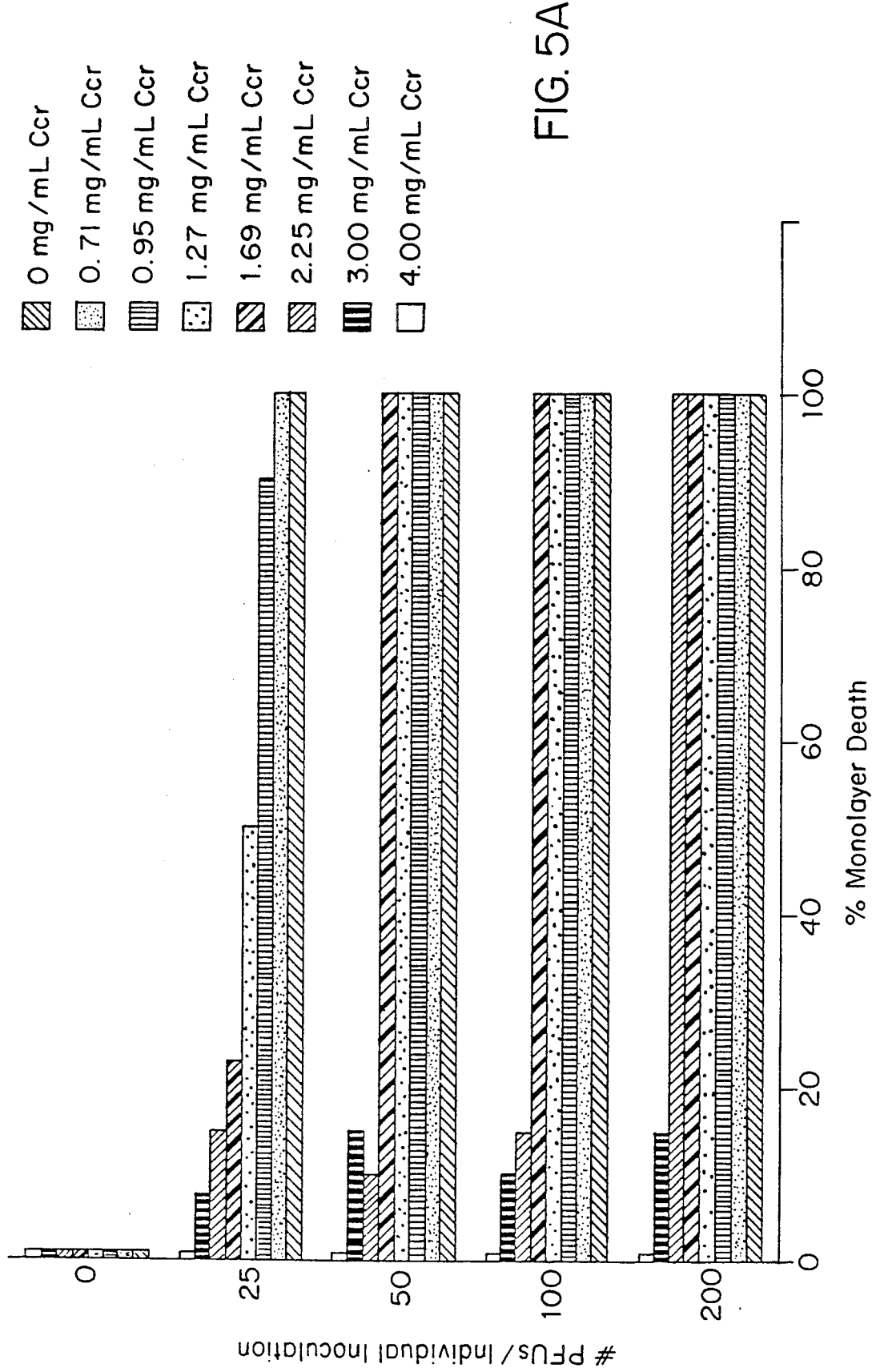
FIG. 5A is a bar graph depicting the effect of 8 different concentrations of cyclocreatine (bars from top to bottom for each inoculum: 4.0 mg/ml, 3.0 mg/ml, 2.25 mg/ml, 1.69 mg/ml, 1.27 mg/ml, 0.95 mg/ml, 0.71 mg/ml, 0 mg/ml) on the percent of monolayer cell death of DU145 cells inoculated with various amounts of HSV-1 virus. The bar graph illustrates the protective effect of cyclocreatine in DU145 cells against the cytopathic effect of HSV-1 infection.
Figure 5B:
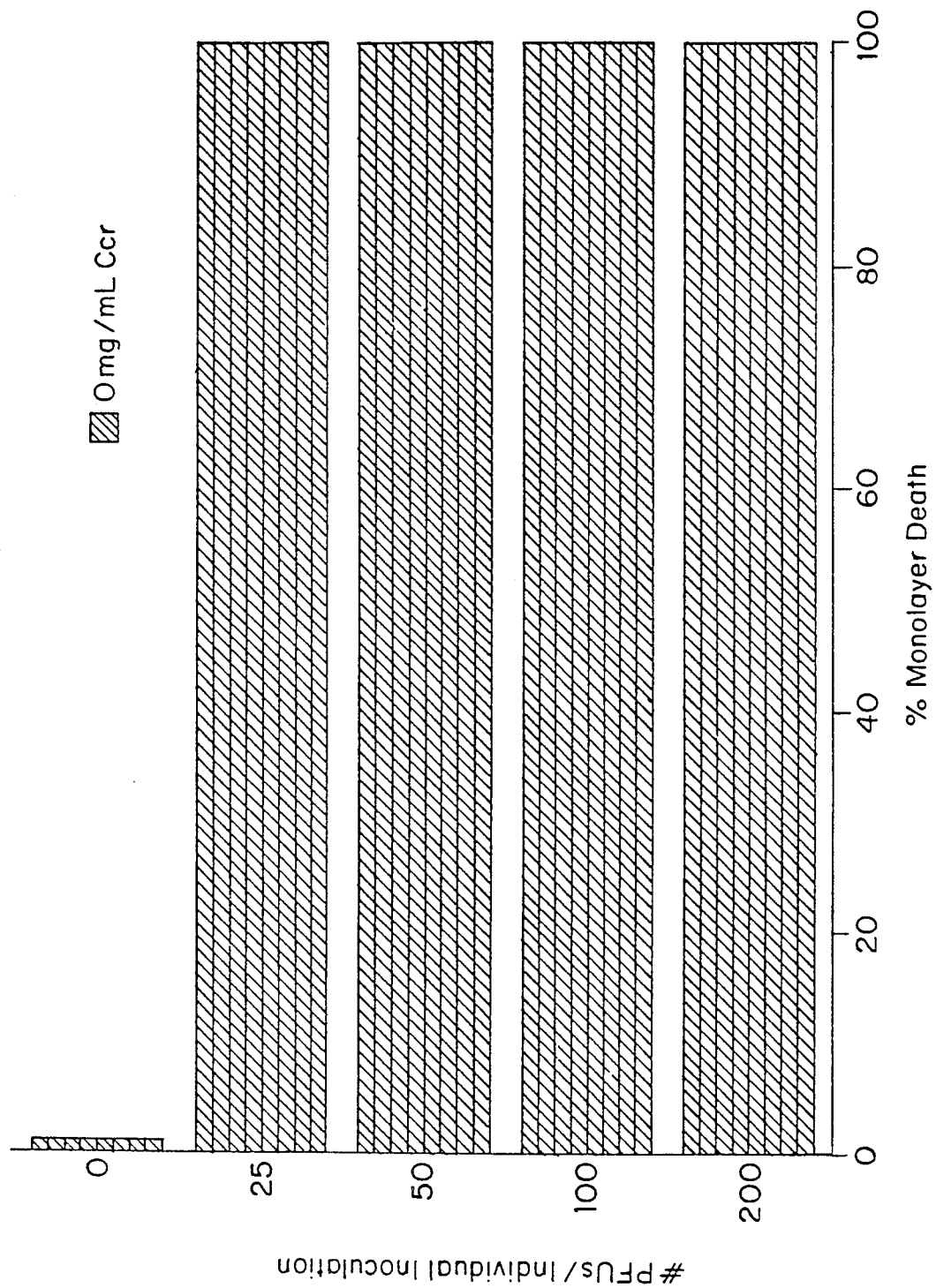
FIG. 5B is a bar graph depicting the effect of various amounts of HSV-1 virus on percent monolayer death in the absence of drug or cyclocreatine (8 wells/inoculum). The length of each bar represents the percent monolayer death in a single well.
Figure 6A:
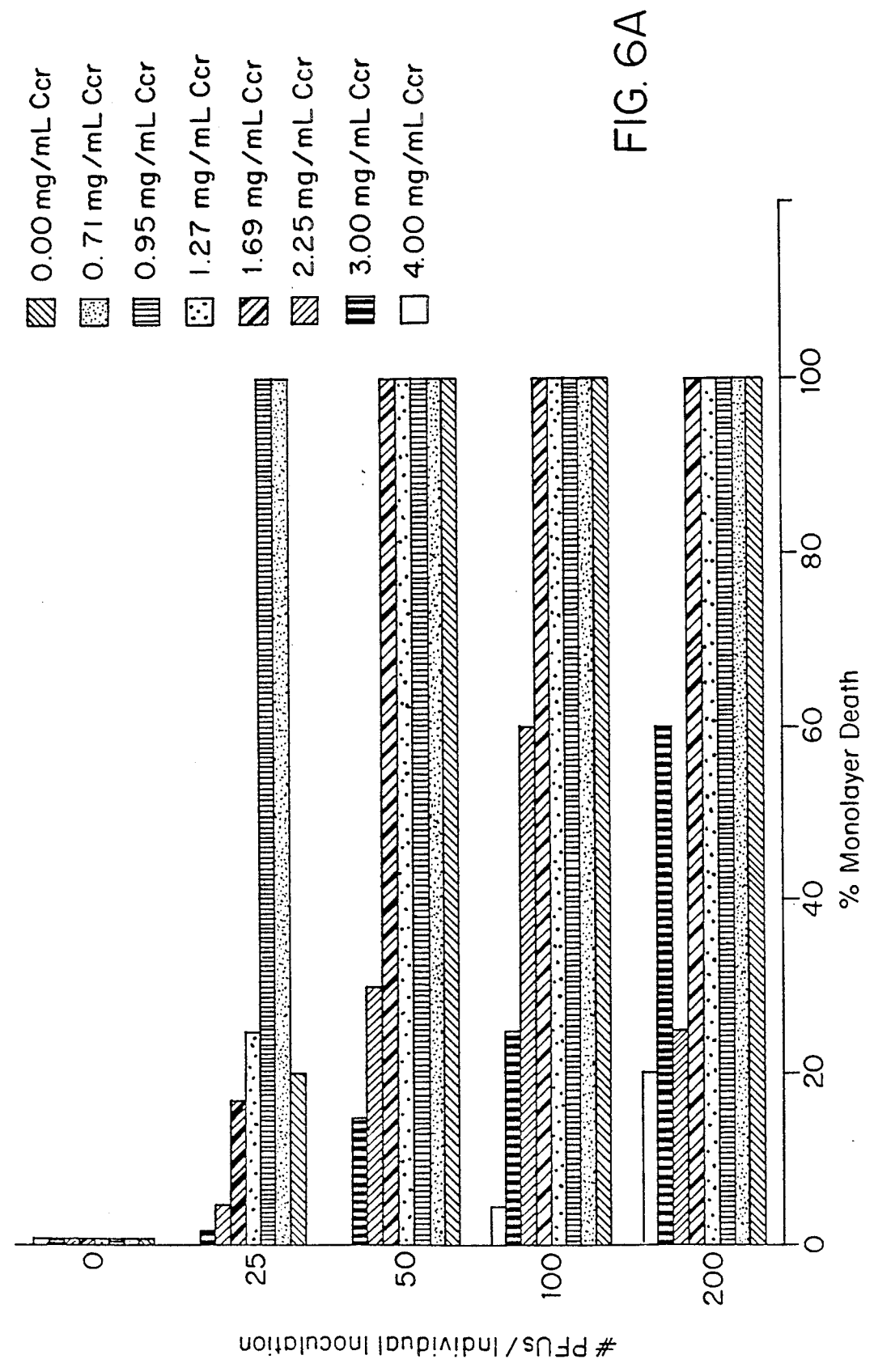

FIGS. 5 and 6 show that cyclocreatine inhibited the cytopathic effect of various amounts of HSV-1 (FIG. 5A) or HSV-2 (FIG. 6A) in serum-starved DU145 cells. The results of control experiments reported in FIGS. 5B and 6B confirmed that, in the absence of cyclocreatine, most wells of DU145 cells that received a given inoculum of HSV-1 (FIG. 5B) or HSV-2 (FIG. 6B) virus had comparable levels of cell death.

Figure 7A:
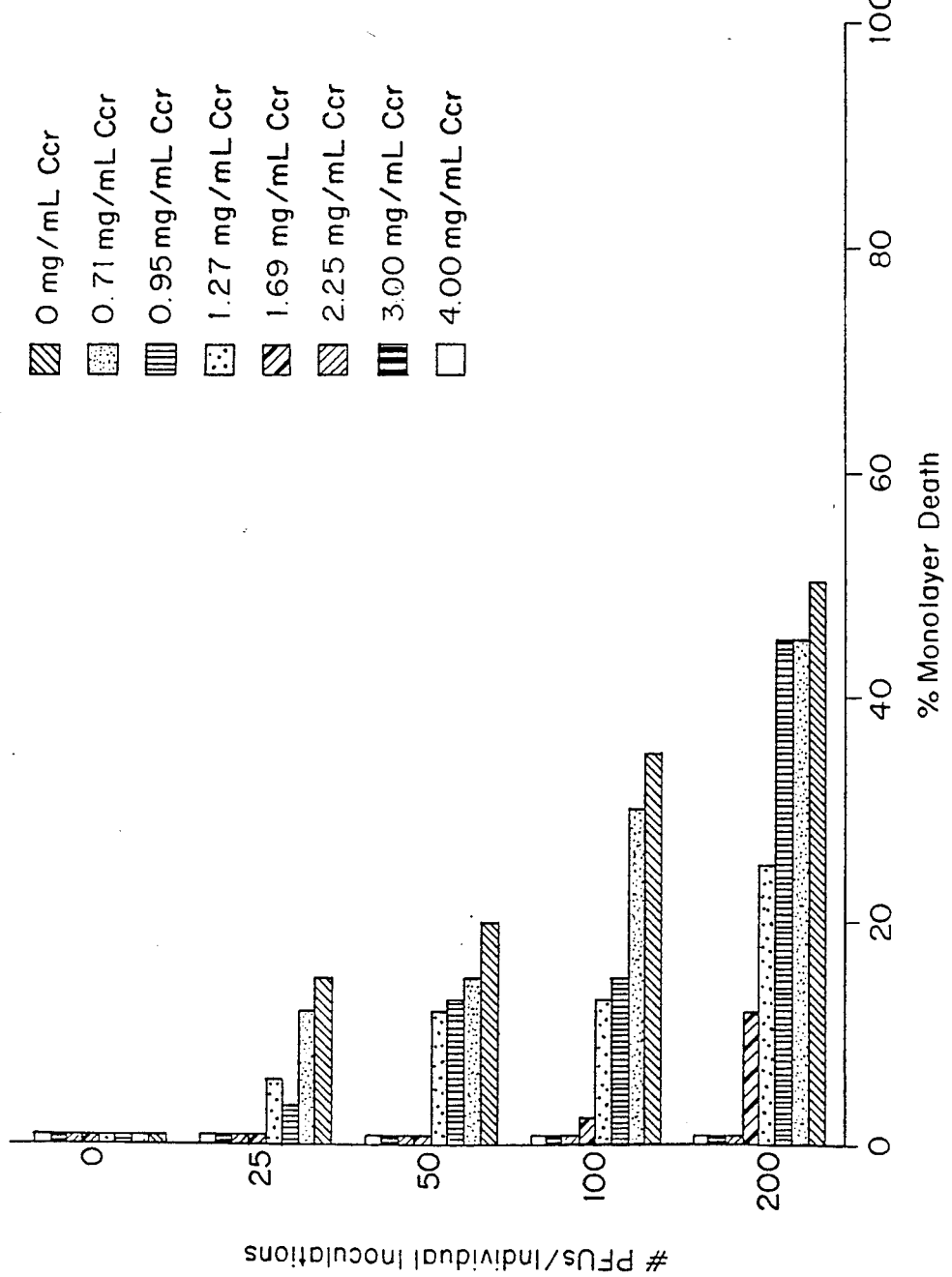
FIG. 7A is a bar graph depicting the effect of 8 different concentrations of cyclocreatine (bars from top to bottom for each inoculum: 4.0 mg/ml, 3.0 mg/ml, 2.25 mg/ml, 1.69 mg/ml, 1.27 mg/ml, 0.95 mg/ml, 0.71 mg/ml, 0 mg/ml) on the percent of monolayer cell death of A549 cells inoculated with various amounts of HSV-1 virus. The bar graph illustrates the protective effect of cyclocreatine in A549 cells against the cytopathic effect of HSV-1 infection.
Figure 7B:
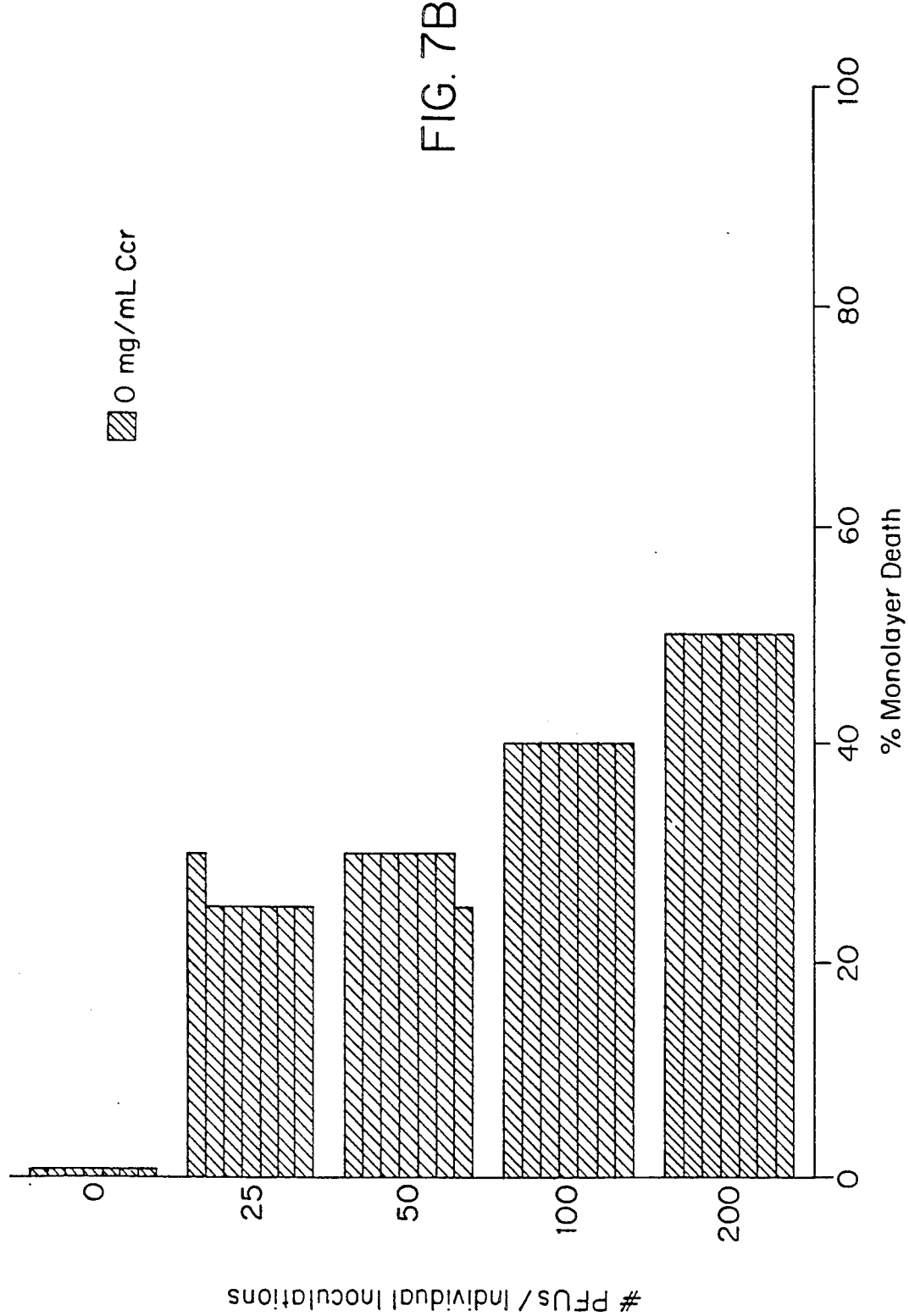
FIG. 7B is a bar graph depicting the effect of various amounts of HSV-1 virus on percent monolayer death in the absence of drug or cyclocreatine (8 wells/inoculum). The length of each bar represents the percent monolayer death in a single well.
Figure 8A:
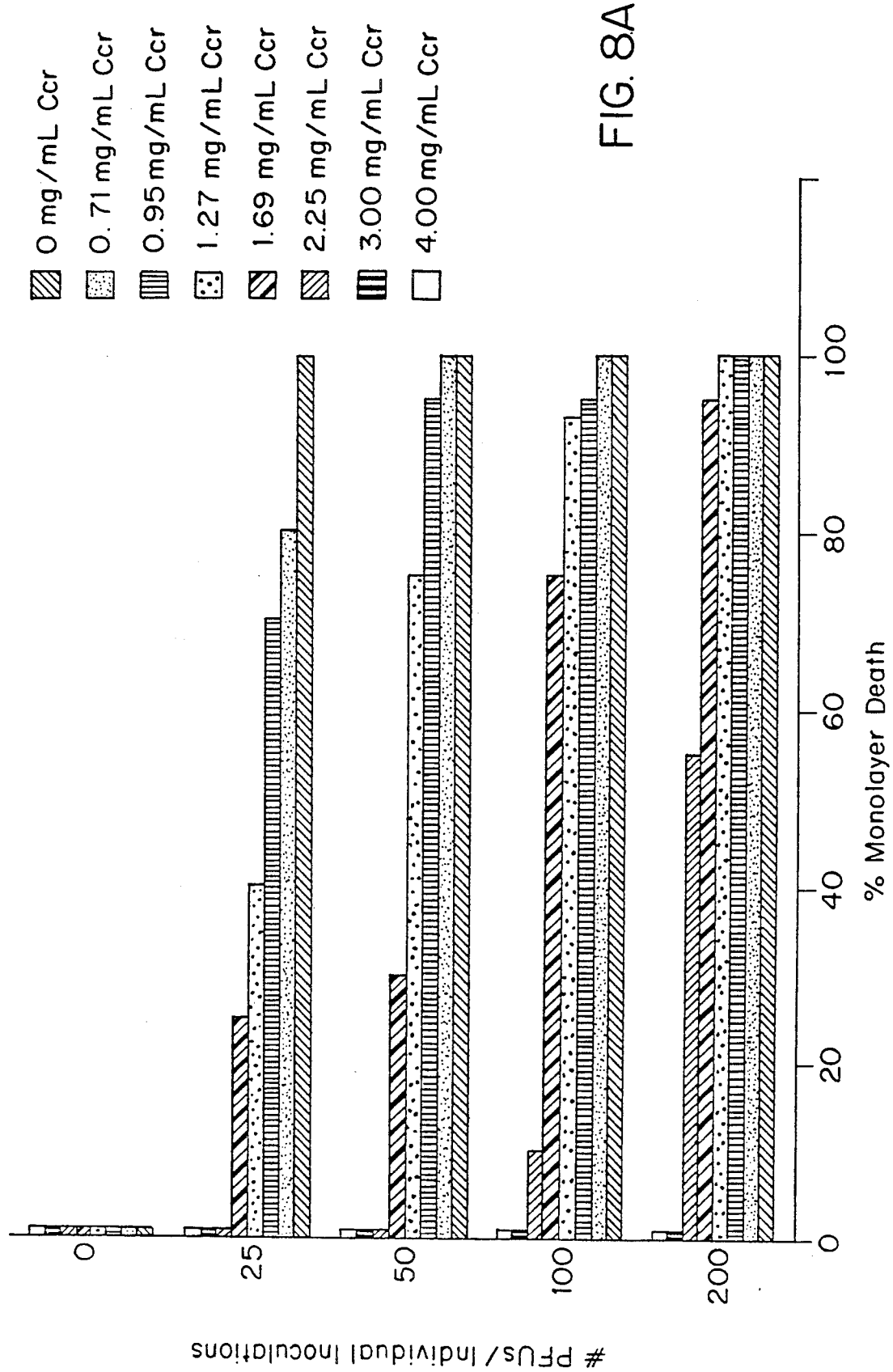
FIG. 8A is a bar graph depicting the effect of 8 different concentrations of cyclocreatine (bars from top to bottom for each inoculum: 4.0 mg/ml, 3.0 mg/ml, 2.25 mg/ml, 1.69 mg/ml, 1.27 mg/ml, 0.95 mg/ml, 0.71 mg/ml, 0 mg/ml) on the percent of monolayer cell i death of A549 cells inoculated with various amounts of HSV-2 virus. The bar graph illustrates the protective effect of cyclocreatine in A549 cells against the cytopathic effect of HSV-2 infection.
Figure 8B:
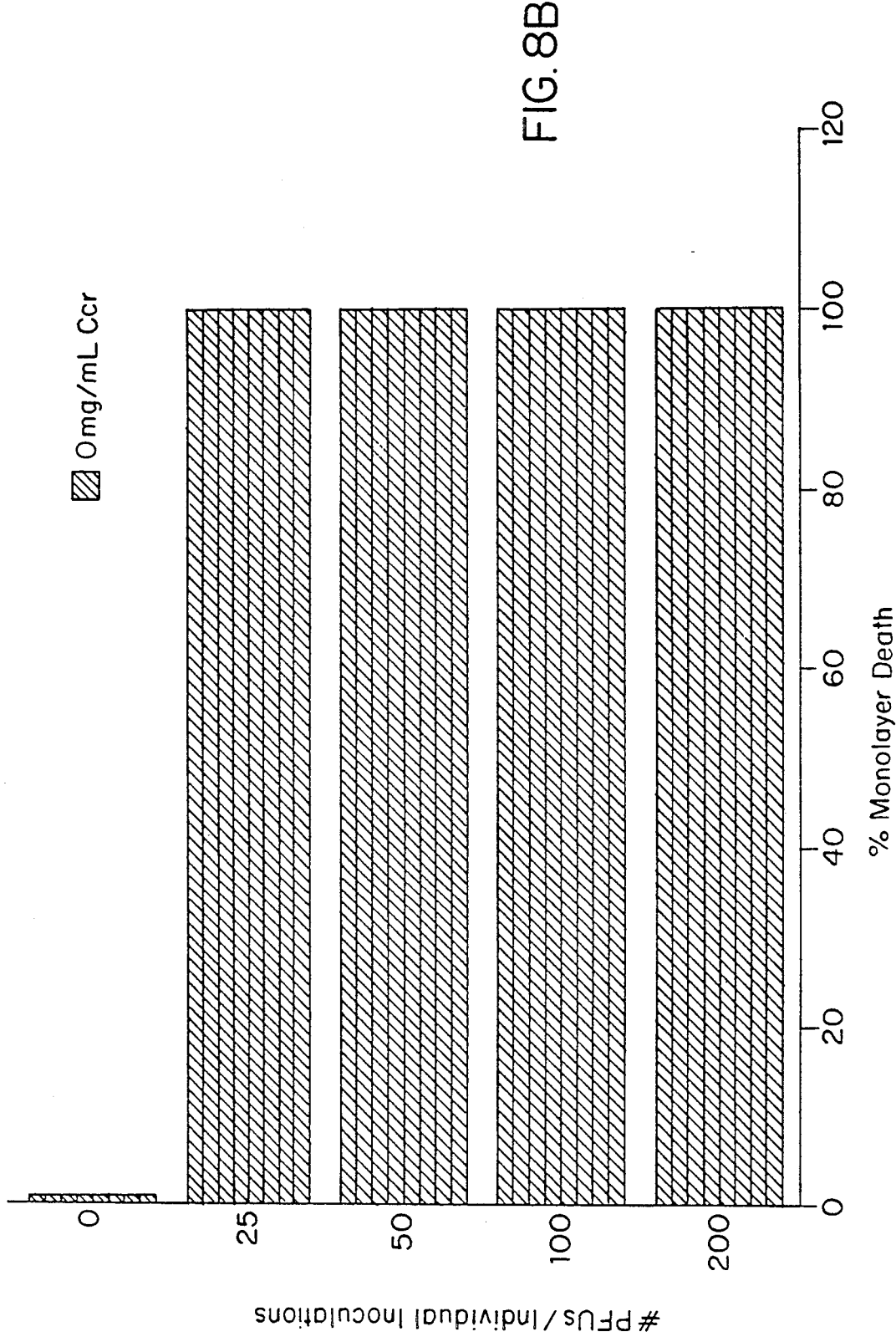
FIG. 8B is a bar graph depicting the effect of various amounts of HSV-2 virus on percent monolayer death in the absence of drug or cyclocreatine (8 wells/inoculum). The length of each bar represents the percent monolayer death in a single well.

FIGS. 7 and 8 show that cyclocreatine inhibited the cytopathic effect of various amounts of HSV-1 (FIG. 7A) and HSV-2 (FIG. 7B) in contact-inhibited A459 cells. The results of control experiments indicated that in the absence of cyclocreatine, most wells of contact-inhibited A459 cells that received a given inoculum of HSV-1 (FIG. 7B) or HSV-2 (FIG. 8B) had comparable levels of cell death.

The results of the experiments summarized in FIGS. 3-8 suggest that the antiviral effect of cyclocreatine observed against HSV-1 (FIG. 1) and HSV-2 (FIG. 2) in serum-starved Vero cells was not restricted to Vero cells. Slight variations in the efficacy of cyclocreatine against HSV-1 and HSV-2 in the different cell lines may not have been detected by this assay.

EXAMPLE 2

Plaquing Efficiency of HSV-1 in Vero Cells

Plaque Assay

Plaque assays were performed on confluent, serum-starved monolayers of Vero cells in 100 mm dishes (Corning). Growth medium was removed by aspiration and 10 ml of low serum media was added. Monolayers were grown in this medium for 5 days. After aspiration of this low-serum media, virus was incubated with the cells in 10 ml of serum-free media for 1 hour at 37° C. After incubation, the inoculum was removed by aspiration and replaced with 2 ml of agarose-medium maintained at 42° C. The agarose-medium overlay contained a fresh 1:1 mixture of: (a) 1% Seakem agarose (FMC Corp., Rockland, Me.) in tissue culture grade water (JRH Biosciences, Lenexa, Kans.) melted at 100° C. for 20 min; and (b) 2×MEM/20% FBS/4 mM L-glutamine/200 units/mL penicillin and 200 μg/ml streptomycin activity (JRH Biosciences). Viral plaques developed within 2-3 days.

To visualize plaques, monolayers were fixed with 5% formaldehyde for 45 min and then stained for 2 hours with 0.25% crystal violet in ethanol. Plaques were counted under a microscope at 40× magnification.

Antiviral Effect of Cyclocreatine Against HSV-1 in Serum-starved Vero Cells

A plaque assay was used to confirm the antiviral activity of cyclocreatine detected in the cytopathogenicity studies described above. Vero cells were grown in 100 mm dishes and were serum-starved. Each dish, with the exception of uninfected controls, was inoculated with HSV-1 virus and incubated with various concentrations of cyclocreatine until plaques appeared in the plates exposed to virus alone.

Figure 9:
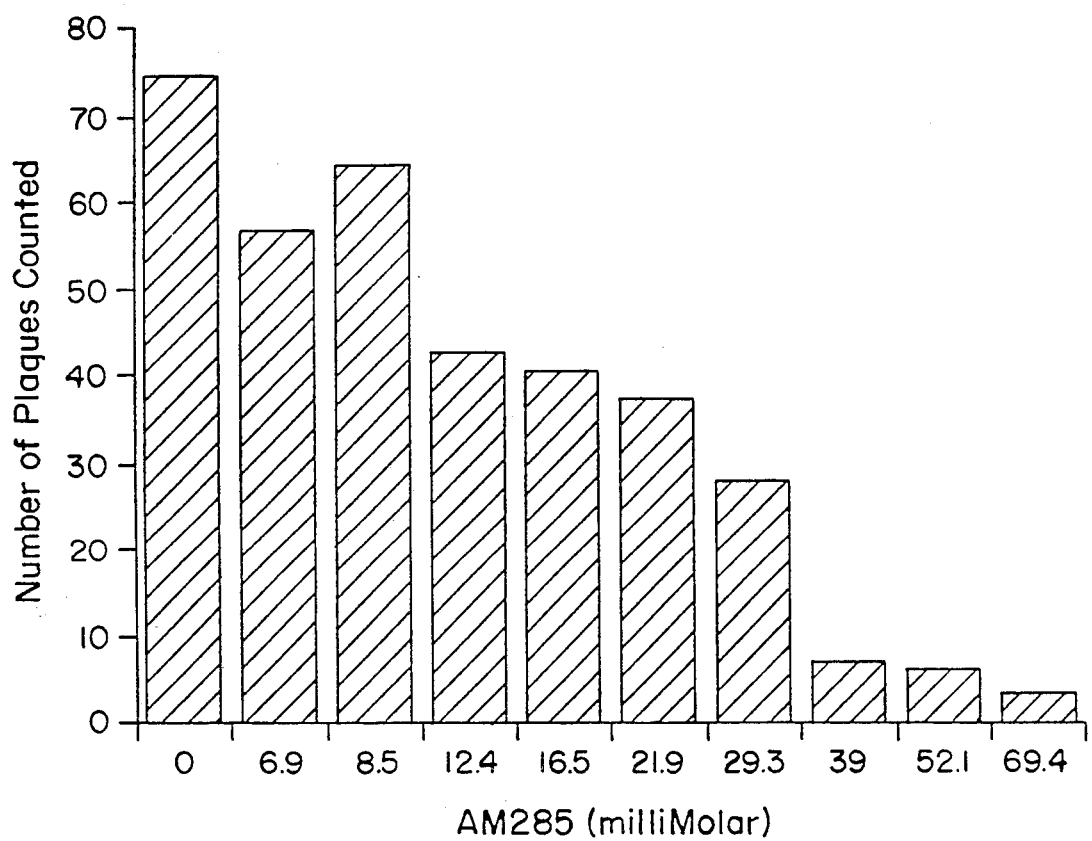
FIG. 9 is a bar graph illustrating the inhibitory effect of cyclocreatine (AM285) on the plaquing efficiency of HSV-1 in serum-starved Vero cells. The height of the bars represents the number of plaques observed for each concentration (mM) of cyclocreatine tested.

In FIG. 9, the number of plaques formed (y-axis) is plotted against the dose of cyclocreatine (AM285; x-axis). The histogram shows that cyclocreatine reduced the plaquing efficiency of HSV-1 in serum-starved Vero cells. As the dose increased, the number of plaques formed decreased. Plaque size was also diminished substantially in the presence of cyclocreatine (data not shown). In a second experiment, the number of plaques was observed to decrease from 755 (at 0 mg/ml cyclocreatine) to 120 (at 4 mg/ml cyclocreatine). The combination of the reduction of plaque number and size in cyclocreatine-treated dishes confirms the results of the CPE assay.

EXAMPLE 3

Treatment of Herpes Simplex Virus Type 2 Vaginitis in Mice with Cyclocreatine

Compounds 2.5%, 5% and 10% Cyclocreatine cream was made from dry cyclocreatine (lot AM285) and a polyethylene glycol (PEG) based cream (Squibb cream base #8) purchased from a local pharmacy. The positive control, acyclovir, was purchased as 5% acyclovir cream or in the oral formulation from a local pharmacy.

Infection

Swiss Webster female mice (Simonsen Labs, Gilroy, Calif.) weighing ~20-22 grams each at the start of the experiment were infected intravaginally with herpes simplex virus type 2 (HSV-2), strain E194. The vagina of each mouse was swabbed for 5 seconds with a cotton tip applicator dipped in 0.1N NaOH in order to irritate the vaginal area, and thereby facilitate infection. Approximately 1 hour later each vagina was dry swabbed 5 seconds. An applicator dipped in virus medium containing $10^5$–$10^6$ virus particles/ml was then used to swab each mouse for 20 seconds. The swabs were gently and slowly twisted back and forth during the time they were in place.

Treatment

Six hours after virus infection topical creams were applied inside and around the outside of the vaginal areas. Groups of mice were treated with 10%, 5% or 2.5% cyclocreatine cream, 5% acyclovir cream, or placebo cream. There were 10 mice in each group treated with cyclocreatine or acyclovir, and 25 mice in the group treated with the placebo. Treatments were given topically, three times daily, on days 1 through 7 after virus challenge.

Toxicity Controls

Groups of 5 mice were sham-infected using the process described above for virus infection, except that no virus was present for the final step. These mice were treated the same way and at the same times as above. Vaginal areas were examined daily for redness and irritation.

Parameters Used to Evaluate the Infection

Lesion scores in infected mice were determined daily on days 2-14 of the infection. A score of 1+ indicates redness immediately around the vagina. 2+ indicates spread of the lesion toward the anus. 3+ indicates a lesion (usually with swelling) from the vagina to the anus. 4+ indicates that the lesion has progressed around the anus. Because many of the mice subsequently died of the infection, the lesion score near the time of death was carried through to the end of 14 days. If this were not done, lesion scores in the placebo group would appear to go down as the most affected mice died. Some animals developed hind limb paralysis (and later died). This condition did not add to the lesion score.

In Vivo Activity of Cyclocreatine against HSV-2 Induced Vaginitis

Figure 10:
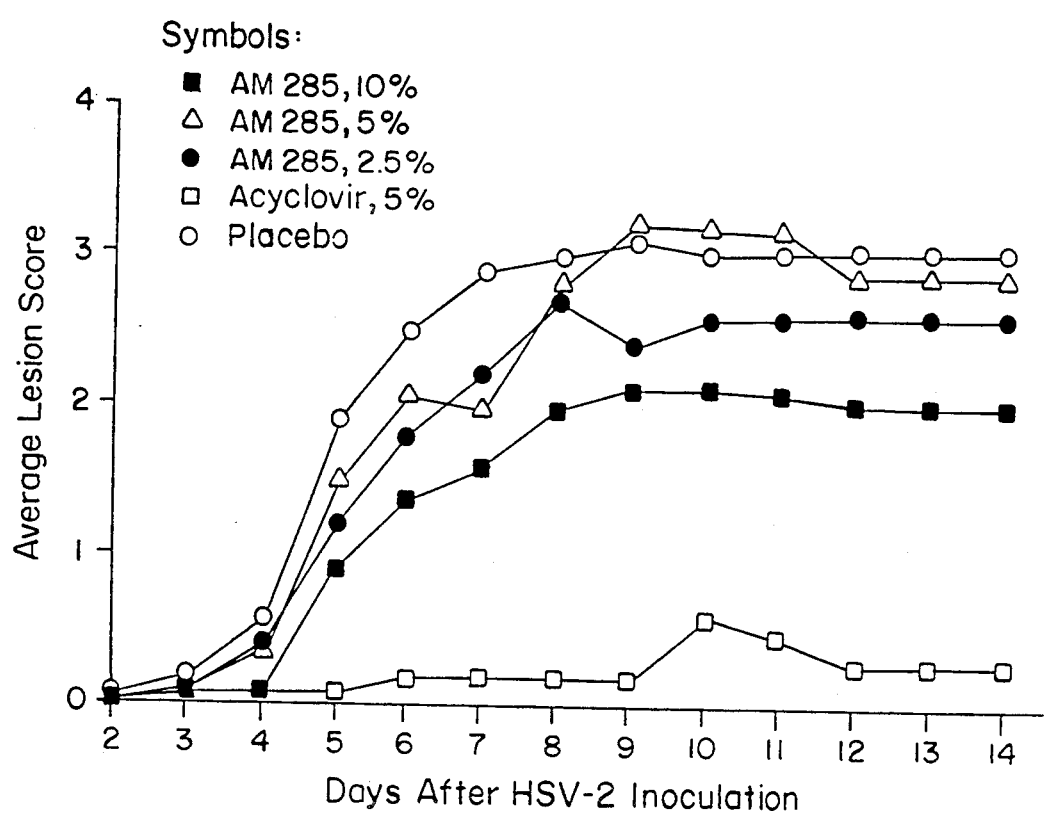
FIG. 10 is a graph illustrating the effect of cyclocreatine (AM285), acyclovir and placebo cream on HSV-2 genitalis in mice. The average lesion score is plotted against days after inoculation for 10% cyclocreatine cream (filled squares); 5% cyclocreatine cream (filled triangles); 2.5% cyclocreatine cream (filled circles); 5% acyclovir cream (open squares); and placebo cream (open circles).

To extend the in vitro findings of antiviral activity, cyclocreatine was tested in vivo in a mouse vaginitis model as described above. The degree of lesion inhibition by cyclocreatine and acyclovir were compared to the placebo control. FIG. 10 shows that, when applied topically to the vaginal area of an HSV-2 infected mouse, cyclocreatine slightly reduces the average lesion score compared to the placebo. Standard deviations and statistical significance of the data points are tabulated for the same experiment in Table 1. Although cyclocreatine showed some activity using the 10% cream, doses of 5% and 2.5% were inactive in this assay. As anticipated, acyclovir was very effective.

By criteria other than lesion score, there was little or no effect of cyclocreatine under these conditions. 10% cyclocreatine showed slight activity in increasing survival (40% compared to 16% in the placebo group), but the results were not statistically significant because of the small sample size.

TABLE 1

Effect of AM 285 Treatment on Herpes Simplex Virus Type 2 Vaginitis in Mice

| Day* | AM 285 10% | AM 285 5% | AM 285 2.5% | Acyclovir 5% | Placebo |
|---|---|---|---|---|---|
| 3 | 0.2 ± 0.2 | 0.3 ± 0.3 | 0.2 ± 0.2 | 0.1 ± 0.1 | 0.2 ± 0.3 |
| 4 | 0.1 ± 0.2[b] | 0.4 ± 0.4 | 0.4 ± 0.6 | 0.1 ± 0.1[b] | 0.6 ± 0.5 |
| 5 | 0.9 ± 1.2[a] | 1.5 ± 1.1 | 1.2 ± 1.3 | 0.1 ± 0.2[c] | 1.9 ± 1.4 |
| 6 | 1.4 ± 1.9 | 2.1 ± 1.6 | 1.8 ± 1.8 | 0.2 ± 0.2[c] | 2.5 ± 1.6 |
| 7 | 1.6 ± 1.9[a] | 2.0 ± 1.3 | 2.2 ± 1.8 | 0.2 ± 0.2[c] | 2.9 ± 1.5 |
| 8 | 2.0 ± 2.0 | 2.8 ± 1.8 | 2.7 ± 1.7 | 0.2 ± 0.3[c] | 3.0 ± 1.7 |
| 9 | 2.2 ± 1.9 | 3.2 ± 1.6 | 2.4 ± 1.9 | 0.2 ± 0.2[c] | 3.1 ± 1.6 |
| 10 | 2.2 ± 1.9 | 3.2 ± 1.5 | 2.6 ± 1.7 | 0.6 ± 0.8[c] | 3.0 ± 1.6 |
| 11 | 2.1 ± 1.9 | 3.1 ± 1.5 | 2.6 ± 1.7 | 0.5 ± 0.7[c] | 3.0 ± 1.6 |
| 12 | 2.0 ± 1.9 | 3.0 ± 1.5 | 2.6 ± 1.7 | 0.3 ± 0.6[c] | 3.0 ± 1.6 |
| 13 | 2.0 ± 1.9 | 3.0 ± 1.5 | 2.6 ± 1.7 | 0.3 ± 0.6[c] | 3.0 ± 1.6 |
| 14 | 2.0 ± 1.9 | 3.0 ± 1.5 | 2.6 ± 1.7 | 0.3 ± 0.6[c] | 3.0 ± 1.6 |
| Grand Ave. (Days 3-14) | 1.6 + 0.8[a] | 2.3 + 1.1 | 2.0 + 0.9 | 0.3 + 0.2[c] | 2.4 + 1.0 |

*after virus challenge
[a] $p < 0.05$ (two-tailed Student's $t$ test)
[b] $p < 0.01$ (two-tailed Student's $t$ test)
[c] $p < 0.001$ (two-tailed Student's $t$ test)

Results in the toxicity control showed that cyclocreatine was well-tolerated and caused no adverse effects to the vaginal area.

These results show that cyclocreatine at 10% concentration in PEG cream base had a moderate antiviral activity in this model. Acyclovir showed superior activity at 5% concentration. The topically applied acyclovir cream was only 2-fold lower in concentration than that of cyclocreatine, while the in vitro ED50 for acyclovir (7 μM) is 1000× lower than that of cyclocreatine (7 mM).

In a second experiment, cyclocreatine cream showed weak, but not statistically significant, activity in the mouse vaginitis model. However, in this experiment in which there were 20 mice in the placebo group, the average lesion score in the placebo group was lower and may have obscured the effect of cyclocreatine. Note that in this model, which requires topical application of drug, the concentration of the leading anti-Herpes agent, acyclovir, required for activity is relatively high.

Alternate modes of administration such as dietary or parenteral administration may be more effective. Another experiment was performed essentially as described above, with the following differences: (1) the inoculating applicator was dipped in virus medium having about $4 \times 10^6$ plaque forming units of virus per ml, (2) there were 20 mice in the group treated with the placebo, (3) acyclovir was administered orally by gavage twice daily, in half daily doses, for a period of 5 days, starting 24 hours after virus challenge, and (4) the cyclocreatine preparation (AM 285) was mixed into ground mouse chow to a final concentration of 1%, and feeding of the mixture began 3 days before virus inoculation and continued until day 14 after virus challenge. The results of this experiment, reported as average lesion score, are recorded in Table 2A. For comparison, acyclovir was administered alone, by garage. The lesion scores for animals treated with acyclovir alone are reported in Table 2B.

Figure 11:
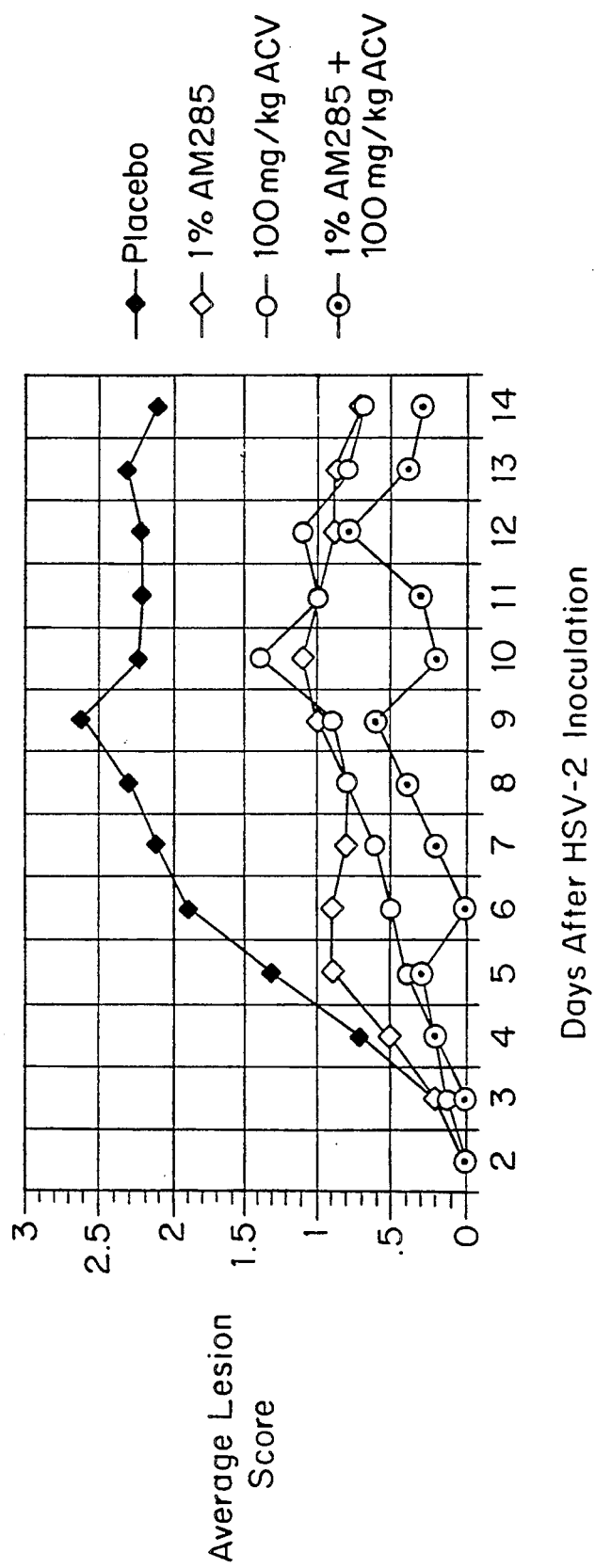
FIG. 11 is a graph illustrating the additive effect of dietary (1%) cyclocreatine (AM285) and 100 mg/kg acyclovir (ACV, administered by gavage) in a Herpes vaginitis model. In the graph, the average lesion score is plotted against the day after inoculation with HSV-2 for animals treated with placebo (filled diamonds), 1% cyclocreatine (AM285; open diamonds), 100 mg/kg acyclovir (ACV; open circles), or 1% cyclocreatine (AM285) and 100 mg/kg acyclovir (ACV) (filled circles).

AM 285 by itself showed an antiviral effect comparable to that achieved by acyclovir at 200 mg/kg, 100 mg/kg or 50 mg/kg. Acyclovir alone, administered at 25 mg/kg was less active. The combination of 1% dietary AM 285 and acyclovir (25 mg/kg or 50 mg/kg) achieved results comparable to AM 285 alone. However, the combination of 1% dietary AM 285 and 100 mg/kg of acyclovir produced a better response than acyclovir alone, which was important in terms of overall benefit to the animals (compare the results for 1% AM 285 alone (Table 2A), 100 mg/kg acyclovir (Table 2B), and 1% AM 285 plus 100 mg/kg acyclovir (Table 2A)). These results are also displayed in the form of a graph (FIG. 11). The data are consistent with an additive effect of cyclocreatine and acyclovir. Again, different doses and/or modes of administration for one or both drugs may uncover a synergistic effect such as that observed in vitro.

TABLE 2A

Effect of AM 285 and Acyclovir (ACV) Treatments on Herpes Simplex Virus Type 2 Vaginitis in Mice

| Day* | AM 25 1%[c] | AM 285 + ACV 100[#] | AM 285 + ACV 50 | AM 285 + ACV 25 | Placebo |
|---|---|---|---|---|---|
| 3 | 0.2 ± 0.2[@] | 0.0 ± 0.0 | 0.1 ± 0.2 | 0.1 ± 0.2 | 0.1 ± 0.2 |
| 4 | 0.5 ± 0.7 | 0.2 ± 0.2[a] | 0.2 ± 0.3[a] | 0.2 ± 0.3[a] | 0.7 ± 0.7 |
| 5 | 0.9 ± 1.3 | 0.3 ± 0.4 | 0.4 ± 0.4 | 0.4 ± 0.5 | 1.3 ± 1.5 |
| 6 | 0.9 ± 1.3 | 0.0 ± 0.0[b] | 0.3 ± 0.3[b] | 0.3 ± 0.4[a] | 1.9 ± 1.8 |
| 7 | 0.8 ± 1.4 | 0.2 ± 0.3[b] | 0.4 ± 0.5[b] | 0.6 ± 0.6[a] | 2.1 ± 1.8 |
| 8 | 0.8 ± 1.4[a] | 0.4 ± 0.4[b] | 0.4 ± 0.6[b] | 1.0 ± 1.0[a] | 2.3 ± 1.8 |
| 9 | 1.0 ± 1.3[a] | 0.6 ± 0.6[c] | 1.1 ± 1.5[a] | 1.4 ± 1.2[a] | 2.6 ± 1.5 |
| 10 | 1.1 ± 1.3 | 0.2 ± 0.4[b] | 1.1 ± 1.6 | 1.4 ± 1.3 | 2.2 ± 1.7 |
| 11 | 1.0 ± 1.3 | 0.3 ± 0.4[b] | 1.4 ± 1.6 | 1.4 ± 1.2 | 2.2 ± 1.8 |
| 12 | 0.9 ± 1.3 | 0.8 ± 0.5[b] | 1.2 ± 1.6 | 1.0 ± 1.2 | 2.2 ± 1.9 |
| 13 | 0.9 ± 1.4[a] | 0.4 ± 0.5[b] | 1.2 ± 1.6 | 1.0 ± 1.2 | 2.3 ± 1.8 |
| 14 | 0.7 ± 1.4[a] | 0.3 ± 0.7[b] | 1.1 ± 1.6 | 1.0 ± 1.2 | 2.1 ± 1.9 |
| Grand Ave. | 0.8 ± 0.2[c] | 0.3 ± 0.2[c] | 0.7 ± 0.5[c] | 0.8 ± 0.5[c] | 1.8 ± 0.7 |

TABLE 2A-continued

Effect of AM 285 and Acyclovir (ACV) Treatments on Herpes Simplex Virus Type 2 Vaginitis in Mice

| Day* | AM 25 1%[e] | AM 285 + ACV 100[#] | AM 285 + ACV 50 | AM 285 + ACV 25 | Placebo |
|---|---|---|---|---|---|
| (Days 3–14) | | | | | |

*after virus challenge
[e]Percentage of cyclocreatine mixed directly with ground-up mouse chow. Feeding began 3 days before virus inoculation and continued until day 15 after virus challenge.
[#]Mg/kg/day given in half daily doses twice daily for 5 days starting 24 hours after virus challenge.
[@]Standard deviation.
[a]$p < 0.05$ (two-tailed Student's t test)
[b]$p < 0.01$ (two-tailed Student's t test)
[c]$p < 0.001$ (two-tailed Student's t test)

TABLE 2B

Effect of Acyclovir (ACV) Treatment on Herpes Simplex Virus Type 2 Vaginitis in Mice
Average Lesion Score

| Day* | ACV 200 mg/kg[#] | ACV 100 mg/kg | ACV 50 mg/kg | ACV 25 mg/kg | Placebo |
|---|---|---|---|---|---|
| 3 | 0.1 ± 0.2[@] | 0.1 ± 0.2 | 0.0 ± 0.0 | 0.1 ± 0.2 | 0.1 ± 0.2 |
| 4 | 0.1 ± 0.2[a] | 0.2 ± 0.3[a] | 0.2 ± 0.3[a] | 0 5 ± 0.7 | 0.7 ± 0.7 |
| 5 | 0.4 ± 0.5 | 0.4 ± 0.4 | 1.0 ± 1.8 | 1.3 ± 1.5 | 1.3 ± 1.5 |
| 6 | 0.2 ± 0.3[b] | 0.5 ± 0.5[a] | 0.5 ± 0.7[a] | 1.3 ± 1.3 | 1.9 ± 1.8 |
| 7 | 0.4 ± 0.5[b] | 0.6 ± 0.7[a] | 0.8 ± 1.2[a] | 1.7 ± 1.6 | 2.1 ± 1.8 |
| 8 | 0.7 ± 0.6[a] | 0.8 ± 0.9[a] | 0.8 ± 0.9[a] | 2.1 ± 1.5 | 2.3 ± 1.8 |
| 9 | 0.9 ± 0.7[b] | 0.9 ± 0.9[b] | 1 1 ± 1.0[b] | 2.1 ± 1.4 | 2.6 ± 1.5 |
| 10 | 1.0 ± 0.6[a] | 1.4 ± 1.2 | 0.9 ± 1.2[a] | 2.0 ± 1.2 | 2.2 ± 1.7 |
| 11 | 0.7 ± 0.7[a] | 1.0 ± 1.3 | 0.9 ± 1.2[a] | 1.9 ± 1.3 | 2.2 ± 1.8 |
| 12 | 0.7 ± 0.7[a] | 1.1 ± 1.3 | 0.9 ± 1.2[a] | 1.9 ± 1.4 | 2.2 ± 1.9 |
| 13 | 0.8 ± 0.7[a] | 0.8 ± 0.9[a] | 1 0 ± 1.2[a] | 1.8 ± 1.5 | 2.3 ± 1.8 |
| 14 | 0.7 ± 0.7[a] | 0.7 ± 0.9[a] | 1.0 ± 1.3[a] | 1.8 ± 1.5 | 2.1 ± 1.9 |
| Grand Ave. (Days 3–14) | 0.6 ± 0.3 | 0.7 ± 0.4[c] | 0.8 ± 0.3[c] | 1.5 ± 0.6 | 1.8 ± 0.7 |

*after virus challenge
[#]Mg/kg/day given in half daily doses twice daily for 5 days starting 24 hours after virus challenge.
[@]Standard deviation.
[a]$p < 0.05$ (two-tailed Student's t test)
[b]$p < 0.01$ (two-tailed Student's t test)
[c]$p < 0.001$ (two-tailed Student's t test)

AM 285 was well-tolerated in the diet. Groups of 5 mice were treated with one or both drugs under the same regimen as the virus-infected mice. Table 2C depicts the overall survival of infected and toxicity control mice. There were a few more survivors in the groups treated with both compounds compared to the groups treated with acyclovir alone. Of the animals treated with 1% AM 285 and 100 mg/kg of acyclovir, all survived. The toxicity control animals were weighed on day 0 and day 15 of the experiment. Results of weight changes over 15 days suggest that cyclocreatine may actually promote weight gain in mice relative to mice receiving only normal chow. However, since the animals were not weighed individually, a statistical interpretation of the data cannot be made and further experiments are required to confirm the observation.

EXAMPLE 4

Synergism of Cyclocreatine and Acyclovir Against HSV-1 and HSV-2 Cytopathogenicity Because the antiviral effect of cyclocreatine represents the discovery of a novel class of antiviral agent it was of interest to test for synergism of cyclocreatine with a representative of another, common class of antiviral agent: nucleoside analogs. Cyclocreatine (AM285) and acyclovir were used alone and in combination to determine whether they could act synergistically to inhibit HSV-induced cytopathogenicity. Cytopathic Effect studies with each drug alone or in combination were performed in serum-starved Vero cells as described in Example 1, except that no agar overlay was used.

TABLE 2C

Effect of AM-285 and Acyclovir (ACV) Treatment on Survival in Mice Infected Intravaginally with HSV-2

| Compound (Dose) | Survivors/Total (%) | |
|---|---|---|
| Virus infected Group | | Mean Day to Death |
| ACV (25 mg/kg) | 5/10 (50) | 10.4 ± 2.5[@] |
| ACV (50 mg/kg) | 7/10 (70) | 11.3 ± 2.1 |
| ACV (100 mg/kg) | 8/10 (80) | 12.0 ± 1.4 |
| ACV (200 mg/kg) | 7/10 (70) | 11.3 ± 2.5 |
| AM-285 (1%) | 8/10 (80) | 6.0 ± 0.0 |
| AM-285 (1%) + 25 mg/kg ACV | 7/10 (70) | 12.7 ± 0.6 |
| AM-285 (1%) + 50 mg/kg ACV | 8/10 (80) | 14.5 ± 3.5 |
| AM-285 (1%) + 100 mg/kg ACV | 10/10 (100)[a] | >21 |
| Placebo | 8/20 (40) | 9.2 ± 3.2 |
| Uninfected Toxicity Controls | | Weight Change (g)* |
| ACV (25 mg/kg) | 5/5 (100) | 2.8 |

TABLE 2C-continued

Effect of AM-285 and Acyclovir (ACV) Treatment on
Survival in Mice Infected Intravaginally with HSV-2

| Compound (Dose) | Survivors/Total (%) | |
|---|---|---|
| ACV (50 mg/kg) | 5/5 (100) | 4.0 |
| ACV (100 mg/kg) | 5/5 (100) | 3.5 |
| ACV (200 mg/kg) | 5/5 (100) | 4.8 |
| AM-285 (1%) | 5/5 (100) | 7.8 |
| AM-285 (1%) + 25 mg/kg ACV | 5/5 (100) | 6.8 |
| AM-285 (1%) + 50 mg/kg ACV | 5/5 (100) | 9.0 |
| AM-285 (1%) + 100 mg/kg ACV | 5/5 (100) | 7.0 |
| Placebo | 5/5 (100) | 5.1 |

@Standard deviation.
*Difference between combined animal weights on day 0 and day 15 of infection.
$^o$p < 0.05 (two-tailed Fisher exact test [survival] or two-tailed Student's t test [mean day to death]).

Figure 12:
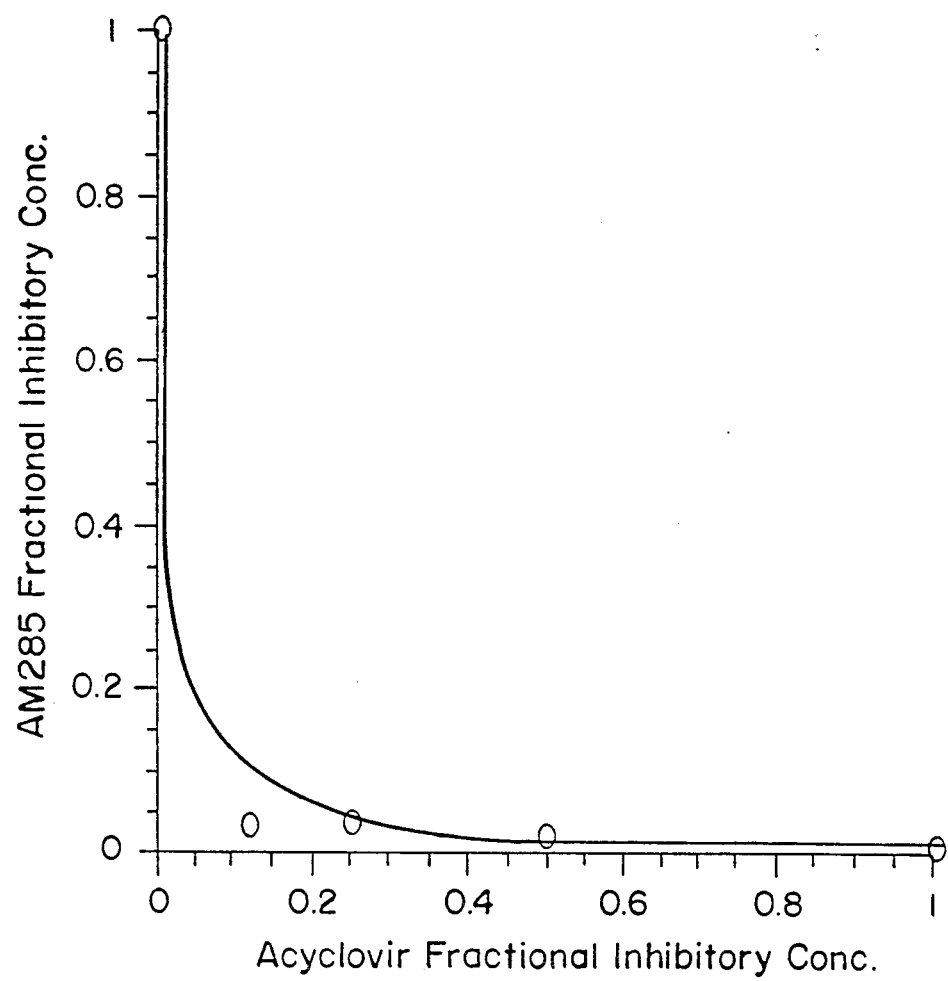
FIG. 12 is a graph illustrating the synergistic effect of cyclocreatine and (AM285) and acyclovir on the cytopathic effect of HSV-1 grown in serum-starved Vero cells. The concentration of cyclocreatine or acyclovir required to inhibit the virus-induced cytopathic effect by 65% was determined and taken as a fractional inhibitory concentration of 1.0. Fractional inhibitory concentrations of each drug were combined and combinations that inhibited cytopathogenicity of HSV-1 by 65% were plotted.
Figure 13:
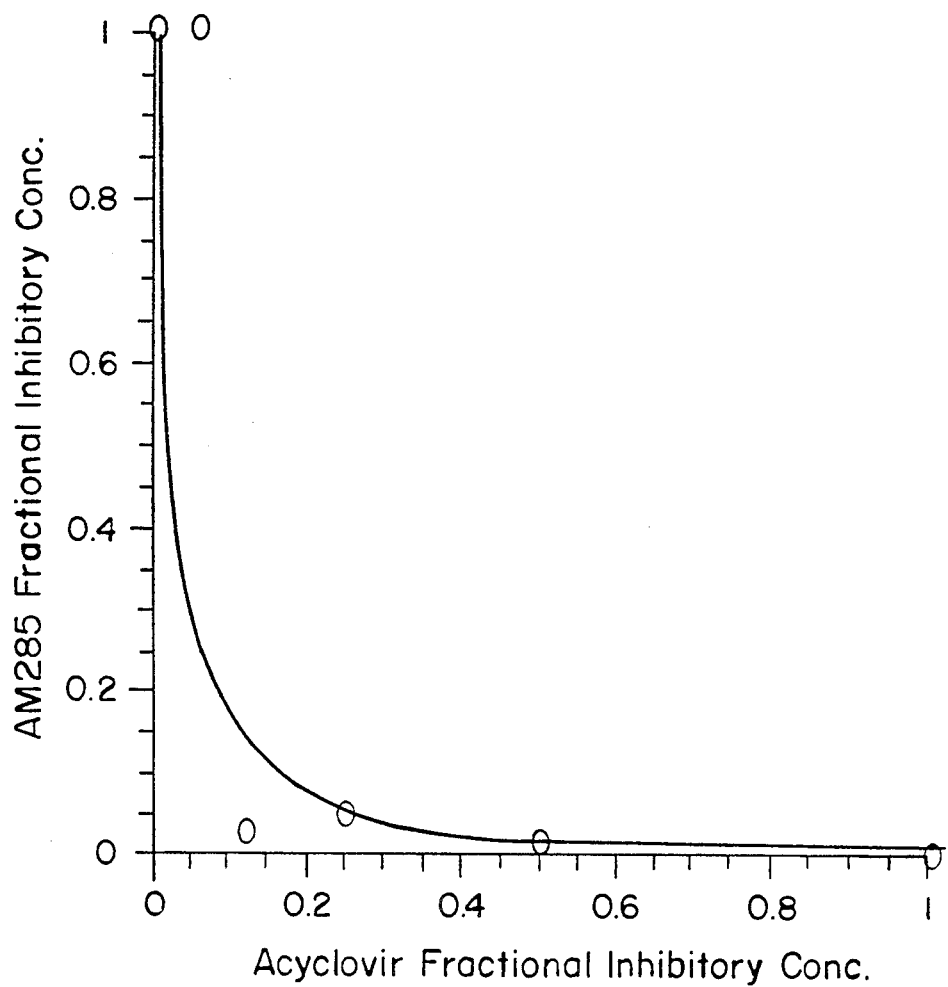
FIG. 13 is a graph illustrating the synergistic effect of cyclocreatine (AM285) and acyclovir on the cytopathic effect of HSV-2 grown in serum-starved Vero cells. The concentration of cyclocreatine or acyclovir required to inhibit the cytopathic effect by 60% was determined and taken as a fractional inhibitory concentration of 1.0. Fractional inhibitory concentrations of each drug were combined and combinations that inhibited cytopathogenicity of HSV-2 by 60% were plotted.
Figure 14:
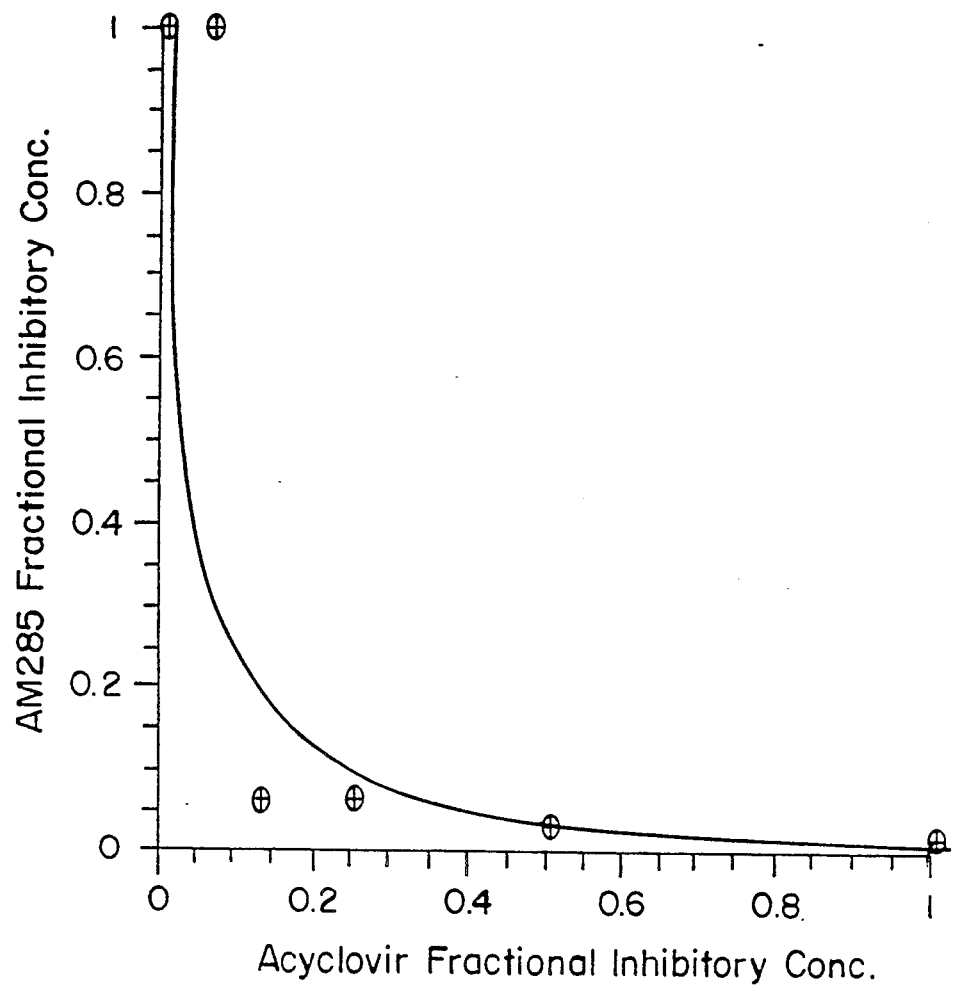
FIG. 14 is a graph illustrating the synergistic effect of cyclocreatine (AM285) and acyclovir on the cytopathic effect of HSV-2 grown in serum-starved Vero cells. The concentration of cyclocreatine or acyclovir required to inhibit the cytopathic effect by 70% was determined and taken as a fractional inhibitory concentration of 1.0. Fractional inhibitory concentrations of each drug were combined and combinations that inhibited cytopathogenicity of HSV-2 by 70% were plotted.

FIGS. 12-14 show that cyclocreatine and acyclovir, the leading antiherpes nucleoside analog, can synergistically inhibit the cytopathic effects of HSV-1 and HSV-2 in serum-starved Vero cells. Data are presented in the form of an isobologram, as the fractional inhibitory concentrations of each drug required alone or in combination to achieve a pre-determined anti-vital endpoint. When given alone, the fractional inhibitory concentration required to achieve a selected endpoint is 1.0. When administered in combination with another drug, less drug may be required to achieve the same effect. An additive effect of the drugs would give a straight line between the points defined by (x=0, y=1) and (x=1, y=0). A synergistic effect is indicated when the data give a line which dips below this line.

For FIG. 12, the doses of cyclocreatine (AM285) and acyclovir required to inhibit HSV-1 induced cytopathogenicity by 65% were determined to be 35 mM and 0.97 μM, respectively. Fractional inhibitory concentrations of each drug were combined and those combinations which inhibited cytopathogenicity by 65% were plotted in FIG. 20.

The concentrations of cyclocreatine (AM285) or of acyclovir required to inhibit HSV-2 induced cytopathogenicity by 60% or 70% were determined to be 35 mM and 1.95 μM, respectively. Fractional inhibitory concentrations were used in combination and the combinations which resulted in 60% or 70% inhibition were plotted in FIG. 13 (60% inhibition endpoint) and FIG. 14 (70% inhibition endpoint). For each experiment recorded in FIGS. 12-14, the resulting isobologram suggests synergism.

The results of these experiments support the hypothesis that cyclocreatine represents a different class of antiviral agent than that of nucleotide analogs. Furthermore, cyclocreatine can be used clinically in combination with such nucleotide analogs to increase their potency and/or decrease their toxicity.

Under the conditions of the mouse vaginitis model discussed above, a synergistic effect of cyclocreatine and acyclovir was not observed in one set of experiments in which a topically applied cream containing 10% cyclocreatine and 2%, 1% or 0.5% acyclovir was used. In another experiment in which animals were fed mouse chow containing 1% cyclocreatine and acyclovir was administered by gavage (see above), an additive effect of acyclovir and cyclocreatine was observed. Additional experiments using different formulations or routes of administration (e.g., parenteral), for example, may be required to observe a synergistic effect in vivo.

EXAMPLE 5

In Vitro Activity of Cyclocreatine Against Other Viruses

To determine the generality of the antiviral effect of cyclocreatine against other viruses, inhibition of cypathogenicity induced by Vesicular Stomatitis virus, Influenza A and B, Pseudorabies virus, Varicella-Zoster virus, cytomegalovirus, and adenovirus was tested. Under the conditions used, human and guinea pig cytomegalovirus, Varicella-Zoster virus and adenovirus were notably affected by cyclocreatine.

Antiviral Activity of Cyclocreatine Against Adenovirus

Adenovirus type 5 was obtained from the ATCC. DU 145 cells were obtained from the American Type Culture Collection. Cells were infected with virus and cyclocreatine was assayed for antiviral activity using the cytopathic effect (CPE) assay essentially as described in Example 1.

Figure 15A:
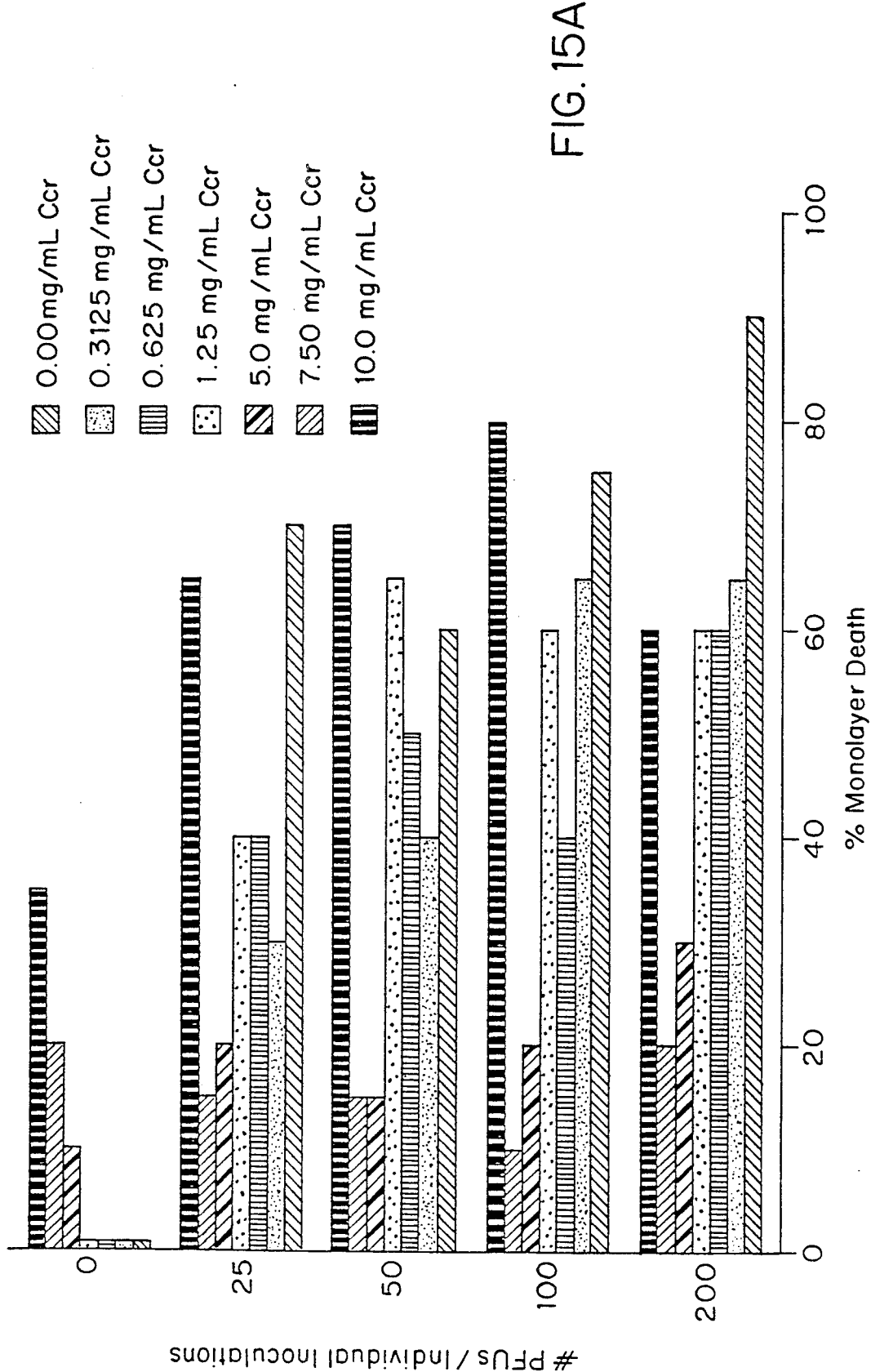
FIG. 15A is a bar graph depicting the effect of seven different concentrations of cyclocreatine (bars from top to bottom for each inoculum: 10.0 mg/ml, 7.5 mg/ml, 5.0 mg/ml, 1.25 mg/ml, 0.625 mg/ml, 0.3125 mg/ml, 0 mg/ml) on the percent of monolayer cell death of DU 145 cells inoculated with various amounts of adenovirus. The bar graph illustrates the protective effect of cyclocreatine in DU145 cells against the cytopathic effect of adenovirus infection.
Figure 15B:
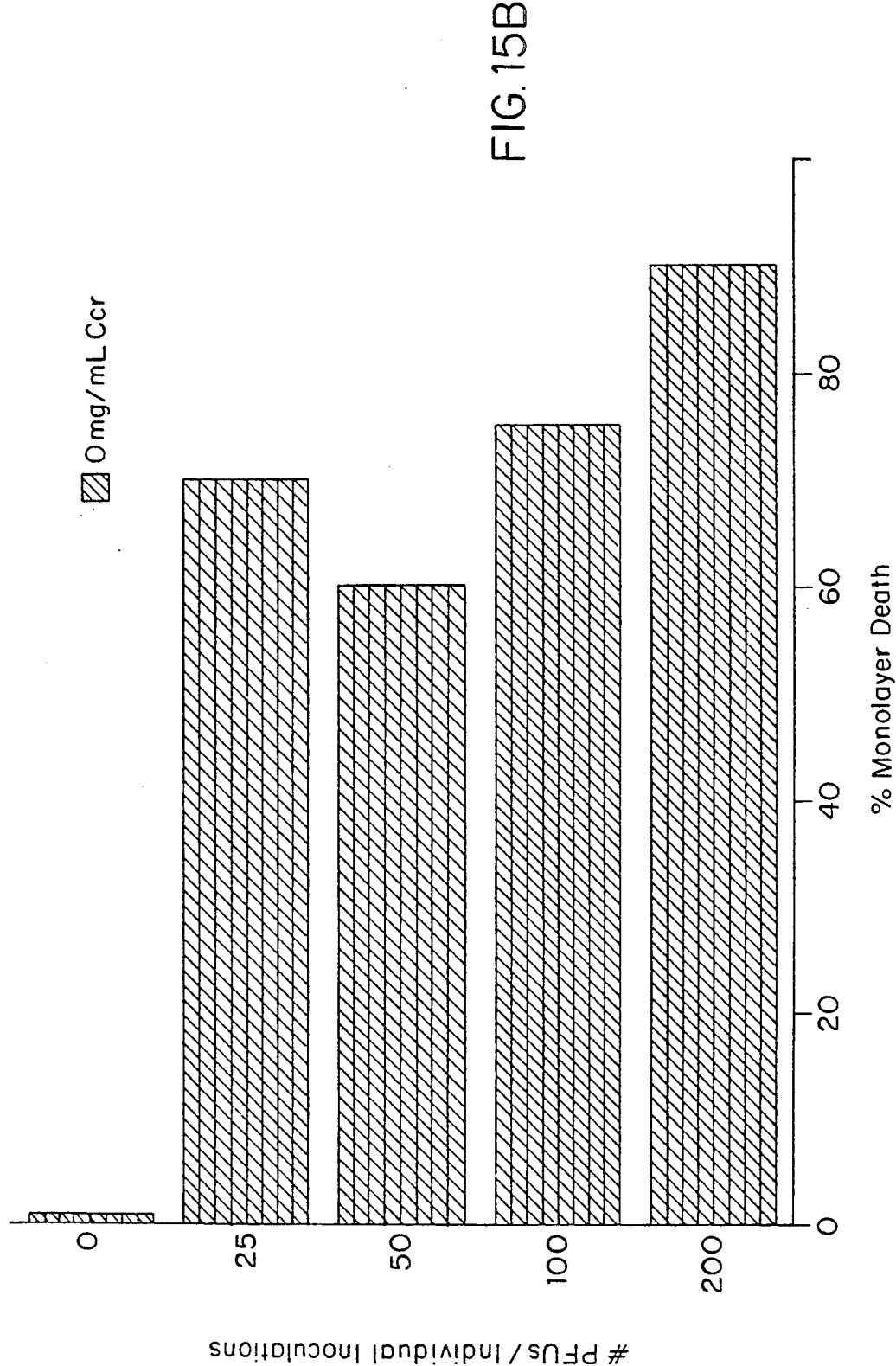
FIG. 15B is a bar graph depicting the effect of various amounts of adenovirus on the percent monolayer death in the absence of drug or cyclocreatine (8 wells/inoculum). The length of each bar represents the percent monolayer death in a single well.

FIG. 15 shows the results of a cytopathogenicity study with adenovirus in DU 145 cells. The percentage of monolayer death observed (x-axis) in each well at different concentrations of cyclocreatine (denoted by different shaded bars; from top to bottom for each inoculum: 10 mg/ml, 7.5 mg/ml, 5.0 mg/ml, 1.25 mg/ml, 0.625 mg/ml, 0.3125 mg/ml, 0.0 mg/ml) is plotted for a range of viral inoculla (y-axis; plaque-forming units (PFUs) per inoculum). FIG. 15A shows that, at varying concentrations of virus inoculla, cyclocreatine inhibited the cytopathic effect of adenovirus in DU 145 cells. A dose response to cyclocreatine was evident, although some cytotoxicity was observed at the highest concentration of drug (10 mg/ml; FIG. 15A, percent monolayer death in the absence of viral infection (O PFUs)). The results from the no drug control plate shown in FIG. 15B indicate that in the absence of cyclocreatine, most wells of DU 145 cells that receive a given inoculum of adenovirus display comparable levels of cell death.

Assay for Antiviral Activity of Cyclocreatine Against Influenza A, Influenza B, Parainfluenza Virus, Pseudorabies and Vesicular Stomatitis Virus

Viruses

Influenza A/Port Chalmers/1/73 ($H_3N_2$) and Vesicular stomatitis virus (VSV), Indiana strain, were obtained from the ATCC (Rockville, Md.). Influenza B/Hong Kong/5/72 was provided by Dr. Marion T. Coleman of the WHO International Influenza Center for the Americas. Parainfluenza Type 3 (PIV-3), strain C243, was obtained from the Southern Research Institute, Birmingham, Ala. Pseudorabies virus, Aujeszky strain, was obtained for Dr. Albert Kaplan, Albert Einstein Center, Philadelphia Pa. The titers of the viruses used for cytopathic effect studies, expressed as cell culture infectious dose, 50% endpoint ($CCID_{50}$), were determined to be $1 \times 10^{1.5}$ $CCID_{50}$/well for Influenza virus A and B, $1 \times 10^{2.5}$ $CCID_{50}$/well for Parainfluenza virus, $1 \times 10^2$ $CCID_{50}$/well for Pseudorabies virus, and $1 \times 10^2$ $CCID_{50}$/well for VSV.

Cells and Growth Media

BHK-21 cells (a continuous line of Syrian hamster kidney cells), MDCK cells (a continuous line of canine kidney cells), MDBK cells, (a continuous line of bovine kidney cells), HEp-2 cells (a continuous line of cells derived from an epidermoid carcinoma of a human larynx), and Vero cells (a continuous line of African green monkey kidney cells), were obtained from the American Type Culture Collection (ATCC, Rockville, Md.).

Growth medium for the cells was as follows. None of the media contained antibiotics.

BHK-21 cells: Eagle's Minimum Essential Medium with non-essential amino acids (MEM; GIBCO, BRL) with 9% FBS and 0.1% $NaCO_3$.

MDCK cells: MEM, with 5% FBS, and 0.1% $NaHCO_3$.

MDBK cells: EMEM with non-essential amino acids (GIBCO, BRL), 5% Fetal bovine serum (FBS), 0.1% $NaHCO_3$.

HEp-2 cells: EMEM with non-essential amino acids (GIBCO BRL), 10% FBS, 0.1% $NaHCO_3$.

Vero cells: MEM with 5% FBS, 0.1% $NaCO_3$.

Test medium for VSV contained MEM, 2% FBS, 0.18% $NaHCO_3$, 50 μg/ml gentamicin and test medium for Influenza A and B contained MEM (without FBS, 0.18% $NaHCO_3$), 20 μg/ml trypsin, 2 μg/ml EDTA, 50 μg/ml gentamicin. Test medium for PIV-3 dilution was MEM, 2% FBS, 0.18% $NaHCO_3$, and 50 μg/ml gentamicin.

CPE-Reduction Assay

Cyclocreatine was prepared at a concentration of 100 mg/ml in MEM, without serum, 0.18% $NaHCO_3$, 50 μg/ml gentamicin. Further dilutions (2-fold dilution scheme) were made in MEM without serum.

Cells (0.2 ml/well) were seeded in 96-well flat bottom tissue culture plates, (Corning Glass Works, Corning, N.Y.). The cells were incubated overnight in order to establish cell monolayers. Growth medium was decanted from the 96-well plates and various dilutions of compound were added to wells of the plate (4 wells/dilution; 0.1 ml/well). Medium alone was added to uninfected cell and virus (no drug) control wells (0.1 ml/well). Virus, diluted in test medium (0.1 ml final volume), was added to all compound test wells of the plate (3 wells/dilution) and to 9 virus control wells. Test medium (0.1 ml/well) without virus was added to all toxicity control wells (1 well/dilution for each compound tested) and to 3 uninfected cell control wells.

The plates were incubated at 37° C. until virus control wells (no drug) had CPE readings near 100% CPE. Cells were then examined microscopically for virus CPE and graded on a scale of 0–4, with 0 being no CPE and 4 being 100% CPE. The cells in toxicity control wells were observed microscopically and graded for morphological changes due to cytotoxicity. Effective dose, 50% endpoint (ED50) and cytotoxic dose, 50% endpoint (CD50) were calculated by regression analysis from the CPE data and the toxicity control data, respectively. The ED50 is that concentration of antiviral substance which is calculated to produce a CPE grade half-way between that of the cell controls (0) and that of the virus controls when the CPE is read. CD50 is that concentration of substance calculated to be half-way between the concentration which produces no visible effect on the cells and the concentration which produces complete cytotoxicity.

Effect of Cyclocreatine on CPE of VSV, Pseudorabies Virus, Influenza A, Influenza B and Parainfluenza The reduction of cytopathic effect of VSV by cyclocreatine (4 mg/ml, 2 mg/ml, 1 mg/ml, 500 μg/ml, 250 μg/ml, 125 μg/ml, 62.5 μg/ml, and 0 μg/ml) was assayed in Vero cells and in BHK-21 cells. Cyclocreatine treatment did not lead to a reduction in CPE under the conditions used, and yielded the same grade (4.0) as the no drug controls. Ribavirin (ICN Pharmaceuticals, Costa Mesa, Calif.), diluted in the same medium and tested in parallel, had only a moderate effect on the virus.

The reduction of cytopathic effect of Pseudorabies virus by cyclocreatine (4 mg/ml, 2 mg/ml, 1 mg/ml, 500 μg/ml, 250 μg/ml, 125 μg/ml, 62.5 μg/ml, and 0 μg/ml) was assayed in MDBK cells, using the CPE assay described above. Cyclocreatine treatment yielded approximately the same grade (3.8 to 4.0) as the no drug controls (3.9) under the conditions used. Ribavirin (ICN Pharmaceuticals, Costa Mesa, Calif.), diluted in the same medium and tested in parallel against Pseudorabies virus, had an inhibitory effect ranging from a grade of 0.0 to 3.8 over a concentration range of 1.0 μg/ml to 1000 μg/ml ribavirin. DHPG was less effective than ribavirin, and acyclovir and adenine arabinoside were ineffective against this virus in a similar assay.

The reduction of cytopathic effect of Influenza A or of Influenza B by cyclocreatine (4 mg/ml, 2 mg/ml, 1 mg/ml 500 μg/ml, 250 μg/ml, 125 μg/ml and 62.5 μg/ml) was assayed in MDCK cells. Under the conditions used, cyclocreatine had a slight inhibitory effect on influenza B virus only; however, inhibition was only observed at the highest concentration used. In contrast, ribavirin (less than 10 μg/ml) was effective against each virus.

The reduction of cytopathic effect of parainfluenza type 3 by cyclocreatine (10 mg/ml, 5 mg/ml, 2.5 mg/ml, 1.25 mg/ml, 625 μg/ml, 213 μg/ml, 156 μg/ml, and 0 μg/ml) was assayed in HEp-2 cells. Under the conditions used, cyclocreatine had a slight inhibitory effect on PIV-3. At concentrations between 156 μg/ml and 2.5 mg/ml, the average CPE ranged from 3.5 to 3.7 compared with an average control CPE of 3.8. At higher concentrations, an antiviral effect was seen (10 mg/ml, average CPE 0.5; 5 mg/ml, average CPE 2.8), but some cytotoxicity was observed (visible cytotoxicity rated at 40 and 20, respectively).

Antiviral Activity of Cyclocreatine against GPCMV

GPCMV strain 22122 was provided by Dr. Briggitte Griffith, Veteran's Administration Medical Center, New Haven Conn. GPE cells, a continuous cell line of guinea pig embryo cells, established from primary guinea pig embryo cells were obtained from Whittaker M.A. Bioproducts, Walkersville, Md., and were grown in Eagle's minimum essential medium with non-essential amino acids, 10% FBS, and 0.05% NaHCO3 (without antibiotics).

The antiviral effect of cyclocreatine against Guinea Pig Cytomegalovirus (GPCVM) strain 22122 was determined in GPE cells using the CPE reduction assay described in this example. The titer of virus, expressed as cell culture infectious dose, 50% endpoint ($CCID_{50}$) was $1 \times 10^2$ $CCID_{50}$/well for GPCMV. An inhibitory effect by cyclocreatine was observed at concentrations between 0.625 and 5.0 mg/ml. The results of this experiment are recorded in Table 3.

In Vitro Antiviral Activity of Cyclocreatine Against Human Cytomegalovirus

Virus Strains

Human Cytomegalovirus (HCMV), strain AD-169, was obtained from the ATCC (Rockville, Md.). HCMV Strain C8704 (DHPG Resistant) and HCMV Strain C8805-37 (DHPG Resistant) were obtained from Dr. Karen Biron (Burroughs-Wellcome Co., Research Triangle Park, N.C.).

TABLE 3

Antiviral Activity (CPE Reduction) of Cyclocreatine (AM-285) or DHPG vs Guinea Pig Cytomegalovirus, Strain 22122, in GPE Cells

| | AM-285 | | | DHPG | |
|---|---|---|---|---|---|
| Conc. (μg/ml) | Visible Cyto-toxicity | Average CPE | Conc. (μg/ml) | Visible Cyto-toxicity | Average CPE |
| 10000 | 40 | 0.0 | 1000 | 40 | 0 |
| 5000 | 20 | 1.7 | 320 | 0 | 0 |
| 2500 | 20 | 2.5 | 100 | 0 | 0 |
| 1250 | 0 | 3.3 | 32 | 0 | 0.7 |
| 625 | 0 | 3.5 | 10 | 3.5 | |
| 312.5 | 0 | 4.0 | 3.2 | 0 | 4.0 |
| 156.25 | 0 | 4.0 | 1.0 | 0 | 4.0 |
| 0 | Average CPE 4.0 (virus controls, 8 days) | | | | |
| $ED50^a$(μg/ml): | 3271 | | | 18.4 | |
| $CD50^b$(μg/ml): | >10000 | | | >1000 | |
| $TI50^c$: | >3.0 | | | >54 | |

$^a$The concentration at which the average CPE is reduced to 50% of that seen in the virus controls (Effective Dose, 50% endpoint).
$^b$The concentration halfway between those at which 100% and 0% cytotoxicity are seen.
$^c$Therapeutic Index ($CD_{50} \div ED_{50}$).

Cells and Growth Medium

MRC-5 cells are a continuous line of diploid, human, male, embryonic lung cells. Growth medium for the MRC-5 cells consisted of Basal Medium Eagle (BME) (GIBCO BRL), 10% fetal bovine serum (FBS, Hyclone Laboratories, Logan, Utah), 0.035% NaHCO3 (no antibiotics). Hs68 cells were obtained from the ATCC (Rockville, Md.) and were grown in DMEM (GIBCO BRL), with 4.5 mg/ml glucose, 10% FBS, and 0.1% NaHCO3.

Plaque-Reduction Experiments

Cyclocreatine was prepared at a concentration of 4 mg/ml and DHPG was prepared at a concentration of 1 mg/ml in Dulbecco's MEM (DMEM) (GIBCO BRL), 2% FBS, 0.1% NaHCO3, 50 μg/ml gentamicin and diluted in the same medium. Growth medium was decanted from established monolayers of MRC-5 cells in 24-well tissue culture plates (Corning). One ml of virus containing an average of 26.4 plaque forming units, was diluted in the same medium used for the compounds and was placed in each well, except for those to be used as uninfected cell controls (2 wells/plate) in which 1.0 ml of sterile virus-diluent was placed. The plates were centrifuged at 2200 rpm for 30 minutes at room temperature to allow the virus to adsorb.

The medium was removed by aspiration from each well and 0.8 ml of the proper drug dilution was placed in test wells (2 wells/dilution). Tissue culture medium without compound was added (0.8 ml/well) to 4 uninfected cell control wells (2 per plate) and to 8 infected, no drug control ("virus control") wells. The plates were incubated at 37° C. in a moist atmosphere of 5% $CO_2$, 95% air until virus plaques could be distinguished in the virus control wells.

The medium was removed by aspiration from all wells and the cells were stained by adding 0.3 ml of 0.2% crystal violet in 10% buffered formalin to each well. After 15 minutes the stain was aspirated, the plates were rinsed in running tap water until the water was clear, and the plates were inverted and dried at room temperature. Plaques were counted by use of a dissecting microscope.

The ED50 is that concentration of antiviral substance which is calculated to reduce the mean number of virus plaques to half that of the virus controls. CD50 is that concentration of antiviral substance calculated to be half-way between the concentration which produces no visible effect on the cells and the concentration which produces complete cytotoxicity. Cytotoxicity was determined by examination of cells (located away from plaques) in infected wells which had been treated with drug. The therapeutic index (TI) for each substance tested was calculated by the formula: $TI = CD50 \div ED50$.

Antiviral Activity of Cyclocreatine Against HCMV

Table 4 shows that cyclocreatine inhibits plaque formation by Human cytomegalovirus, strain AD-169, in contact-arrested MRC-5 cells. In Table 4, the number of plaques for a given concentration of compound is an average of the number of plaques in the two wells receiving that concentration of drug.

TABLE 4

Antiviral Activity (Plaque Reduction) of Cyclocreatine (AM 285) and DHPG vs HCMV, strain AD-169 in MRC-5 Cells

| Conc. | AM 285 | | DHPG | |
|---|---|---|---|---|
| (μg/ml) | # Plaques | % Reduction | # Plaques | % Reduction |
| 4000 | 0 | 100 | — | — |
| 2000 | 0 | 100 | — | — |
| 1000 | 6 | 75 | — | — |
| 500 | 12 | 54 | — | — |
| 250 | 23 | 0 | — | — |
| 125 | 26 | 0 | — | — |
| 62.5 | 25 | 0 | — | — |
| 100 | — | — | 0 | 100 |
| 32 | — | — | 0 | 100 |
| 10 | — | — | 0.5 | 98 |
| 3.2 | — | — | 15 | 43 |
| # Plaques from eight virus control wells: 26.4 ± 5.2 | | | | |
| $ED50^a$(μg/ml): | 610 | | 3.7 | |
| $CD50^b$(μg/ml): | >4000 | | >100 | |
| $TI50^c$: | >6.5 | | >27 | |

$^a$The concentration at which the average number of plaques is reduced to 50% of that seen in the virus controls (Effective Dose, 50% endpoint).
$^b$The concentration halfway between those at which 100% and 0% cytotoxicity are seen.
$^c$Therapeutic Index ($CD_{50} \div ED_{50}$).

The average number of plaques in treated wells was compared to that of the virus control wells (infected, no drug control) to determine the percent reduction of plaques. The mean plaque counts of the virus control wells was 26.4±5.2. If the mean plaque number in treated wells fell within the range of variation of the control, it was considered zero percent inhibition (i.e., wells with plaque counts greater than 21 were deemed to show 0% inhibition).

The results reported in Table 5 confirm the inhibitory effect of cyclocreatine on plaque formation by Human cytomegalovirus, strain AD-169, in contact-arrested Hs68 cells. The same plaque reduction assay was used in this experiment. The mean plaque counts of virus control wells was 74.2±8.6 plaques. A concentration of drug which yielded a plaque count lower than 65 plaques was considered to be inhibitory.

Cyclocreatine had a definite antiviral effect against HCMV and showed no visible signs of cytotoxicity, even after 8 days of exposure to the cells. The therapeutic index was calculated to be greater than 6.5 in MRC-5 cells and greater than 6.2 in Hs68 cells. The combination of low toxicity and good antiviral activity makes cyclocreatine a potential anti-HCMV material.

TABLE 5

Antiviral Activity (Plaque Reduction) of Cyclocreatine (AM-285) or DHPG vs HCMV, strain AD-169 in Hs-68 Cells

| | AM-285 | | | DHPG | |
|---|---|---|---|---|---|
| Conc. (μg/ml) | # Plaques | % Reduction | Conc. (μg/ml) | # Plaques | % Reduction |
| 4000 | 0 | 100 | 3.2 | 7 | 90 |
| 2000 | 1.5 | 98 | 1.0 | 68.5 | 0 |
| 1000 | 19.5 | 74 | .32 | 100.5 | 0 |
| 500 | 41 | 45 | | | |
| 260 | 87 | 0 | | | |
| 125 | 65 | 0 | | | |
| 62.5 | 71 | 0 | | | |

Plaques from eight virus control wells: 74.2 ± 8.6
ED50$^a$ (μg/ml): 647  1.9
CD50$^b$ (μg/ml): >4000  >1000 (previous data)
TI50$^c$: >6.2  >526

$^a$The concentration at which the average number of plaques is reduced to 50% of that seen in the virus controls (Effective Dose, 50% endpoint).
$^b$The concentration halfway between those at which 100% and 0% cytotoxicity are seen.
$^c$Therapeutic Index (CD$_{50}$ ÷ ED$_{50}$).

Antiviral Activity of Cyclocreatine Against DHPG-resistant Cytomegalovirus Strains The plaque reduction assay was performed as described above using DHPG-resistant (ganciclovir resistant) strains of HCMV. HCMV, strain C8704 or strain C8805-37 were used to infect MRC-5 cells. The results of the assay are recorded in Tables 6 and 7, respectively. The C8704 strain of HCMV is about 10–20× more resistant to DHPG in vitro than strain AD-169. As shown in Table 6, 100% plaque reduction was still observed when cyclocreatine (AM285) was used at a concentration of 10 mg/ml, indicating that the C8704 strain is less than 2× more resistant to cyclocreatine (AM285) than is strain AD-169.

Cyclocreatine may therefore provide an alternative therapy for drug resistant strains. Furthermore, the results suggest that cyclocreatine operates by an antiviral mechanism distinct from that of DHPG (ganciclovir). However, the amount of resistance shown by strain C8805-37 to DHPG and cyclocreatine was quite similar, when compared to the activities of each compound against strain AD-169 (Table 7). This result was confirmed in a second experiment in which the plaque number in the virus control wells was 44.0±5.3. Note that resistance to DHPG in strain C8805-37 is only 3-4 fold greater than strain AD-169. In addition, the molecular basis for viral resistance to DHPG has not been established and could be different in each strain.

TABLE 6

Antiviral Activity (Plaque Reduction) of Cyclocreatine (AM 285) or DHPG vs HCMV, strain C8704 (DHPG resistant) in MRC-5 Cells

| | AM 285 | | | DHPG | |
|---|---|---|---|---|---|
| Conc. (μg/ml) | # Plaques | % Reduction | Conc. (μg/ml) | # Plaques | % Reduction |
| 10000 | 0 | 100 | 32 | 91 | 41 |
| 5000 | 3.5 | 96 | 10 | 80 | 0 |
| 2500 | 14.5 | 84 | 3.2 | 85 | 0 |
| 1250 | 48.5 | 47 | 1.0 | 92.5 | 0 |
| 625 | 52.5 | 42 | | | |
| 312.5 | 65.5 | 28 | | | |
| 156.25 | 81 | 0 | | | |

Plaques from eight virus control wells: 91.0 ± 8.4
ED50$^a$ (μg/ml): 900  >32 (~41)
CD50$^b$ (μg/ml): >10000  >1000 (previous data)
TI50$^c$: >11.1  >24

$^a$The concentration at which the average number of plaques is reduced to 50% of that seen in the virus controls (Effective Dose, 50% endpoint).
$^b$The concentration halfway between those at which 100% and 0% cytotoxicity are seen.
$^c$Therapeutic Index (CD$_{50}$ ÷ ED$_{50}$).

TABLE 7

Antiviral Activity (Plaque Reduction) of Cyclocreatine (AM-285) or DHPG vs HCMV, strain C8805-37 (DHPG resistant) in MRC-5 Cells

| | AM-285 | | | DHPG | |
|---|---|---|---|---|---|
| Conc. (μg/ml) | # Plaques | % Reduction | Conc. (μg/ml) | # Plaques | % Reduction |
| 10000 | 0 | 100 | 32 | 4.5 | 61 |
| 5000 | 1.5 | 87 | 10 | 10 | 0 |
| 2500 | 6.5 | 43 | 3.2 | 6.5 | 43 |
| 1250 | 9.5 | 0 | 1.0 | 13 | 0 |
| 625 | 10.5 | 0 | | | |
| 312.5 | 12 | 0 | | | |
| 156.25 | 9.5 | 0 | | | |

Plaques from eight virus control wells: 11.5 ± 2.1
ED50$^a$ (μg/ml): 2780  11
CD50$^b$ (μg/ml): >10000  >1000 (previous data)
TI50$^c$: >3.6  >91

$^a$The concentration at which the average number of plaques is reduced to 50% of that seen in the virus controls (Effective Dose, 50% endpoint).
$^b$The concentration halfway between those at which 100% and 0% cytotoxicity are seen.
$^c$Therapeutic Index (CD$_{50}$ ÷ ED$_{50}$).

In Vitro Antiviral Activity of Cyclocreatine Against Murine Cytomegalovirus

Virus Strains

Murine Cytomegalovirus (MCMV), strain Smith, was obtained from the ATCC (Rockville, Md.).

Cells and Growth Medium

C127I cells, a non-transformed clonal cell line derived from a mammary tumor of an RIII mouse, were obtained from the ATCC (Rockville, Md.) and were grown in Eagle's minimum essential medium with non-essential amino acids (MEM) (GIBCO BRL, Research Products Division, Life Technologies, Inc., Grand Island, N.Y.)), with 10% FBS (Hyclone Laboratories, Logan, Utah), and 0.1% NaHCO$_3$ (no antibiotics).

Test medium for dilution of MCMV was Dulbecco's Modified Eagle Medium (DMEM), with 4.5 mg/ml glucose, 2% FBS, 0.1% NaHCO$_3$, and 50 μg/ml gentamicin.

Effect of Cyclocreatine on MCMV

The murine CMV experiments were performed in the same manner as the guinea pig CMV experiments, with the following exceptions: (1) C127I cells and MCMV were used, (2) test medium for dilution of compounds and virus, and (3) as the effect of drug was not strong, plaques were counted instead of waiting for full development of the cytopathic effect. Cyclocreatine had little activity against MCMV under the conditions of this experiment (e.g., 53% plaque reduction in the presence of 10 mg/ml cyclocreatine). It is unclear whether the differential effect of cyclocreatine against the guinea pig, human and murine cytomegaloviruses is due to differences between the viruses or the host cell lines used in the experiments.

Effect of Cyclocreatine on TK− HSV-1

The antiviral activity of cyclocreatine against a thymidine kinase negative strain (TK−) of HSV-1 was assayed in Vero cells using the CPE-reduction assay as described in Example 5; however the cells were not serum starved. The titer of HSV-1 used in this study, expressed as cell culture infectious dose, 50% endpoint ($CCID_{50}$), was $1 \times 10^{2.5}$ $CCID_{50}$/well. The HSV-1 strain BW10168(TK−) used in this experiment shows resistance to acyclovir when compared with other TK+ strains of HSV-1. Typically the ED50 for acyclovir is 8- to 12-fold greater for this TK− strain than for a similar TK+ strain.

Cyclocreatine displayed an ED50 of about 900 μg/ml (~6.3 mM) in the assay (Table 8). Relative activity against a TK+ strain of HSV-1 (FIG. 1) is approximately 7 mM. Since HSV TK activity is not required for antiviral activity of cyclocreatine, cyclocreatine must act through a different mechanism than acyclovir.

Antiviral Activity of Cyclocreatine against VZV

The antiviral activity of cyclocreatine against Varicella-Zoster virus, strain Oka (Diagnostic Hybrids Inc., Athens, Ohio), was determined using the plaque reduction assay in MRC-5 cells (Table 9A) and CV-1 cells (a continuous line of African Green Monkey kidney cells obtained from the ATCC, Rockville, Md.; Table 9B). As shown in Table 9A and 9B, in this assay, cyclocreatine showed antiviral activity similar to or better than that shown against HCMV. Interestingly, DHPG was less effective against VZV than it was against HCMV, strain AD-169.

TABLE 8

Antiviral Activity (CPE Reduction) of Cyclocreatine (AM-285) or Acyclovir vs Herpes Simplex Virus, Type 1, strain BW10168 (TK−), in Vero Cells

| | AM-285 | | | Acyclovir | |
|---|---|---|---|---|---|
| Conc. (μg/ml) | Visible Cyto-toxicity | Average CPE | Conc. (μg/ml) | Visible Cyto-toxicity | Average CPE |
| 4000 | 20 | 0.7 | 1000 | 40 | 0 |
| 2000 | 20 | 2.0 | 316 | 0 | 0.2 |
| 1000 | 0 | 1.8 | 100 | 0 | 0.5 |
| 500 | 0 | 1.7 | 32 | 0 | 0.3 |
| 260 | 0 | 3.2 | 10 | 0 | 1.5 |
| 125 | 0 | 3.5 | 3.2 | 0 | 3.2 |
| 62.5 | 0 | 3.2 | 1.0 | 0 | 4.0 |
| 0 | | Average CPE 4.0 (virus controls) | | | |
| $ED50^a$ (μg/ml): | | 384.4 | | 10.6 | |
| $CD50^b$ (μg/ml): | | >4000 | | >1000 | |

TABLE 8-continued

Antiviral Activity (CPE Reduction) of Cyclocreatine (AM-285) or Acyclovir vs Herpes Simplex Virus, Type 1, strain BW10168 (TK−), in Vero Cells

| | AM-285 | | | Acyclovir | |
|---|---|---|---|---|---|
| Conc. (μg/ml) | Visible Cyto-toxicity | Average CPE | Conc. (μg/ml) | Visible Cyto-toxicity | Average CPE |
| $TI50^c$: | | >4.5 | | >94 | |

[a] The concentration at which the average number of plaques is reduced to 50% of that seen in the virus controls (Effective Dose, 50% endpoint).
[b] The concentration halfway between those at which 100% and 0% cytotoxicity are seen.
[c] Therapeutic Index ($CD_{50} \div ED_{50}$).

TABLE 9A

Antiviral Activity (Plaque Reduction) of Cyclocreatine (AM-285) or DHPG vs *Varicella-Zoster* Virus, strain Oka, in MRC-5 Cells

| | AM-285 | | | DHPG | |
|---|---|---|---|---|---|
| Conc. (μg/ml) | # Plaques | % Reduction | Conc. (μg/ml) | # Plaques | % Reduction |
| 4000 | 0 | 100 | 10 | 12.5 | 62 |
| 2000 | 3 | 91 | 3.2 | 25 | 0 |
| 1000 | 9.5 | 71 | 1.0 | 37 | 0 |
| 500 | 19 | 42 | 0.32 | 24.5 | 0 |
| 260 | 21 | 36 | | | |
| 125 | 26 | 0 | | | |
| 62.5 | 26 | 0 | | | |

Plaques from seven virus control wells: 32.7 ± 9.3
$ED50^a$ (μg/ml): 564    8.0
$CD50^b$ (μg/ml): >4000    >1000 (previous data)
$TI50^c$: >7.1    >125

[a] The concentration at which the average number of plaques is reduced to 50% of that seen in the virus controls (Effective Dose, 50% endpoint).
[b] The concentration halfway between those at which 100% and 0% cytotoxicity are seen.
[c] Therapeutic Index ($CD_{50} \div ED_{50}$).

EXAMPLE 6

Antiviral Activity May Require Phosphorylation by CK

Figure 16A:
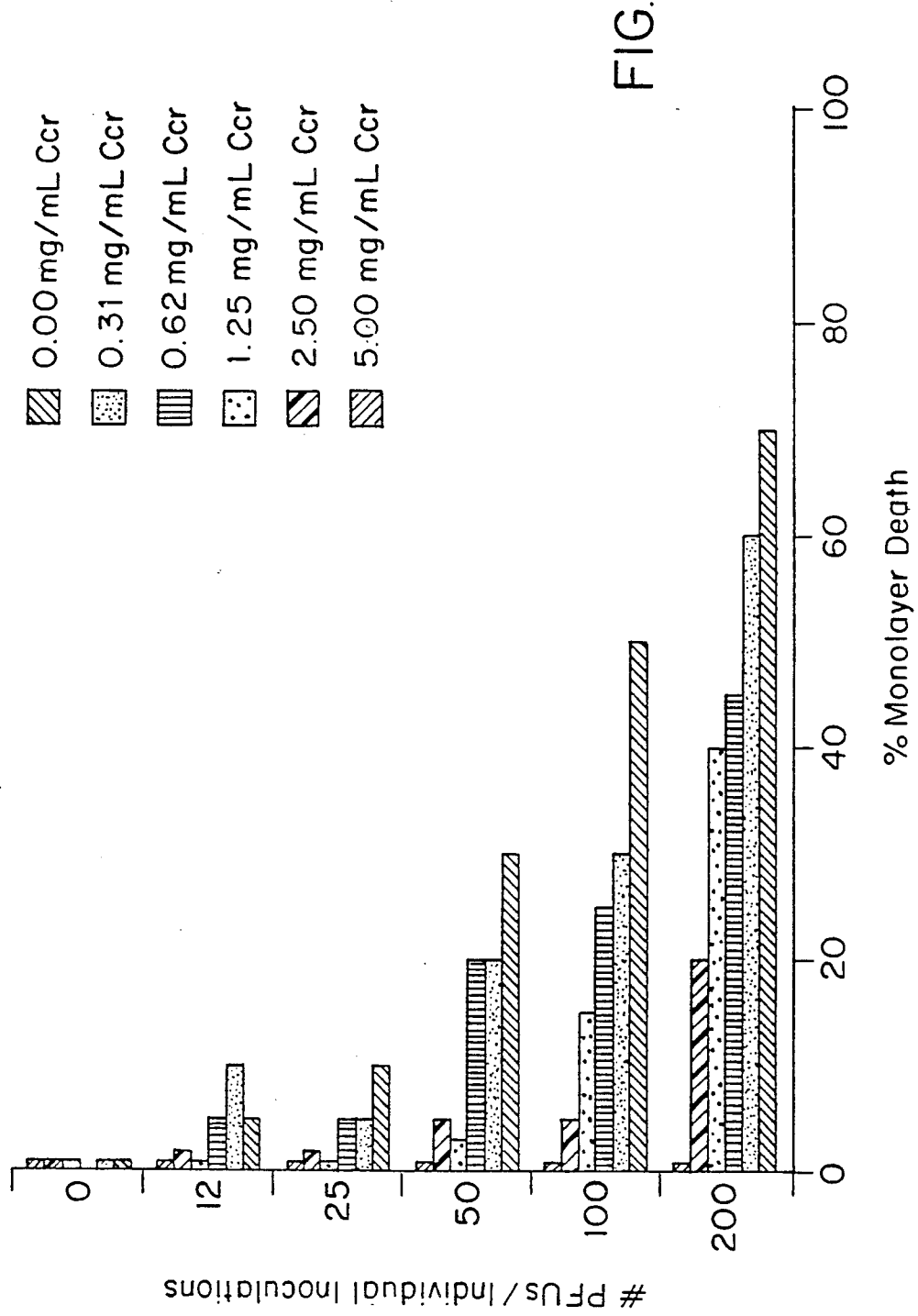
FIG. 16A is a bar graph depicting the effect of 6 different concentrations of cyclocreatine (bars from top to bottom for each inoculum: 5.0 mg/ml, 2.5 mg/ml, 1.25 mg/ml, 0.62 mg/ml, 0.31 mg/ml, 0 mg/ml) on the percent of monolayer cell death of Vero cells inoculated with various amounts (PFU)) of HSV-1 virus.
Figure 16B:
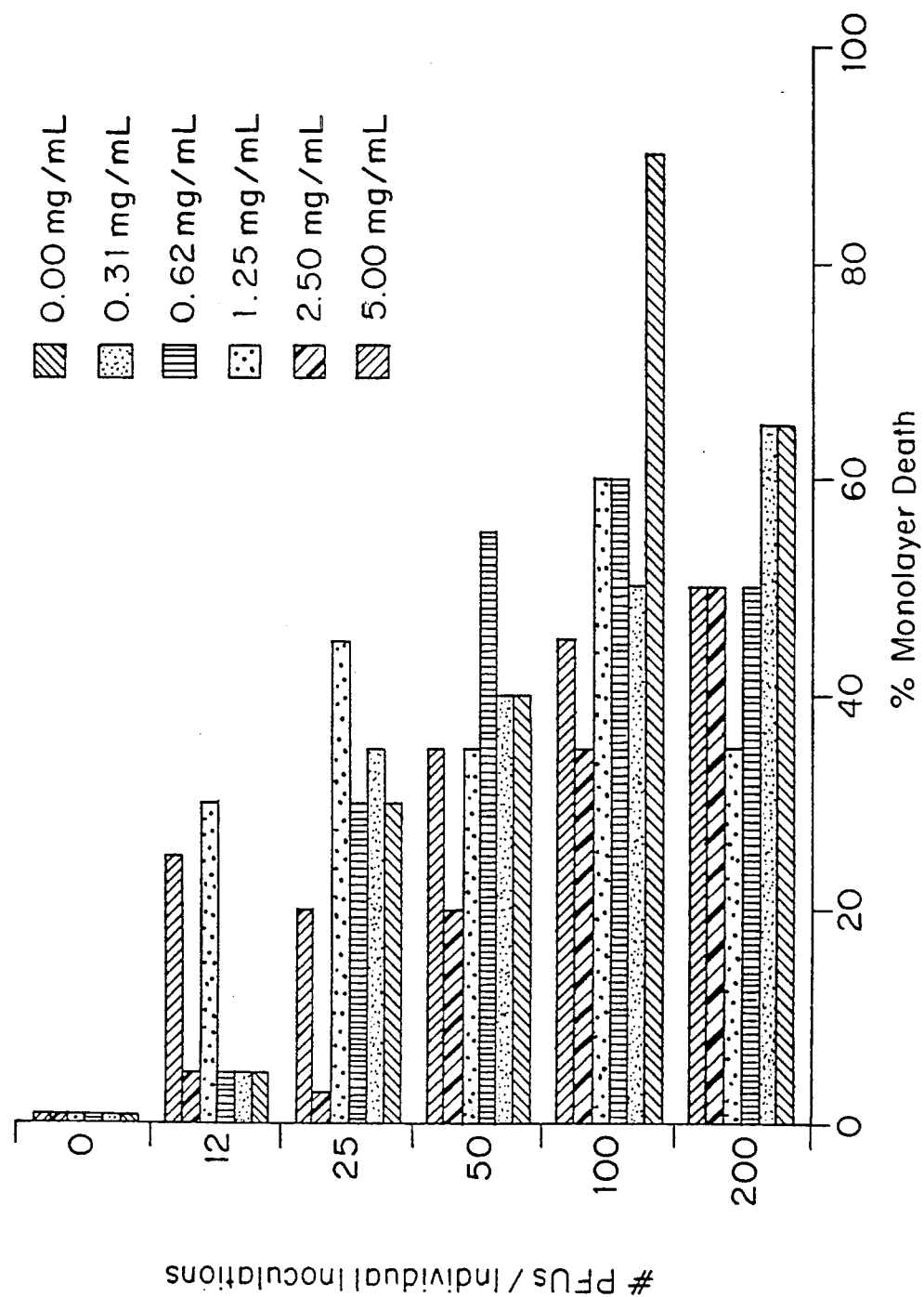
FIG. 16B shows the effects of 1-carboxymethyl-2-aminoimidazole at the same concentrations (bars from top to bottom for each inoculum: 5.0 mg/ml, 2.5 mg/ml, 1.25 mg/ml, 0.62 mg/ml, 0.31 mg/ml, 0 mg/ml) on the percent of monolayer cell death of Vero cells inoculated with various amounts of HSV-1 virus. The length of each bar represents the percent monolayer death in a single well.

To study the mechanism of the anti-viral effect of cyclocreatine, a compound that is structurally closely related to cyclocreatine was tested for antiviral activity against HSV-1 and HSV-2 in the cytopathic effect assay essentially as described Example 1. As shown in FIG. 16, while cyclocreatine shows a dose response against HSV-1 induced cytopathogenicity in Vero cells (FIG. 16A), 1-carboxymethyl-2-aminoimidazole (FIG. 16B) shows no such effect under the conditions used.

Cyclocreatine is phosphorylated in tissues such as brain, muscle, and heart, which are high in creatine kinase (Roberts, J. J. and J. B. Walker, *Arch. Biochem. Biophys.* 220: 563–571 (1983)). In contrast, 1-carboxymethyl-2-aminoimidazole, which binds to creatine kinase with an affinity equal to that of cyclocreatine, is phosphorylated 5 orders of magnitude slower than cyclocreatine (Lowe, G. and B. S. Sproat, *J. Biol. Chem.* 255: 3944–3951 (1980)). Possibly, 1-carboxymethyl-2-aminoimidazole shows no antiviral activity because it is phosphorylated so slowly by creatine kinase.

TABLE 9B

Antiviral Activity (Plaque Reduction) of Cyclocreatine (AM-285) or DHPG vs Varicella-Zoster Virus, strain Oka, in CV-1 Cells

| | AM-285 | | | DHPG | |
|---|---|---|---|---|---|
| Conc. (μg/ml) | # Plaques | % Reduction | Conc. (μg/ml) | # Plaques | % Reduction |
| 10000 | 0 | 100 | 10 | 63 | 10 |

TABLE 9B-continued

Antiviral Activity (Plaque Reduction) of Cyclocreatine (AM-285) or DHPG vs Varicella-Zoster Virus, strain Oka, in CV-1 Cells

| AM-285 | | | DHPG | | |
|---|---|---|---|---|---|
| Conc. (μg/ml) | # Plaques | % Reduction | Conc. (μg/ml) | # Plaques | % Reduction |
| 5000 | 0 | 100 | 3.2 | 77 | 0 |
| 2500 | 0 | 100 | | | |
| 1250 | 1 | 98 | | | |
| 625 | 3 | 96 | | | |
| 312.5 | 12 | 83 | | | |
| 156 | 28.5 | 59 | | | |

Plaques from virus control wells: 70.25 ± 6.9
ED50[a] (μg/ml): <156 (~107) >10
CD50[b] (μg/ml): 5790 >10
TI50[c]: ~54

[a]The concentration at which the average number of plaques is reduced to 50% of that seen in the virus controls (Effective Dose, 50% endpoint).
[b]The concentration halfway between those at which 100% and 0% cytotoxicity are seen.
[c]Therapeutic Index (CD50 ÷ ED50).

Consistent with a possible requirement of efficient phosphorylation for antiviral activity, cyclocreatine is phosphorylated in tissue culture under the same conditions used in the antiviral assay. As shown below in Table 10, the more creatine kinase the cells contain, the higher the percentage of phosphorylation of cyclocreatine. This trend is still observed for cells with lower CK activity, even after 8 days of incubation with drug.

EXAMPLE 7

Antiviral Effect of Compound 5/6

Preparation of Compounds 5 and 6 as AM 361

Compounds specified by structures 5 and 6 (FIG. 19) differ from cyclocreatine by the addition of a substituent (R) to the 5-membered ring. This substitution is designed to enhance the energetics of substrate binding, while allowing phosphoryl group transfer to occur. A mixture of compounds specified by structures 5 and 6, where R=CH$_3$, was prepared, and the preparation is referred to as AM 361.

The synthesis of these methyl-substituted derivatives of cyclcocreatine relied upon the incorporation of differentially protected chiral 1,2-diamines by methods such as those described in FIG. 22. In particular, compounds 5 and 6 were prepared in analogy to the synthesis of cyclocreatine according to Griffith and Walker (*J. Biol. Chem.* 251(7): 2049-2054 (1976)). In summary, the sodium salt of chloroacetic acid was condensed with (±)-1,2-diaminopropane in water to generate the two regioisomeric carboxymethyl diamines in reaction 1 as shown below.

TABLE 10

| Cell line | CK activity (units/mg) | % Cyclocreatine Phosphorylated |
|---|---|---|
| ME180 | 0.9 | 85 |
| DU 145 | 0.4 | 76 |
| Vero | 0.05 | 68 |
| A2058 | 0.01 | 13 |

(The percent cyclocreatine phosphorylated was determined by the method of Roberts and Walker (Roberts, J. J. and J. B. Walker, Arch. Biochem. Biophys. 220: 563-571 (1983)). Total creatine kinase activity was determined in crude protein extracts from each cell line by means of a kit (Sigma Kit #49 UV) obtained from Sigma Chemical Corp. (St. Louis, MO) following the instructions of the manufacturer. All cell lines were obtained from the ATCC.)

The mixture of carboxymethyl diamines was then condensed with cyanogen bromide to generate the mixture of compounds 5 and 6 (R=methyl), as indicated in reaction 2 below. Crystallization from water followed by recrystallization from hot ethanol-water (80:20, v/v) gave the product mixture of 5 and 6 enriched to about 95% in one unidentified isomer. This product mixture constitutes AM 361. The detailed experimental procedure is given below.

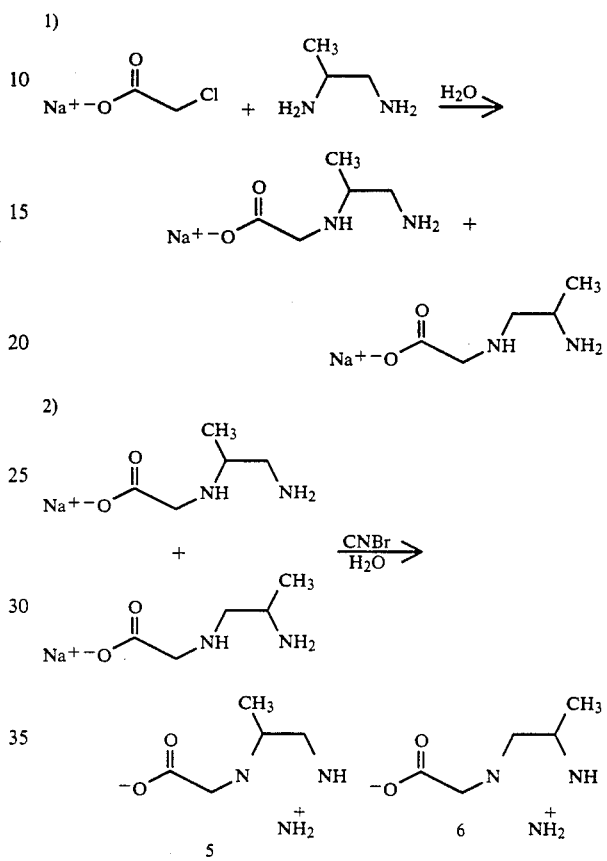

Synthetic Methods

To a solution of chloroacetic acid (142 g) in H$_2$O (140 mL) initially at 0° C. was added a solution of NaOH (62 g) in H$_2$O (120 mL). The resulting solution was added to a 70-80° C. solution of (±)-1,2-diaminopropane (125 mL) and H$_2$O (75 mL) over 90 min. The resulting mixture was maintained at 60-70 ° C. for an additional 2 hours, then cooled to 10-15 ° C. A solution of cyanogen bromide (150 g) in methanol (200 mL) was added while maintaining the reaction mixture temperature between 15-32° C. The resulting mixture was stirred overnight and the precipitated NaBr was removed by filtration. Acetone and diethyl ether were added and the additional NaBr precipate was removed by filtration. The solvent was removed in vacuo, and the residue was crystallized from hot H$_2$O. The first crystalline product (shown by $^1$H NMR to be a mixture, enriched in one isomer) was isolated and recrystallized from hot ethanol-H$_2$O (80:20, v/v). $^{13}$C and $^1$H NMR analysis indicated that this second recrystallized product contains methyl regioisomers 5 and 6 enriched to ~95% of one unidentified regioisomer. The second recrystallized product is referred to herein as "compound 5/6". It was not determined which compound was the major and which was the minor component.

Phosphorylation of Compound 5/6

Compound 5/6 (AM 361), where R=CH$_3$, was prepared as described above and assayed for phosphorylation by creatine kinase in a coupled assay with pyruvate kinase and lactate dehydrogenase (LDH) as described (Bergmeyer, H. U., ed. (1974), In: *Methods of Enzymatic Analysis*, Second English Edition, Volume 4, (Verlag Chemie Weinheim and Academic Press, Inc.: New York, London) pp. 1772–1779).

Each compound listed in Table 11 below was tested at a concentration of 40 mM. Compound 5/6 (AM 361) was slowly phosphorylated.

TABLE 11

| Compound | Δ in Absorbance/min | % Rate of Creatine |
| --- | --- | --- |
| Creatine | 1.18 | 100 |
| Cyclocreatine | 0.54 | 46 |
| Compound 5/6 | 0.041 | 2.4 |

Antiviral Activity of Compound 5/6 (AM 361)

Creatine analog 5/6 (AM 361) was assayed for antiviral activity in the cytopathic effect assay essentially as described in Example 1. To determine the antiviral effect of AM 361 against HSV-1, Vero cells were challenged with varying concentrations of virus as described above. The plates were incubated in the presence of several different concentrations of AM 361 until cytopathogenicity was observed in the control wells containing virus only. A no drug control plate was prepared and treated identically to the first plate, except that low serum medium rather than drug was added to the infected monolayers.

In one experiment, AM 361 was tested at concentrations of 0.0 mM, 2.73 mM, 5.47 mM, 11.0 mM, 22.1 mM and 44.2 mM. At a concentration of 44.2mM, AM 361 reduced virus-induced monolayer death from 90% (200 PFU/well), 40% (100 PFU/well), 45% (50 PFU/well), 30% (25 PFU/well), and 50% (12 PFU/well) observed in the relevant no drug control to a value of 2% for each inoculum. At a concentration of 22.1 mM, under the conditions of the experiment, AM 361 reduced the cytopathic effect as compared with the no drug control in wells inoculated with 25 or 50 PFU/well, but not in wells inoculated with 200 PFU/well, 100 PFU/well or 12 PFU/well.

Figure 17A:
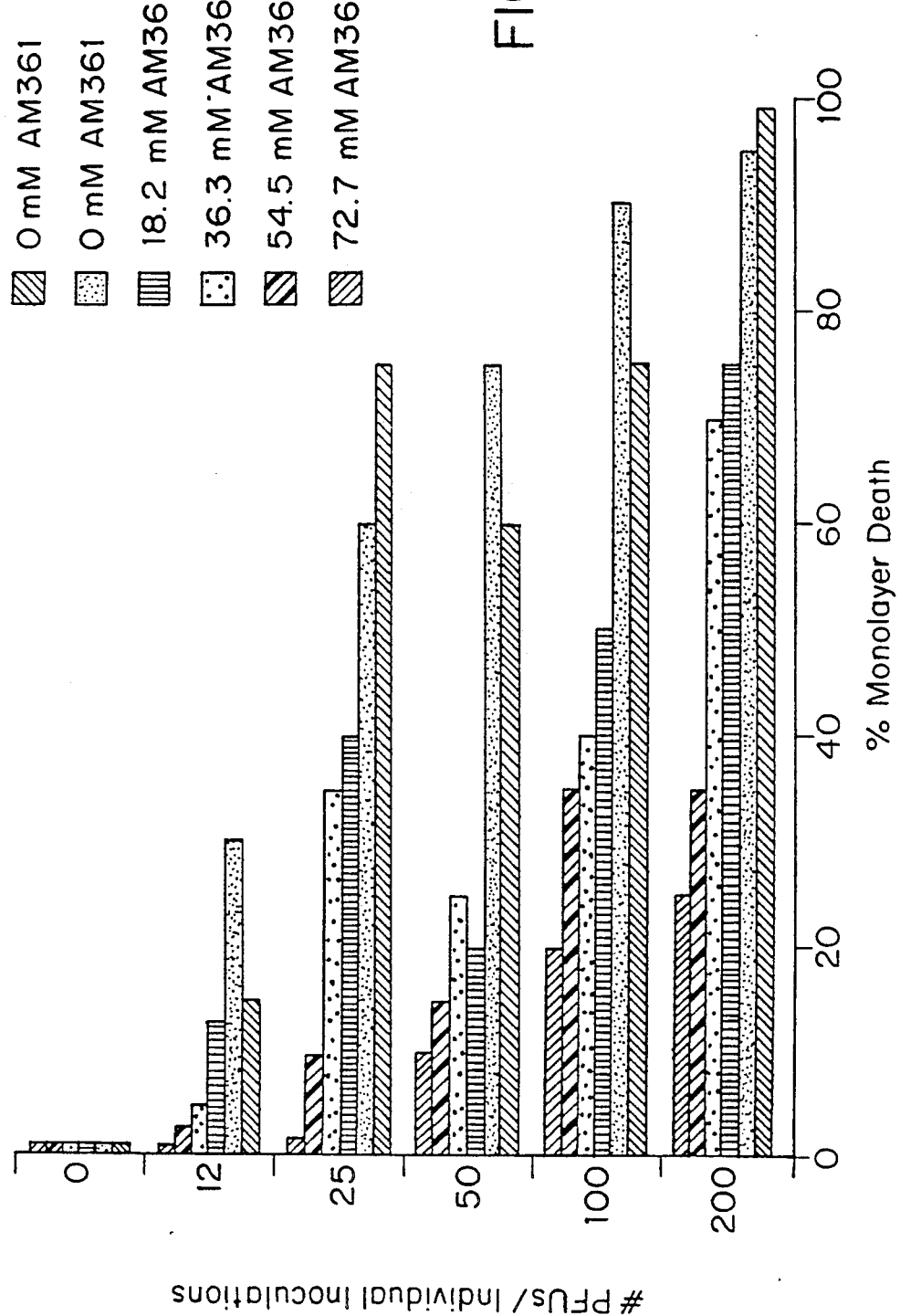
FIG. 17A is a bar graph depicting the effect of 5 different concentrations of cyclocreatine (bars from top to bottom for each inoculum: 72.7 mM, 54.5 mM, 36.3 mM, 18.2 mM, 0.0 mM, and 0.0 mM) on the percent of monolayer cell death of Vero cells inoculated with various amounts (PFUs) of HSV-1 virus. The bar graph illustrates the protective effect of compound 5/6 (AM361) in Vero cells against the cytopathic effect of HSV-1 infection.
Figure 17B:
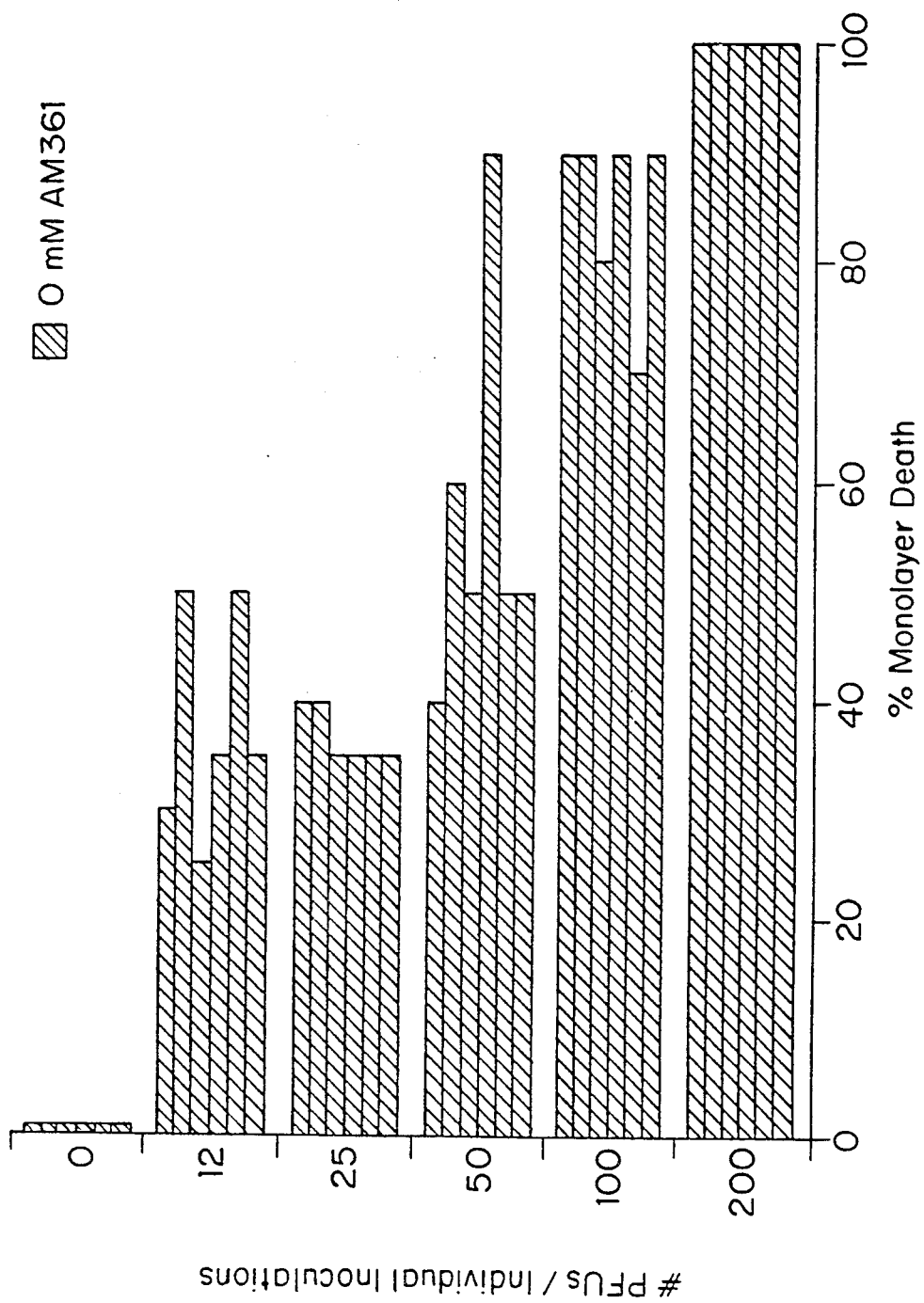
FIG. 17B is a bar graph depicting the effect of various amounts of HSV-1 virus on the percent monolayer death in the absence of drug (six wells/inoculum). The length of each bar represents the percent monolayer death in a single well.

In a separate experiment, and at higher concentrations of AM 361, a dose related response was evident. FIG. 17 shows the results of such a cytopathogenicity study of HSV-1 in Vero cells. The percentage of monolayer death observed (x-axis) in each well at different concentrations of AM 361 (denoted by different shaded bars) is plotted for a range of vital inoculla (y-axis; plaque-forming units (PFUs) per inoculum). FIG. 17A shows that in serum-starved Veto cells, at varying concentrations of virus inoculla, AM 361 inhibited the cytopathic effect of HSV-1.

In FIG. 17A, the percent monolayer death in the absence of viral infection (0 PFUs) provided a control for drug cytotoxicity from the same plate as the infected cells. In addition, the results from the no drug control plate (FIG. 17B) show that in the absence of cyclocreatine, most wells of Veto cells that receive a given inoculum of HSV-1 virus display comparable levels of cell death. Therefore, this creatine analog has a discernible antiviral effect.

EXAMPLE 8

Antiviral Effect of Compound 7

Synthesis of Compound 7

Compound 7 was prepared by a one-step condensation of glycylglycine with cyanamide as follows:

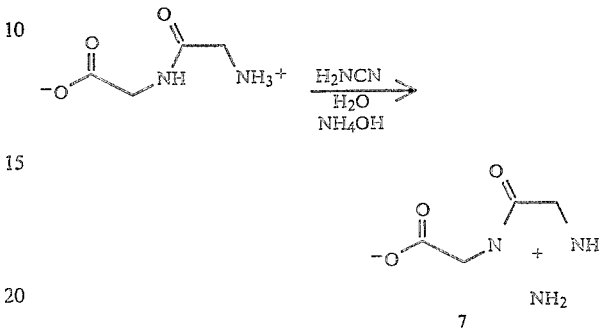

Glycylglycine (2.64 g) and 22% aqueous NH$_4$OH (several drops per addition) were alternatively added portion-wise to a solution of cyanamide (2.1 g) in H$_2$O (20 ml) with intermittent shaking to effect complete dissolution. The resulting solution was sealed and allowed to stand for 4 days. The resulting crystalline solid was collected by filtration, washed with H$_2$O, and dried to afford ca. 0.7 g of compound 7. The $^1$H NMR spectrum of the product was consistent with the desired structure.

Activity in Cytopathic Effect Assay

Compound 7 (FIG. 19) was tested in parallel to AM 361 (Example 7) in the cytopathic effect assay against HSV-1 at concentrations of 0 mM, 2.58 mM, 5.16 mM, 10.4 mM, 20.8 mM, and 41.7 mM in Vero cells. At 41.7 mM, compound 7 showed consistent antiviral activity, reducing monolayer death at each inoculum tested (12, 25, 50, 100 or 200 PFU/well) as compared with the no drug control. None of the other concentrations tested showed a consistent antiviral effect in the assay under the conditions used. Some monolayer death (4%) was observed in cells exposed to 41.7 mM compound 7 in the absence of virus, suggesting slight cytotoxicity at this concentration. Further experiments are required to establish the significance of the antiviral effect.

EXAMPLE 9

Antiviral Effects of Compounds 10a and 10b

Synthetic Scheme for Preparation of compounds 10A (R=methyl) and 10B (R=allyl)

Analogs 10a and 10b were prepared by condensation of ethylenediamine monoacetic acid with N-methyl or N-allyl thiouronium salts by analogy to the procedure described in *J. Med. Chem.* 23, 1232–1235 (1980). The ethylenediamine monoacetic acid was prepared as described by Nguyen (Nguyen, A. C. K., Ph.D. Thesis in Pharmaceutical Chemistry, UCSF, 1983, p. 40) and the thiouronium salts were prepared from the commercially available N-methyl and N-allyl thioureas according to the procedures described in Rowley et al. *J. Am. Chem. Soc.* 93, 5542–5551 (1971); and Curd et al. *J. Chem. Soc.* p. 1742 (1949).

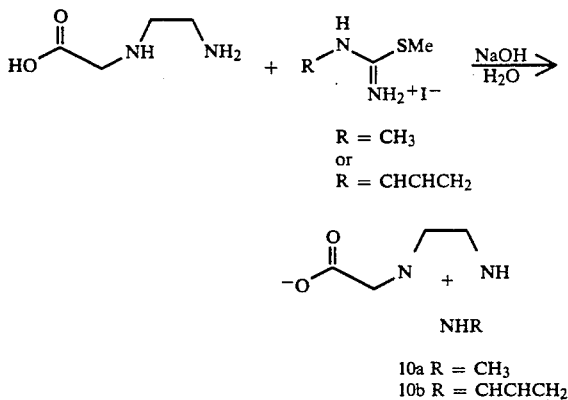

10a R = CH₃
10b R = CHCHCH₂

Preparation of S-methyl-N-methylthiouronium Hydroiodide

To a solution of N-methylthiourea (8.25 g, 91 mmole) in methanol (50 mL) was added methyl iodide (14.33 g, 7.2 mL, 101 mmole). The resulting solution was heated at reflux for 15 hours before the solvent was removed by rotary evaporation. The remaining solid was suspended in ethyl acetate and the white crystalline product was collected by filtration and dried under vacuum to give 19.1 g of desired product as characterized by $^1$H NMR.

Preparation of S-methyl-N-allythiouronium Hydroiodide.

To a solution of N-allythiourea (10.57 g, 91 mmole) in methanol (50 mL) was added methyl iodide (14.33 g, 7.2 mL, 101 mmole). The resulting solution was heated at reflux for 22 hours before the solvent was removed by rotary evaporation. To the remaining oil was added acetone (1 mL), ethyl acetate (1 mL), and diethyl ether (200 mL) causing a white precipitate to form. The solids were collected by filtration and washed with ethyl acetate followed by diethyl ether, and dried in vacuo to give 23.8 g of desired product as characterized by $^1$H NMR.

Preparation of Compounds 10a and 10b

A solution of the N-methyl or N-allyl thiouronium salt (11 mmole) in H₂O (2.5 mL) was added over 2 hours to a stirred, room temperature solution of ethylenediamine monoacetic acid (1.3 g, 11 mmole) and NaOH (11 mmole) in H₂O (2.75 mL). The resulting clear solution was stirred for 12 hours at room temperature before the solvent was removed by rotary evaporation. Methanol (2×15 mL) was added to and evaporated from the residue twice. Methanol (2-3 mL) and diethyl ether (200 mL) were added to the residue causing a gummy solid to form. The supernatant was decanted and the residue was dried under vacuum, affording 10a and 10b as hygroscopic solids.

Activity in Cytopathic Effect Assay

Compound 10a, where R=methyl, was tested for antiviral activity against HSV-1 in the cytopathic effect assay as described in Example 1, using concentrations of 0 mM, 2.36 mM, 4.73 mM, 9.54 mM, 19.1 mM, and 38.2 mM. As compared with the corresponding no drug control, a reduction in monolayer death on exposure to compound 10a at a concentration of 19.1 mM was observed in wells inoculated with 12, 50, 100 or 200 PFU/well, but not in wells inoculated with 25 PFU/well. However, similar reductions in monolayer death were observed only inconsistently at other concentrations in this experiment. Some monolayer death (5%) was observed in the absence of virus in wells treated with 38.2 mM compound 10a. In the presence of virus, treatment with 38.2 mM compound 10a consistently led to a greater % monolayer death than the lower dose of 19.1 mM. The possibility that the apparent antiviral effect at 19.1 mM is due to cytotoxicity which only becomes apparent at a 2-fold higher concentration of drug has not been excluded.

Compound 10b, where R=allyl, was similarly assayed for antiviral activity against HSV-1 in Vero cells. No consistent antiviral effect was observed under the conditions of the experiment, at 12, 25, 50, 100 or 200 PFU/well at each of the following concentrations: 2.58 mM, 5.69 mM, 11.48 mM, 22.95 or 45.90 mM compound 10b. In the no virus controls, cytotoxicity became apparent at 23 mM (7% monolayer death), and was more marked at 45.9 mM (30% monolayer death).

EXAMPLE 10

Antiviral Effect of Other Compounds

A number of additional compounds structurally related to cyclocreatine and each capable of inhibiting creatine kinase activity were tested for antiviral activity against HSV-1 in Vero cells in culture. The compounds tested were homocyclocreatine (1-carboxyethyl-2-iminoimidazolidine), carbocreatine, ethylguanidino acetic acid (EGA), β-guanidinopropionate and 1-carboxymethyl-2-iminohexahydropyrimidine. In addition, cyclocreatine and acyclovir were tested in parallel as positive controls, while creatine provided a base for comparison.

The synthesis of homocyclocreatine (1-carboxyethyl-2-iminoimidazolidine) was carried out as described by Roberts and Walker (Roberts, J. J. and J. B. Walker, *Arch. Biochem. Biophys.* 220: 563–571 (1983)). The synthesis of carbocreatine was carried out as described (Nguyen, Ann Cae Khue, Ph.D. Thesis in Pharmaceutical Chemistry, (University of California, San Francisco, 1983). The synthesis of ethylguanidino acetic acid (EGA) was performed by Dalton Chemical Co., as described (Richmond, J. J. and Walker, *J. Arch. Biochem. Biophys.* 252: 564–570 (1982)). β-guanidinopropionate (#G6878) was purchased from Sigma Chemical Co. (St. Louis, Mo.). 1-carboxymethyl-2-iminohexahydropyrimidine was synthesized according to Griffiths and Walker (Griffiths, G. G. and J. B. Walker, *J. Biol. Chem.* 251: 2049–2054 (1976)). Creatine was purchased from Sigma Chemical Co. (St. Louis, Mo.).

In one experiment, the percent monolayer death at a single inoculum of virus (125 PFUs) was determined for a range of drug concentrations essentially as described in Example 1; however, no agar overlay was used. Each concentration was tested six times (6 wells at each concentration). Due to cytotoxicity observed with a variety of cell lines, the carbocreatine concentration was varied over a range from 0 mM to 3.5 mM in this experiment.

Under the conditions used in the assay each of the compounds tested showed a weak protective effect in some wells at the highest concentrations of drug tested (70 mM homocyclocreatine, 3.5 mM carbocreatine, 84 mM (EGA), 38 mM or 75.8 mM β-guanidinopropionate and 91 mM 1-carboxymethyl-2-iminohexahydropyrimidine). Pre-feeding cells with homocyclocreatine prior to inoculation did not yield a reproducible antiviral effect.

In this assay, creatine showed some activity at a concentration 70 mM, possibly due to a change in the osmolarity of the medium. Further, the concentrations of cyclocreatine and acyclovir required for inhibition in this assay were higher than usual (35 mM for ~20% inhibition and 2.5 mM for ~50% inhibition, respectively). In sum, homocyclocreatine, carbocreatine, EGA, $\beta$-guanidinopropionate and 1-carboxymethyl-2-iminohexahydropyrimidine did not display a strong and/or reproducible antiviral activity in this particular experiment.

In a second set of experiments, a variety of concentrations of each drug were used at a series of different inoculla (0, 12, 25, 50, 100 and 200 PFU). In this experiment, cyclocreatine showed consistent dose-dependent inhibition of the percent monolayer cell death in HSV-1 infected Veto cells. Cyclocreatine concentrations tested in this set of experiments included 0 mM, 2.15 mM, 4.3 mM, 8.68 mm, 17.35 mM and 34.7 mM cyclocreatine. Carbocreatine (0 mM, 0.11 mM, 0.21 mM, 0.43 mM 0.85 mM and 1.71 mM), p-guanidinopropionate (0 mM, 2.35 mM, 4.7 mM, 9.48 mM, 18.95, 37.9 mM), EGA (0 mM, 2.6 mM, 5.21 mM 10.50 mM, 21.0 mM and 42.0 mM), and 1-carboxymethyl-2-iminohexahydropyrimidine (0 mM, 2.83 mM, 5.67 mM, 11.42 mM, 22.8 mM and 45.7 mM) showed no dose-response or consistent protective effect in this experiment. Homocyclocreatine (2.15 mM, 4.3 mM, 8.68 mM, 17.35 mM and 34.7 mM) displayed some weak activity, particularly at higher titers of virus.

Effect of Homocyclocreatine on Other Viruses

Homocyclocreatine was tested in parallel with cyclocreatine against (1) HCMV, strain AD-169 in MRC-5 cells or Hs68 cells (2) HCMV, DHPG-resistant strain C8704 in MRC-5 cells, (3) HCMV, DHPG-resistant strain C8805-37 in MRC-5 cells, and (4) Varicella-Zoster Virus, strain Oka in MRC-5 cells, using the plaque reduction assay as described in Example 5. Weak antiviral activity was observed against HCMV, strain AD-169 at 2 or 4 mg/ml, and against HCMV strains C8704 and C8805-37 at 15.8 mg/ml. Weak activity against VZV was also observed at concentrations of 1, 2 and 4 mg/ml homocyclocreatine (36%, 39%, and 50% plaque reduction, respectively). The therapeutic index for homocyclocreatine was routinely lower than that for cyclocreatine, reflecting increased cytotoxicity.

In addition, using the CPE reduction assay described in Example 5, homocyclocreatine was tested in parallel with cyclocreatine against Pseudorabies virus in MDBK cells, GPCMV, strain 22122 in GPE cells, and TK− strain BW10168 of HSV-1 in Vero cells. Weak antiviral activity (Ave. CPE 3.7) against GPCMV was observed at a concentration of 12.5 mg/ml homocyclocreatine.

Equivalents

Those skilled in the art will recognize or be able to ascertain, using no more than routine experimentation, many equivalents to the specific embodiments of the invention described herein. Such equivalents are intended to be encompassed by the following claims.

We claim:

1. A method for treating a subject for viral infection, comprising:
   administering an antiviral effective amount of a creatine compound to a subject such that the subject is treated for viral infection, wherein the creatine compound is of the general formula:

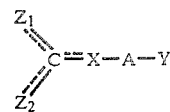

and pharmaceutically acceptable salts thereof, wherein:
a) Y is selected from the group consisting of: $-CO_2H$, $-NHOH$, $-NO_2$, $-SO_3H$, $-C(=O)NHSO_2J$ and $-P(=O)(OH)(OJ)$, wherein J is selected from the group consisting of: hydrogen, $C_1-C_6$ straight chain alkyl, $C_3-C_6$ branched alkyl, $C_2-C_6$ straight alkenyl, $C_3-C_6$ branched alkenyl, and aryl;
b) A is selected from the group consisting of: C, CH, $C_1-C_5$ alkyl, $C_2-C_5$ alkenyl, $C_2-C_5$ alkynyl, and $C_1-C_5$ alkoyl chain, each having 0-2 substituents which are selected independently from the group consisting of:
   1) K, where K is selected from the group consisting of: $C_1-C_6$ straight alkyl, $C_2-C_6$ straight alkenyl, $C_1-C_6$ straight alkoyl, $C_3-C_6$ branched alkyl, $C_3-C_6$ branched alkenyl, and $C_4-C_6$ branched alkoyl, K having 0-2 substituents independently selected from the group consisting of: bromo, chloro, epoxy and acetoxy;
   2) an aryl group selected from the group consisting of: a 1-2 ring carbocycle and a 1-2 ring heterocycle, wherein the aryl group contains 0-2 substituents independently selected from the group consisting of: $-CH_2L$ and $-COCH_2L$ where L is independently selected from the group consisting of: bromo, chloro, epoxy and acetoxy; and
   3) $-NH-M$, wherein M is selected from the group consisting of: hydrogen, $C_1-C_4$ alkyl, $C_2-C_4$ alkenyl, $C_1-C_4$ alkoyl, $C_3-C_4$ branched alkyl, $C_3-C_4$ branched alkenyl, and $C_4$ branched alkoyl;
(c) X is selected from the group consisting of: $NR_1$, $CHR_1$, $CR_1$, O and S, wherein $R_1$ is selected from the group consisting of:
   (1) hydrogen;
   (2) K where K is selected from the group consisting of: $C_1-C_6$ straight alkyl, $C_2-C_6$ straight alkenyl, $C_1-C_6$ straight alkoyl, $C_3-C_6$ branched alkyl, $C_3-C_6$ branched alkenyl, and $C_4-C_6$ branched alkoyl, K having 0-2 substituents independently selected from the group consisting of: bromo, chloro, epoxy and acetoxy;
   (3) an aryl group selected from the group consisting of a 1-2 ring carbocycle and a 1-2 ring heterocycle, wherein the aryl group contains 0-2 substituents independently selected from the group consisting of: $CH_2L$ and $COCH_2L$ wherein L is independently selected from the group consisting of: bromo, chloro, epoxy and acetoxy;
   (4) a $C_5-C_9$ $\alpha$-amino-$\omega$-methyl-$\omega$-adenosylcarboxylic acid attached via the $\omega$-methyl carbon;

(5) a C$_5$–C$_9$ α-amino-ω-aza-ω-methyl-ω-adenosylcarboxylic acid attached via the ω-methyl carbon; and (6) a C$_5$–C$_9$ α-amino-ω-thia-ω-methyl-ω-adenosylcarboxylic acid attached via the ω-methyl carbon;

(d) Z$_1$ and Z$_2$ are chosen independently from the group consisting of: =O, —NHR$_2$, —CH$_2$R$_2$, —NR$_2$OH; wherein Z$_1$ and Z$_2$ may not both be =O and wherein R$_2$ is selected from the group consisting of:

(1) hydrogen;

(2) K, where K is selected from the group consisting of: C$_1$–C$_6$ straight alkyl, C$_2$–C$_6$ straight alkenyl, C$_1$–C$_6$ straight alkoyl, C$_3$–C$_6$ branched alkyl, C$_3$–C$_6$ branched alkenyl, and C$_4$–C$_6$ branched alkoyl, K having 0–2 substituents independently selected from the group consisting of: bromo, chloro, epoxy and acetoxy;

(3) an aryl group selected from the group consisting of a 1–2 ring carbocycle and a 1–2 ring heterocycle, wherein the aryl group contains 0–2 substituents independently selected from the group consisting of: —CH$_2$L and —COCH$_2$L wherein L is independently selected from the group consisting of: bromo, chloro, epoxy and acetoxy;

(4) a C$_4$–C$_8$ α-amino-carboxylic acid attached via the ω-carbon;

(5) B, wherein B is selected from the group consisting of: —CO$_2$H, —NHOH, —SO$_3$H, —NO$_2$, —OP(=O)(OH)(OJ) and —P(=O)-(OH) (OJ), wherein J is selected from the group consisting of: hydrogen, C$_1$–C$_6$ straight alkyl, C$_3$–C$_6$ branched alkyl, C$_2$–C$_6$ straight alkenyl, C$_3$–C$_6$ branched alkenyl, and aryl, wherein B is optionally connected to the nitrogen via a linker selected from the group consisting of: C$_1$–C$_2$ alkyl, C$_2$ alkenyl, and C$_1$–C$_2$ alkoyl;

(6) -D-E, wherein D is selected from the group consisting of: C$_1$–C$_3$ straight alkyl, C$_3$ branched alkyl, C$_2$–C$_3$ straight alkenyl, C$_3$ branched alkenyl, C$_1$–C$_3$ straight alkoyl, aryl, and aroyl; and E is selected from the group consisting of: —(PO$_3$)$_n$NMP, where n is 0–2 and NMP is a ribonucleotide monophosphate connected via the 5'-phosphate, 3'-phosphate or the aromatic ring of the base; —[P(=O)-(OCH$_3$)(O)]$_m$—Q, where m is 0–3 and Q is a ribonucleoside connected via the ribose or the aromatic ring of the base; —[P(=O)-(OH)(CH$_2$)]$_m$—Q, where m is 0–3 and Q is a ribonucleoside connected via the ribose or the aromatic ring of the base; and an aryl group containing 0–3 substituents chosen independently from the group consisting of: Cl, Br, epoxy, acetoxy, —OG, —C(=O)G, and —CO$_2$G, where G is independently selected from the group consisting of: C$_1$–C$_6$ straight alkyl, C$_2$–C$_6$ straight alkenyl, C$_1$–C$_6$ straight alkoyl, C$_3$–C$_6$ branched alkyl, C$_3$–C$_6$ branched alkenyl, C$_4$–C$_6$ branched alkoyl, wherein E may be attached to any point to D, and if D is alkyl or alkenyl, D may be connected at either or both ends by an amide linkage; and (7) -E, wherein E is selected from the group consisting of —(PO$_3$)$_n$NMP, where n is 0–2 and NMP is a ribonucleotide monophosphate connected via the 5'-phosphate, 3'-phosphate or the aromatic ring of the base; —[P(=O)-(OCH$_3$)(O)]$_m$—Q, where m is 0–3 and Q is a ribonucleoside connected via the ribose or the aromatic ring of the base; —[P(=O)-(OH)(CH$_2$)]$_m$—Q, where m is 0–3 and Q is a ribonucleoside connected via the ribose or the aromatic ring of the base; and an aryl group containing 0–3 substituents chose independently from the group consisting of: Cl, Br, epoxy, acetoxy, —OG, —C(=O)G, and —CO$_2$G, where G is independently selected from the group consisting of: C$_1$–C$_6$ straight alkyl, C$_2$–C$_6$ straight alkenyl, C$_1$–C$_6$ straight alkoyl, C$_3$–C$_6$ branched alkyl, C$_3$–C$_6$ branched alkenyl, C$_4$–C$_6$ branched alkoyl; and if E is aryl, E may be connected by an amide linkage;

(e) if R$_1$ and at least one R$_2$ group are present, R$_1$ may be connected by a single or double bond to an R$_2$ group to form a cycle of 5 to 7 members;

(f) if two R$_2$ groups are present, they may be connected by a single or a double bond to form a cycle of 4 to 7 members; and (g) if R$_1$ is present and Z$_1$ or Z$_2$ is selected from the group consisting of —NHR$_2$, —CH$_2$R$_2$ and —NR$_2$OH, then R$_1$ may be connected by a single or double bond to the carbon or nitrogen of either Z$_1$ or Z$_2$ to form a cycle of 4 to 7 members.

2. The method of claim 1 wherein the subject is treated for viral infection by reducing or eliminating symptoms associated with a preexisting viral infection.

3. The method of claim 1 wherein the subject is treated for viral infection by preventing the occurrence of viral infection within the subject.

4. The method of claim 1 wherein the viral infection is from a herpes virus.

5. The method of claim 4 wherein the virus is Herpes Simplex Virus Type 1.

6. The method of claim 4 wherein the virus is Herpes Simplex Virus Type 2.

7. The method of claim 4 wherein the herpes virus is a cytomegalovirus.

8. The method of claim 7 wherein the cytomegalovirus is human.

9. The method of claim 4 wherein the herpes virus is varicella-zoster virus.

10. The method of claim 1 wherein the virus is an adenovirus.

11. The method of any one of claims 1–10 wherein the creatine compound is cyclocreatine.

12. The method of any one of claims 1–10 wherein the creatine compound is homocyclocreatine.

13. The method of any one of claims 1–10 wherein the creatine compound is selected from the group consisting of:

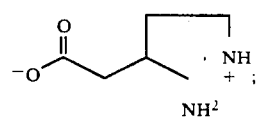

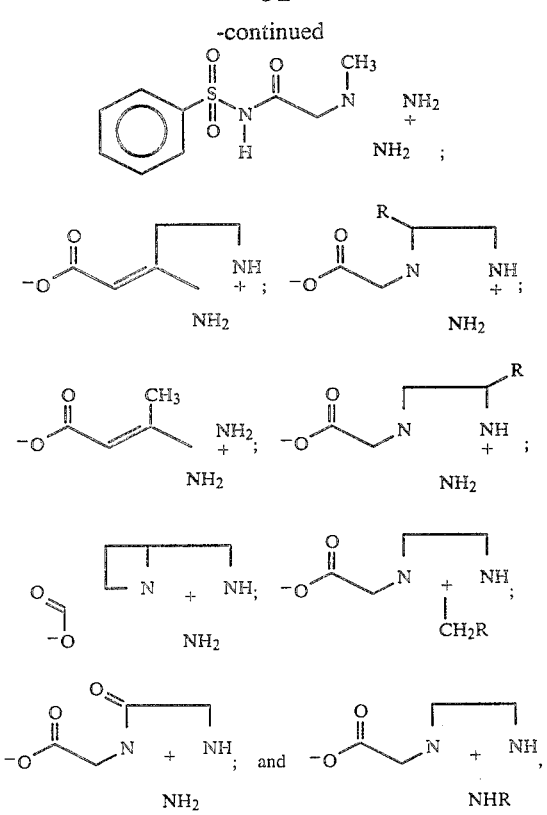

14. The method of any one of claims 1-10 further comprising coadministering a nucleoside analog to the subject.

15. The method of claim 11 further comprising coadministering a nucleoside analog to the subject.

16. The method of claim 12 further comprising coadministering a nucleoside analog to the subject.

17. The method of claim 13 further comprising coadministering a nucleoside analog to the subject.

18. The method of claim 14 wherein the nucleoside analog is selected from the group consisting of ganciclovir, idoxoridine, trifluoridine, vidarabine, dideoxyinosine, and azidothymidine.

19. The method of claim 15 wherein the nucleoside analog is selected from the group consisting of ganciclovir, idoxoridine, trifluoridine, vidarabine, dideoxyinosine, and azidothymidine.

20. The method of claim 16 wherein the nucleoside analog is selected from the group consisting of ganciclovir, idoxoridine, trifluoridine, vidarabine, dideoxyinosine, and azidothymidine.

21. The method of claim 17 wherein the nucleoside analog is selected from the group consisting of ganciclovir, idoxoridine, trifluoridine, vidarabine, dideoxyinosine, and azidothymidine.

22. The method of claim 14 wherein the nucleoside analog is acyclovir.

23. The method of claim 15 wherein the nucleoside analog is acyclovir.

24. The method of claim 16 wherein the nucleoside analog is acyclovir.

25. The method of claim 17 wherein the nucleoside analog is acyclovir.

26. The method of any one of claims 1-10 further comprising coadministering foscarnet or fosfonet to the subject.

27. The method of claim 11 further comprising coadministering foscarnet or fosfonet to the subject.

28. The method of claim 12 further comprising coadministering foscarnet or fosfonet to the subject.

29. The method of claim 13 further comprising coadministering foscarnet or fosfonet to the subject.

30. A method for treating a subject for viral infection, comprising:
administering an antiviral effective amount of cyclocreatine to a subject such that the subject is treated for viral infection.

31. The method of claim 30 wherein the subject is treated for viral infection by reducing or eliminating symptoms associated with a preexisting viral infection.

32. The method of claim 30 wherein the subject is treated for viral infection by preventing the occurrence of viral infection within the subject.

33. The method of claim 30, 31 or 32 further comprising coadministering a nucleoside analog to the subject.

34. The method of claim 33 wherein the nucleoside analog is selected from the group consisting of ganciclovir, idoxoridine, trifluoridine, vidarabine, dideoxyinosine, and azidothymidine.

35. The method of claim 33 wherein the nucleoside analog is acyclovir.

36. The method of claim 30, 31 or 32 further comprising coadministering foscarnet or fosfonet to the subject.

37. The method of claim 30, 31 or 33 wherein the viral infection is from a herpes virus.

38. The method of claim 33 wherein the viral infection is from a herpes virus.

39. The method of claim 34 wherein the viral infection is from a herpes virus.

40. The method of claim 35 wherein the viral infection is from a herpes virus.

41. The method of claim 36 wherein the viral infection is from a herpes virus.

42. The method of claim 37 wherein the herpes virus is cytomegalovirus.

43. The method of claim 38 wherein the herpes virus is cytomegalovirus.

44. The method of claim 39 wherein the herpes virus is cytomegalovirus.

45. The method of claim 40 wherein the herpes virus is cytomegalovirus.

46. The method of claim 41 wherein the herpes virus is cytomegalovirus.

47. The method of claim 42 wherein the viral infection is treated by treating the condition cytomegalovirus chorioretinitis.

48. The method of claim 43 wherein the viral infection is treated by treating the condition cytomegalovirus chorioretinitis.

49. The method of claim 44 wherein the viral infection is treated by treating the condition cytomegalovirus chorioretinitis.

50. The method of claim 45 wherein the viral infection is treated by treating the condition cytomegalovirus chorioretinitis.

51. The method of claim 46 wherein the viral infection is treated by treating the condition cytomegalovirus chorioretinitis.

52. The method of claim 47 wherein the cytomegalovirus chorioretinitus is in a human.

53. The method of claim 48 wherein the cytomegalovirus chorioretinitus is in a human.

54. The method of claim 49 wherein the cytomegalovirus chorioretinitus is in a human.

55. The method of claim 50 wherein the cytomegalovirus chorioretinitus is in a human.

56. The method of claim 51 wherein the cytomegalovirus chorioretinitus is in a human.

57. A method for treating a subject for viral infection, comprising:
administering an antiviral effective amount of homocyclocreatine to a subject such that the subject is treated for viral infection.

58. The method of claim 57 wherein the subject is treated for viral infection by reducing or eliminating symptoms associated with a preexisting viral infection.

59. The method of claim 57 wherein the subject is treated for viral infection by preventing the occurrence of viral infection within the subject.

60. The method of claim 57, 58 or 59 further comprising coadministering a nucleoside analog to the subject.

61. The method of claim 60 wherein the nucleoside analog is selected from the group consisting of ganciclovir, idoxoridine, trifluoridine, vidarabine, dideoxyinosine, and azidothymidine.

62. The method of claim 60 wherein the nucleoside analog is acyclovir.

63. The method of claim 57, 58 or 59 further comprising coadministering foscarnet or fosfonet to the subject.

64. The method of claim 57, 58 or 59 wherein the viral infection is from a herpes virus.

65. The method of claim 60 wherein the viral infection is from a herpes virus.

66. The method of claim 61 wherein the viral infection is from a herpes virus.

67. The method of claim 62 wherein the viral infection is from a herpes virus.

68. The method of claim 63 wherein the viral infection is from a herpes virus.

69. The method of claim 64 wherein the herpes virus is cytomegalovirus.

70. The method of claim 65 wherein the herpes virus is cytomegalovirus.

71. The method of claim 66 wherein the herpes virus is cytomegalovirus.

72. The method of claim 67 wherein the herpes virus is cytomegalovirus.

73. The method of claim 68 wherein the herpes virus is cytomegalovirus.

74. The method of claim 69 wherein the viral infection is treated by treating the condition cytomegalovirus chorioretinitis.

75. The method of claim 70 wherein the viral infection is treated by treating the condition cytomegalovirus chorioretinitis.

76. The method of claim 71 wherein the viral infection is treated by treating the condition cytomegalovirus chorioretinitis.

77. The method of claim 72 wherein the viral infection is treated by treating the condition cytomegalovirus chorioretinitis.

78. The method of claim 73 wherein the viral infection is treated by treating the condition cytomegalovirus chorioretinitis.

79. The method of claim 74 wherein the cytomegalovirus chorioretinitus is in a human.

80. The method of claim 75 wherein the cytomegalovirus chorioretinitus is in a human.

81. The method of claim 76 wherein the cytomegalovirus chorioretinitus is in a human.

82. The method of claim 77 wherein the cytomegalovirus chorioretinitus is in a human.

83. The method of claim 78 wherein the cytomegalovirus chorioretinitus is in a human.

* * * * *